US010767224B2

(12) United States Patent
Fife et al.

(10) Patent No.: US 10,767,224 B2
(45) Date of Patent: Sep. 8, 2020

(54) HIGH DATA RATE INTEGRATED CIRCUIT WITH POWER MANAGEMENT

(71) Applicant: LIFE TECHNOLOGIES CORPORATION, Carlsbad, CA (US)

(72) Inventors: Keith G. Fife, Palo Alto, CA (US); Jungwook Yang, Waban, MA (US)

(73) Assignee: Life Technologies Corporation, Carlsbad, CA (US)

( * ) Notice: Subject to any disclaimer, the term of this patent is extended or adjusted under 35 U.S.C. 154(b) by 195 days.

(21) Appl. No.: 16/110,341

(22) Filed: Aug. 23, 2018

(65) Prior Publication Data

US 2019/0136315 A1    May 9, 2019

Related U.S. Application Data

(62) Division of application No. 14/965,568, filed on Dec. 10, 2015, now Pat. No. 10,077,472.

(60) Provisional application No. 62/093,611, filed on Dec. 18, 2014.

(51) Int. Cl.
  *C12Q 1/6874* (2018.01)
  *G01N 27/414* (2006.01)
  *G01N 35/00* (2006.01)

(52) U.S. Cl.
  CPC ....... *C12Q 1/6874* (2013.01); *G01N 27/4145* (2013.01); *G01N 27/4148* (2013.01); *G01N 35/00712* (2013.01); *G01N 35/00871* (2013.01); *G01N 2035/00881* (2013.01)

(58) Field of Classification Search
  CPC ............. C12Q 1/6874; G01N 27/4145; G01N 27/4148; G01N 35/00712; G01N 35/00871; G01N 2035/00881
  See application file for complete search history.

(56) References Cited

U.S. PATENT DOCUMENTS

| 4,086,642 A | 4/1978 | Yoshida et al. |
| 4,133,735 A | 1/1979 | Afromowitz et al. |
| 4,411,741 A | 10/1983 | Janata |

(Continued)

FOREIGN PATENT DOCUMENTS

| CN | 1582334 | 2/2005 |
| CN | 101676714 | 3/2010 |

(Continued)

OTHER PUBLICATIONS

Anderson et al., "A system for multiplexed direct electrical detection of DNA synthesis", *Sensors and Actuators B: Chemical*, vol. 129, No. 1, Jan. 2008, pp. 79-86.

(Continued)

*Primary Examiner* — Brian J. Sines

(57) ABSTRACT

A sensor device includes a sensor array and a flow cell in fluid communication with the sensor array. Bias circuitry apply bias arrangements to the sensor array to produce sensor data. Peripheral circuitry coupled to the bias circuitry produces streams of data from the sensor array, the peripheral circuitry having an active mode and an idle mode. Logic to switch the peripheral circuitry between the active mode and the idle mode to control power consumption is provided. A temperature sensor may be included, and the logic can operate with feedback to switch between the active mode and the idle mode to maintain the temperature within an operating range.

14 Claims, 16 Drawing Sheets

(56) References Cited

U.S. PATENT DOCUMENTS

| | | |
|---|---|---|
| 4,437,969 A | 3/1984 | Covington et al. |
| 4,438,354 A | 3/1984 | Haque et al. |
| 4,444,644 A | 4/1984 | Hiramoto |
| 4,490,678 A | 12/1984 | Kuisl et al. |
| 4,641,084 A | 2/1987 | Komatsu |
| 4,660,063 A | 4/1987 | Anthony |
| 4,691,167 A | 9/1987 | Vlekkert et al. |
| 4,701,253 A | 10/1987 | Litenberg et al. |
| 4,722,830 A | 2/1988 | Urie et al. |
| 4,743,954 A | 5/1988 | Brown |
| 4,764,797 A | 8/1988 | Shaw et al. |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,893,088 A | 1/1990 | Myers et al. |
| 4,927,736 A | 5/1990 | Mueller et al. |
| 4,971,903 A | 11/1990 | Hyman |
| 5,009,766 A | 4/1991 | Lauks |
| 5,038,192 A | 8/1991 | Bonneau |
| 5,082,788 A | 1/1992 | Farnsworth et al. |
| 5,110,441 A | 5/1992 | Kinlen et al. |
| 5,113,870 A | 5/1992 | Rossenfeld |
| 5,126,022 A | 6/1992 | Soane et al. |
| 5,126,759 A | 6/1992 | Small et al. |
| 5,132,418 A | 7/1992 | Caruthers et al. |
| 5,138,251 A | 8/1992 | Koshiishi et al. |
| 5,140,393 A | 8/1992 | Hijikihigawa et al. |
| 5,142,236 A | 8/1992 | Maloberti et al. |
| 5,151,587 A | 9/1992 | Machida et al. |
| 5,151,759 A | 9/1992 | Vinal |
| 5,164,319 A | 11/1992 | Hafeman et al. |
| 5,202,576 A | 4/1993 | Liu et al. |
| 5,284,566 A | 2/1994 | Cuomo et al. |
| 5,317,407 A | 5/1994 | Michon |
| 5,319,226 A | 6/1994 | Sohn et al. |
| 5,407,854 A | 4/1995 | Baxter et al. |
| 5,436,149 A | 7/1995 | Barnes |
| 5,439,839 A | 8/1995 | Jang |
| 5,466,348 A | 11/1995 | Holm-Kennedy |
| 5,475,337 A | 12/1995 | Tatsumi |
| 5,490,971 A | 2/1996 | Gifford et al. |
| 5,554,339 A | 9/1996 | Cozzette et al. |
| 5,583,462 A | 12/1996 | Grasshoff |
| 5,587,894 A | 12/1996 | Naruo |
| 5,593,838 A | 1/1997 | Zanzucchi et al. |
| 5,600,451 A | 2/1997 | Maki |
| 5,627,403 A | 5/1997 | Bacchetta et al. |
| 5,631,704 A | 5/1997 | Dickinson et al. |
| 5,637,469 A | 6/1997 | Wilding et al. |
| 5,646,558 A | 7/1997 | Jamshidi et al. |
| 5,702,964 A | 12/1997 | Lee |
| 5,793,230 A | 8/1998 | Chu et al. |
| 5,846,708 A | 12/1998 | Hollis et al. |
| 5,894,284 A | 4/1999 | Garrity et al. |
| 5,907,765 A | 5/1999 | Lescouzeres et al. |
| 5,911,873 A | 6/1999 | McCarron et al. |
| 5,912,560 A | 6/1999 | Pasternak |
| 5,922,591 A | 7/1999 | Anderson et al. |
| 5,923,421 A | 7/1999 | Rajic et al. |
| 5,944,970 A | 8/1999 | Rosenblatt |
| 5,958,703 A | 9/1999 | Dower et al. |
| 5,965,452 A | 10/1999 | Kovacs |
| 6,002,299 A | 12/1999 | Thomsen |
| 6,021,172 A | 2/2000 | Fossum et al. |
| 6,107,032 A | 8/2000 | Kilger et al. |
| 6,191,444 B1 | 2/2001 | Clampitt et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,274,320 B1 | 8/2001 | Rothberg et al. |
| 6,275,061 B1 | 8/2001 | Tomita |
| 6,280,586 B1 | 8/2001 | Wolf et al. |
| 6,294,133 B1 | 9/2001 | Sawada et al. |
| 6,327,410 B1 | 12/2001 | Walt et al. |
| 6,353,324 B1 | 3/2002 | Uber, III et al. |
| 6,355,431 B1 | 3/2002 | Chee et al. |
| 6,361,671 B1 | 3/2002 | Mathies et al. |
| 6,372,291 B1 | 4/2002 | Hua et al. |
| 6,376,256 B1 | 4/2002 | Dunnington et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,490,220 B1 | 12/2002 | Merritt et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,535,824 B1 | 3/2003 | Mansky et al. |
| 6,537,881 B1 | 3/2003 | Rangarajan et al. |
| 6,538,593 B2 | 3/2003 | Yang et al. |
| 6,545,620 B2 | 4/2003 | Groeneweg |
| 6,571,189 B2 | 5/2003 | Jensen et al. |
| 6,602,702 B1 | 8/2003 | McDevitt et al. |
| 6,605,428 B2 | 8/2003 | Kilger et al. |
| 6,613,513 B1 | 9/2003 | Parce et al. |
| 6,618,083 B1 | 9/2003 | Chen et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,657,269 B2 | 12/2003 | Migliorato et al. |
| 6,671,341 B1 | 12/2003 | Kinget et al. |
| 6,682,899 B2 | 1/2004 | Bryan et al. |
| 6,682,936 B2 | 1/2004 | Kovacs |
| 6,686,638 B2 | 2/2004 | Fischer et al. |
| 6,700,814 B1 | 3/2004 | Nahas et al. |
| 6,703,660 B2 | 3/2004 | Yitzchaik et al. |
| 6,716,629 B2 | 4/2004 | Hess et al. |
| 6,762,022 B2 | 7/2004 | Makarov et al. |
| 6,770,472 B2 | 8/2004 | Manalis et al. |
| 6,795,006 B1 | 9/2004 | Delight et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,841,128 B2 | 1/2005 | Kambara et al. |
| 6,859,570 B2 | 2/2005 | Walt et al. |
| 6,878,255 B1 | 4/2005 | Wang et al. |
| 6,888,194 B2 | 5/2005 | Yoshino |
| 6,898,121 B2 | 5/2005 | Chien et al. |
| 6,906,524 B2 | 6/2005 | Chung et al. |
| 6,919,211 B1 | 7/2005 | Fodor et al. |
| 6,926,865 B2 | 8/2005 | Howard |
| 6,927,045 B2 | 8/2005 | Hadd et al. |
| 6,929,944 B2 | 8/2005 | Matson |
| 6,939,451 B2 | 9/2005 | Zhao et al. |
| 6,953,958 B2 | 10/2005 | Baxter et al. |
| 6,958,216 B2 | 10/2005 | Kelley et al. |
| 6,969,488 B2 | 11/2005 | Bridgham et al. |
| 6,998,274 B2 | 2/2006 | Chee et al. |
| 7,008,550 B2 | 3/2006 | Li et al. |
| 7,019,305 B2 | 3/2006 | Eversmann et al. |
| 7,022,288 B1 | 4/2006 | Boss |
| 7,033,754 B2 | 4/2006 | Chee et al. |
| 7,037,687 B2 | 5/2006 | Williams et al. |
| 7,045,097 B2 | 5/2006 | Kovacs |
| 7,049,645 B2 | 5/2006 | Sawada et al. |
| 7,060,431 B2 | 6/2006 | Chee et al. |
| 7,067,886 B2 | 6/2006 | Bonges et al. |
| 7,084,641 B2 | 8/2006 | Brederlow et al. |
| 7,085,502 B2 | 8/2006 | Shushakob et al. |
| 7,087,387 B2 | 8/2006 | Gerdes et al. |
| 7,091,059 B2 | 8/2006 | Rhodes |
| 7,097,973 B1 | 8/2006 | Zenhausern |
| 7,105,300 B2 | 9/2006 | Parce et al. |

(56) References Cited

U.S. PATENT DOCUMENTS

| | | |
|---|---|---|
| 7,106,089 B2 | 9/2006 | Nakano et al. |
| 7,129,554 B2 | 10/2006 | Lieber et al. |
| 7,169,560 B2 | 1/2007 | Lapidus et al. |
| 7,173,445 B2 | 2/2007 | Fujii et al. |
| 7,190,026 B2 | 3/2007 | Lotfi et al. |
| 7,192,745 B2 | 3/2007 | Jaeger |
| 7,193,453 B2 | 3/2007 | Wei et al. |
| 7,211,390 B2 | 5/2007 | Rothberg |
| 7,220,550 B2 | 5/2007 | Keen |
| 7,223,371 B2 | 5/2007 | Hayenga et al. |
| 7,223,540 B2 | 5/2007 | Pourmand et al. |
| 7,226,734 B2 | 6/2007 | Chee et al. |
| 7,229,799 B2 | 6/2007 | Williams |
| 7,235,389 B2 | 6/2007 | Lim et al. |
| 7,238,323 B2 | 7/2007 | Knapp et al. |
| 7,239,188 B1 | 7/2007 | Xu et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,264,934 B2 | 9/2007 | Fuller |
| 7,265,929 B2 | 9/2007 | Umeda et al. |
| 7,267,751 B2 | 9/2007 | Gelbart et al. |
| 7,276,749 B2 | 10/2007 | Martin et al. |
| 7,279,588 B2 | 10/2007 | Hong et al. |
| 7,282,370 B2 | 10/2007 | Bridgham et al. |
| 7,285,384 B2 | 10/2007 | Fan et al. |
| 7,291,496 B2 | 11/2007 | Holm-Kennedy |
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,317,484 B2 | 1/2008 | Dosluoglu et al. |
| 7,323,305 B2 | 1/2008 | Leamon et al. |
| 7,335,526 B2 | 2/2008 | Peters et al. |
| 7,335,762 B2 | 2/2008 | Rothberg et al. |
| 7,359,058 B2 | 4/2008 | Kranz et al. |
| 7,361,946 B2 | 4/2008 | Johnson et al. |
| 7,363,717 B2 | 4/2008 | Ekseth et al. |
| 7,381,936 B2 | 6/2008 | Tan et al. |
| 7,394,263 B2 | 7/2008 | Pechstein et al. |
| 7,419,636 B2 | 9/2008 | Aker et al. |
| 7,425,431 B2 | 9/2008 | Church et al. |
| 7,455,971 B2 | 11/2008 | Chee et al. |
| 7,462,452 B2 | 12/2008 | Williams et al. |
| 7,462,512 B2 | 12/2008 | Levon et al. |
| 7,462,709 B2 | 12/2008 | Jaeger |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,476,504 B2 | 1/2009 | Turner |
| 7,482,153 B2 | 1/2009 | Okada et al. |
| 7,482,677 B2 | 1/2009 | Lee et al. |
| 7,499,513 B1 | 3/2009 | Tetzlaff et al. |
| 7,515,124 B2 | 4/2009 | Yaguma et al. |
| 7,534,097 B2 | 5/2009 | Wong et al. |
| 7,538,827 B2 | 5/2009 | Chou |
| 7,575,865 B2 | 8/2009 | Leamon et al. |
| 7,576,037 B2 | 8/2009 | Engelhardt et al. |
| 7,590,211 B1 | 9/2009 | Burney |
| 7,595,883 B1 | 9/2009 | El Gamal et al. |
| 7,605,650 B2 | 10/2009 | Forbes |
| 7,608,810 B2 | 10/2009 | Yamada |
| 7,609,093 B2 | 10/2009 | Sarig et al. |
| 7,609,303 B1 | 10/2009 | Lee |
| 7,612,369 B2 | 11/2009 | Stasiak |
| 7,612,817 B2 | 11/2009 | Tay |
| 7,614,135 B2 | 11/2009 | Santini, Jr. et al. |
| 7,622,294 B2 | 11/2009 | Walt et al. |
| 7,645,596 B2 | 1/2010 | Williams et al. |
| 7,649,358 B2 | 1/2010 | Toumazou et al. |
| 7,667,501 B2 | 2/2010 | Surendranath et al. |
| 7,686,929 B2 | 3/2010 | Toumazou et al. |
| 7,695,907 B2 | 4/2010 | Miyahara et al. |
| 7,733,401 B2 | 6/2010 | Takeda |
| 7,772,383 B2 | 8/2010 | Chakrabarti et al. |
| 7,785,785 B2 | 8/2010 | Pourmand et al. |
| 7,785,790 B1 | 8/2010 | Church et al. |
| 7,794,584 B2 | 9/2010 | Chodavarapu et al. |
| 7,821,806 B2 | 10/2010 | Horiuchi |
| 7,824,900 B2 | 11/2010 | Iwadate et al. |
| 7,838,226 B2 | 11/2010 | Kamahori et al. |
| 7,842,377 B2 | 11/2010 | Lanphere et al. |
| 7,842,457 B2 | 11/2010 | Berka et al. |
| 7,859,029 B2 | 12/2010 | Lee et al. |
| 7,859,291 B2 | 12/2010 | Kim |
| 7,875,440 B2 | 1/2011 | Williams et al. |
| 7,884,398 B2 | 2/2011 | Levon et al. |
| 7,885,490 B2 | 2/2011 | Heideman et al. |
| 7,888,013 B2 | 2/2011 | Miyahara et al. |
| 7,888,015 B2 | 2/2011 | Toumazou et al. |
| 7,888,708 B2 | 2/2011 | Yazawa et al. |
| 7,890,891 B2 | 2/2011 | Stuber et al. |
| 7,898,277 B2 | 3/2011 | Weir |
| 7,923,240 B2 | 4/2011 | Su |
| 7,927,797 B2 | 4/2011 | Nobile et al. |
| 7,932,034 B2 | 4/2011 | Esfandyarpour et al. |
| 7,948,015 B2 | 5/2011 | Rothberg et al. |
| 7,955,995 B2 | 6/2011 | Kakehata et al. |
| 7,960,776 B2 | 6/2011 | Kim et al. |
| 7,972,828 B2 | 7/2011 | Ward et al. |
| 7,981,362 B2 | 7/2011 | Glezer et al. |
| 8,012,690 B2 | 9/2011 | Berka et al. |
| 8,017,938 B2 | 9/2011 | Gomez et al. |
| 8,035,175 B2 | 10/2011 | Shim et al. |
| 8,052,863 B2 | 11/2011 | Suzuki et al. |
| 8,067,731 B2 | 11/2011 | Matyjaszczyk et al. |
| 8,072,188 B2 | 12/2011 | Yorinobu et al. |
| 8,114,591 B2 | 2/2012 | Toumazou et al. |
| 8,124,936 B1 | 2/2012 | Lagna |
| 8,133,698 B2 | 3/2012 | Silver |
| 8,138,496 B2 | 3/2012 | Li et al. |
| 8,154,480 B2 | 4/2012 | Shishido et al. |
| 8,199,859 B2 | 6/2012 | Zerbe et al. |
| 8,217,433 B1 | 7/2012 | Fife |
| 8,227,877 B2 | 7/2012 | Lee et al. |
| 8,231,831 B2 | 7/2012 | Hartzell et al. |
| 8,232,813 B2 | 7/2012 | Burdett et al. |
| 8,247,849 B2 | 8/2012 | Fife et al. |
| 8,248,356 B2 | 8/2012 | Chen |
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg |
| 8,277,628 B2 | 10/2012 | Ronaghi et al. |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,340,914 B2 | 12/2012 | Gatewood et al. |
| 8,343,856 B2 | 1/2013 | Therrien et al. |
| 8,349,167 B2 | 1/2013 | Rothberg et al. |
| 8,357,547 B2 | 1/2013 | Lee et al. |
| 8,361,713 B2 | 1/2013 | Bridgham et al. |
| 8,383,396 B2 | 2/2013 | Kamahori et al. |
| 8,415,716 B2 | 4/2013 | Rothberg et al. |
| 8,421,437 B2 | 4/2013 | Levine |
| 8,426,898 B2 | 4/2013 | Rothberg et al. |
| 8,426,899 B2 | 4/2013 | Rothberg et al. |
| 8,435,395 B2 | 5/2013 | Rothberg et al. |
| 8,441,044 B2 | 5/2013 | Rothberg et al. |
| 8,445,194 B2 | 5/2013 | Drmanac et al. |
| 8,445,945 B2 | 5/2013 | Rothberg et al. |
| 8,449,824 B2 | 5/2013 | Sun |
| 8,450,781 B2 | 5/2013 | Rothberg et al. |
| 8,470,164 B2 | 6/2013 | Rothberg et al. |
| 8,487,790 B2 | 7/2013 | Fife et al. |
| 8,492,800 B2 | 7/2013 | Rothberg et al. |
| 8,496,802 B2 | 7/2013 | Rothberg et al. |
| 8,502,278 B2 | 8/2013 | Rothberg et al. |
| 8,519,448 B2 | 8/2013 | Rothberg et al. |
| 8,524,057 B2 | 9/2013 | Rothberg et al. |
| 8,530,941 B2 | 9/2013 | Rothberg et al. |
| 8,535,513 B2 | 9/2013 | Rothberg et al. |

(56) References Cited

U.S. PATENT DOCUMENTS

| | | |
|---|---|---|
| 8,552,771 B1 | 10/2013 | Jordan et al. |
| 8,558,288 B2 | 10/2013 | Rothberg et al. |
| 8,575,664 B2 | 11/2013 | Rothberg et al. |
| 8,592,154 B2 | 11/2013 | Rearick |
| 8,653,567 B2 | 2/2014 | Fife |
| 8,658,017 B2 | 2/2014 | Rothberg et al. |
| 8,673,627 B2 | 3/2014 | Nobile et al. |
| 8,685,230 B2 | 4/2014 | Rothberg et al. |
| 8,685,298 B2 | 4/2014 | Rothberg et al. |
| 8,728,844 B1 | 5/2014 | Liu et al. |
| 8,731,847 B2 | 5/2014 | Johnson et al. |
| 8,742,469 B2 | 6/2014 | Milgrew |
| 8,742,472 B2 | 6/2014 | Rothberg et al. |
| 8,747,748 B2 | 6/2014 | Li et al. |
| 8,748,947 B2 | 6/2014 | Milgrew et al. |
| 8,764,969 B2 | 7/2014 | Rothberg et al. |
| 8,766,327 B2 | 7/2014 | Milgrew |
| 8,766,328 B2 | 7/2014 | Rothberg et al. |
| 8,776,573 B2 | 7/2014 | Rearick et al. |
| 8,786,331 B2 | 7/2014 | Jordan et al. |
| 8,796,036 B2 | 8/2014 | Fife et al. |
| 8,821,798 B2 | 9/2014 | Bustillo et al. |
| 8,823,380 B2 | 9/2014 | Levine et al. |
| 8,841,217 B1 | 9/2014 | Fife et al. |
| 8,847,637 B1 | 9/2014 | Guyton |
| 8,912,005 B1 | 12/2014 | Fife et al. |
| 8,936,763 B2 | 1/2015 | Rothberg et al. |
| 8,945,912 B2 | 2/2015 | Bashir et al. |
| 8,962,366 B2 | 2/2015 | Putnam et al. |
| 8,963,216 B2 | 2/2015 | Fife et al. |
| 8,983,783 B2 | 3/2015 | Johnson et al. |
| 9,023,674 B2 | 5/2015 | Shen et al. |
| 9,164,070 B2 | 10/2015 | Fife |
| 9,201,041 B2 | 12/2015 | Dalton et al. |
| 9,270,264 B2 | 2/2016 | Jordan et al. |
| 9,389,199 B2 | 7/2016 | Cheng et al. |
| 9,458,502 B2 | 10/2016 | Rothberg et al. |
| 9,618,475 B2 | 4/2017 | Rothberg et al. |
| 9,671,363 B2 | 6/2017 | Fife et al. |
| 9,823,217 B2 | 11/2017 | Fife et al. |
| 10,077,472 B2 | 9/2018 | Fife et al. |
| 2002/0012933 A1 | 1/2002 | Rothberg et al. |
| 2002/0042388 A1 | 4/2002 | Cooper et al. |
| 2002/0081714 A1 | 6/2002 | Jain et al. |
| 2002/0085136 A1 | 7/2002 | Moon et al. |
| 2002/0150909 A1 | 10/2002 | Stuelpnagel et al. |
| 2002/0168678 A1 | 11/2002 | Williams et al. |
| 2003/0020334 A1 | 1/2003 | Nozu et al. |
| 2003/0044833 A1 | 3/2003 | Elouard et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0108867 A1 | 6/2003 | Chee et al. |
| 2003/0119020 A1 | 6/2003 | Stevens et al. |
| 2003/0124572 A1 | 7/2003 | Umek et al. |
| 2003/0124599 A1 | 7/2003 | Chen et al. |
| 2003/0141928 A1 | 7/2003 | Lee |
| 2003/0141929 A1 | 7/2003 | Casper et al. |
| 2003/0152994 A1 | 8/2003 | Woudenberg et al. |
| 2003/0155942 A1 | 8/2003 | Thewes |
| 2003/0175990 A1 | 9/2003 | Hayenga et al. |
| 2003/0186262 A1 | 10/2003 | Cailloux |
| 2003/0211502 A1 | 11/2003 | Sauer et al. |
| 2003/0215791 A1 | 11/2003 | Garini et al. |
| 2003/0215857 A1 | 11/2003 | Kilger et al. |
| 2003/0224419 A1 | 12/2003 | Corcoran et al. |
| 2003/0227296 A1 | 12/2003 | Lee |
| 2004/0002470 A1 | 1/2004 | Keith et al. |
| 2004/0023253 A1 | 2/2004 | Kunwar et al. |
| 2004/0079636 A1 | 4/2004 | Hsia et al. |
| 2004/0106211 A1 | 6/2004 | Kauer et al. |
| 2004/0121354 A1 | 6/2004 | Yazawa et al. |
| 2004/0130377 A1 | 7/2004 | Takeda et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0185591 A1 | 9/2004 | Hsiung et al. |
| 2004/0197803 A1 | 10/2004 | Yaku et al. |
| 2005/0006234 A1 | 1/2005 | Hassibi |
| 2005/0009022 A1 | 1/2005 | Weiner et al. |
| 2005/0031490 A1 | 2/2005 | Gumbrecht et al. |
| 2005/0032075 A1 | 2/2005 | Yaku et al. |
| 2005/0058990 A1 | 3/2005 | Guia et al. |
| 2005/0093072 A1 | 5/2005 | Bonges et al. |
| 2005/0093645 A1 | 5/2005 | Watanabe et al. |
| 2005/0095602 A1 | 5/2005 | West et al. |
| 2005/0100939 A1 | 5/2005 | Namsaraev et al. |
| 2005/0106587 A1 | 5/2005 | Klapproth et al. |
| 2005/0151181 A1 | 7/2005 | Beintner et al. |
| 2005/0156207 A1 | 7/2005 | Yazawa et al. |
| 2005/0156584 A1 | 7/2005 | Feng |
| 2005/0181440 A1 | 8/2005 | Chee et al. |
| 2005/0189960 A1 | 9/2005 | Tajima |
| 2005/0191698 A1 | 9/2005 | Chee et al. |
| 2005/0202582 A1 | 9/2005 | Eversmann et al. |
| 2005/0206548 A1 | 9/2005 | Muramatsu et al. |
| 2005/0212016 A1 | 9/2005 | Brunner et al. |
| 2005/0221473 A1 | 10/2005 | Dubin et al. |
| 2005/0230245 A1 | 10/2005 | Morgenshtein et al. |
| 2005/0239132 A1 | 10/2005 | Klapprith |
| 2005/0282224 A1 | 12/2005 | Fouillet et al. |
| 2006/0000772 A1 | 1/2006 | Sano et al. |
| 2006/0024711 A1 | 2/2006 | Lapidus et al. |
| 2006/0035400 A1 | 2/2006 | Wu et al. |
| 2006/0038601 A1 | 2/2006 | Giguere |
| 2006/0057025 A1 | 3/2006 | Eversmann et al. |
| 2006/0057604 A1 | 3/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke et al. |
| 2006/0182664 A1 | 8/2006 | Peck et al. |
| 2006/0197118 A1 | 9/2006 | Migliorato et al. |
| 2006/0199193 A1 | 9/2006 | Koo et al. |
| 2006/0199493 A1 | 9/2006 | Hartmann et al. |
| 2006/0205061 A1 | 9/2006 | Roukes |
| 2006/0219558 A1 | 10/2006 | Hafeman et al. |
| 2006/0228721 A1 | 10/2006 | Leamon et al. |
| 2006/0246497 A1 | 11/2006 | Huang et al. |
| 2006/0266946 A1 | 11/2006 | Defrise et al. |
| 2006/0269927 A1 | 11/2006 | Lieber |
| 2006/0289726 A1 | 12/2006 | Paulus et al. |
| 2007/0087362 A1 | 4/2007 | Church et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0096164 A1 | 5/2007 | Peters et al. |
| 2007/0099173 A1 | 5/2007 | Spira et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0233477 A1 | 10/2007 | Halowani et al. |
| 2007/0247170 A1 | 10/2007 | Barbaro et al. |
| 2007/0250274 A1 | 10/2007 | Volkov et al. |
| 2007/0262363 A1 | 11/2007 | Tao et al. |
| 2007/0278111 A1 | 12/2007 | Boussaad et al. |
| 2007/0278488 A1 | 12/2007 | Hirabayashi et al. |
| 2008/0003142 A1 | 1/2008 | Link et al. |
| 2008/0014589 A1 | 1/2008 | Link et al. |
| 2008/0047836 A1 | 2/2008 | Strand et al. |
| 2008/0063566 A1 | 3/2008 | Matsumoto et al. |
| 2008/0085219 A1 | 4/2008 | Beebe et al. |
| 2008/0096216 A1 | 4/2008 | Quake |
| 2008/0111161 A1 | 5/2008 | Sorge et al. |
| 2008/0121946 A1 | 5/2008 | Youn et al. |
| 2008/0136933 A1 | 6/2008 | Dosluoglu et al. |
| 2008/0164917 A1 | 7/2008 | Floyd et al. |
| 2008/0178692 A1 | 7/2008 | Jung et al. |
| 2008/0185616 A1 | 8/2008 | Johnson et al. |
| 2008/0204048 A1 | 8/2008 | Stasiak et al. |
| 2008/0205559 A1 | 8/2008 | Iida |
| 2008/0210931 A1 | 9/2008 | Truong et al. |
| 2008/0230386 A1 | 9/2008 | Srinivasan et al. |

(56) References Cited

U.S. PATENT DOCUMENTS

| | | |
|---|---|---|
| 2009/0030117 A1 | 1/2009 | Lanphere et al. |
| 2009/0048124 A1 | 2/2009 | Leamon et al. |
| 2009/0062132 A1 | 3/2009 | Borner |
| 2009/0075383 A1 | 3/2009 | El Gamal et al. |
| 2009/0079414 A1 | 3/2009 | Levon et al. |
| 2009/0120905 A1 | 5/2009 | Kohl et al. |
| 2009/0121258 A1 | 5/2009 | Kumar |
| 2009/0127689 A1 | 5/2009 | Ye et al. |
| 2009/0149607 A1 | 6/2009 | Karim et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2009/0273386 A1 | 11/2009 | Korobeynikov et al. |
| 2010/0007326 A1 | 1/2010 | Nakazato |
| 2010/0026814 A1 | 2/2010 | Shimoda |
| 2010/0039146 A1 | 2/2010 | Park et al. |
| 2010/0052765 A1 | 3/2010 | Makino |
| 2010/0105373 A1 | 4/2010 | Kanade |
| 2010/0133547 A1 | 6/2010 | Kunze et al. |
| 2010/0137143 A1 | 6/2010 | Rothberg et al. |
| 2010/0176463 A1 | 7/2010 | Koizumi et al. |
| 2010/0244106 A1 | 9/2010 | Parker et al. |
| 2010/0273166 A1 | 10/2010 | Garcia |
| 2010/0301398 A1 | 12/2010 | Rothberg et al. |
| 2011/0037121 A1 | 2/2011 | Lee et al. |
| 2011/0062972 A1 | 3/2011 | Je et al. |
| 2011/0114827 A1 | 5/2011 | Yamaoka et al. |
| 2011/0165557 A1 | 7/2011 | Ah et al. |
| 2011/0169056 A1 | 7/2011 | Wey et al. |
| 2011/0181253 A1 | 7/2011 | Isham et al. |
| 2011/0236263 A1 | 9/2011 | Sawada et al. |
| 2011/0262903 A1 | 10/2011 | Davidson et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0299337 A1 | 12/2011 | Parris et al. |
| 2012/0000274 A1 | 1/2012 | Fife et al. |
| 2012/0001056 A1 | 1/2012 | Fife et al. |
| 2012/0001236 A1 | 1/2012 | Fife et al. |
| 2012/0001237 A1 | 1/2012 | Fife et al. |
| 2012/0001615 A1 | 1/2012 | Levine et al. |
| 2012/0001646 A1 | 1/2012 | Bolander et al. |
| 2012/0001779 A1* | 1/2012 | Fife .................. G01N 27/4143 341/101 |
| 2012/0013392 A1 | 1/2012 | Rothberg et al. |
| 2012/0034607 A1 | 2/2012 | Rothberg et al. |
| 2012/0045368 A1 | 2/2012 | Hinz et al. |
| 2012/0055811 A1 | 3/2012 | Rothberg et al. |
| 2012/0055813 A1 | 3/2012 | Rothberg et al. |
| 2012/0056248 A1 | 3/2012 | Fife |
| 2012/0060587 A1 | 3/2012 | Babcock et al. |
| 2012/0067723 A1 | 3/2012 | Rearick et al. |
| 2012/0074956 A1* | 3/2012 | Fife .................. G01N 27/4148 324/612 |
| 2012/0129703 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0154018 A1 | 6/2012 | Sugiura |
| 2012/0161207 A1 | 6/2012 | Homyk et al. |
| 2012/0168307 A1 | 7/2012 | Fife |
| 2012/0173159 A1 | 7/2012 | Davey et al. |
| 2012/0249192 A1 | 10/2012 | Matsushita et al. |
| 2012/0261274 A1 | 10/2012 | Rearick et al. |
| 2012/0286771 A1 | 11/2012 | Rothberg et al. |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329192 A1 | 12/2012 | Bustillo et al. |
| 2013/0001653 A1 | 1/2013 | Milgrew et al. |
| 2013/0009214 A1 | 1/2013 | Bustillo et al. |
| 2013/0056353 A1 | 3/2013 | Nemirovsky et al. |
| 2013/0105868 A1 | 5/2013 | Kalnitsky et al. |
| 2013/0135018 A1 | 5/2013 | Kuo et al. |
| 2013/0210128 A1 | 8/2013 | Rothberg et al. |
| 2013/0210182 A1 | 8/2013 | Rothberg et al. |
| 2013/0210641 A1 | 8/2013 | Rothberg et al. |
| 2013/0217004 A1 | 8/2013 | Rothberg et al. |
| 2013/0217587 A1 | 8/2013 | Rothberg et al. |
| 2013/0218524 A1* | 8/2013 | Faerevaag .............. G01D 21/00 702/189 |
| 2013/0281307 A1 | 10/2013 | Li et al. |
| 2013/0324421 A1 | 12/2013 | Rothberg et al. |
| 2013/0341734 A1 | 12/2013 | Merz |
| 2014/0075237 A1 | 3/2014 | Ware |
| 2014/0080717 A1 | 3/2014 | Li et al. |
| 2014/0148345 A1 | 5/2014 | Li et al. |
| 2014/0234981 A1 | 8/2014 | Zarkesh-Ha et al. |
| 2014/0235452 A1 | 8/2014 | Rothberg et al. |
| 2014/0235463 A1 | 8/2014 | Rothberg et al. |
| 2014/0308752 A1 | 10/2014 | Chang et al. |
| 2014/0364320 A1 | 12/2014 | Rothberg et al. |
| 2015/0097214 A1 | 4/2015 | Chen et al. |
| 2015/0131785 A1* | 5/2015 | Topfer .................. A61B 6/5258 378/98 |
| 2015/0183435 A1* | 7/2015 | Johnson .................. F02N 19/10 701/112 |
| 2016/0178568 A1 | 6/2016 | Cheng et al. |
| 2017/0117137 A1 | 4/2017 | Bang et al. |

FOREIGN PATENT DOCUMENTS

| | | |
|---|---|---|
| DE | 4232532 | 4/1994 |
| DE | 4430811 | 9/1995 |
| DE | 102004044299 | 3/2006 |
| DE | 102008012899 | 9/2009 |
| EP | 1243925 | 9/2002 |
| EP | 1371974 | 12/2003 |
| EP | 1669749 | 6/2006 |
| EP | 1975246 | 3/2007 |
| EP | 1870703 | 12/2007 |
| JP | 558070155 | 4/1983 |
| JP | 562237349 | 10/1987 |
| JP | H02250331 | 10/1990 |
| JP | H02310931 | 12/1990 |
| JP | H05080115 | 4/1993 |
| JP | H10-078827 | 3/1998 |
| JP | 2000-055874 | 2/2000 |
| JP | 2002-221510 | 8/2002 |
| JP | 2002-272463 | 9/2002 |
| JP | 2003-279532 | 10/2003 |
| JP | 2003-322633 | 11/2003 |
| JP | 2005-218310 | 8/2004 |
| JP | 2004-343441 | 12/2004 |
| JP | 2005-515475 | 5/2005 |
| JP | 2006-138846 | 6/2006 |
| JP | 2006-284225 | 10/2006 |
| JP | 2007-243003 | 9/2007 |
| JP | 2008-215974 | 9/2008 |
| KR | 100442838 | 8/2004 |
| KR | 100455283 | 11/2004 |
| TW | 200510714 | 3/2005 |
| TW | 200914857 | 1/2006 |
| TW | 200946904 | 11/2009 |
| WO | WO-1999/019717 | 4/1999 |
| WO | WO-2001047804 | 7/2001 |
| WO | WO-2003073088 | 9/2003 |
| WO | WO-2004017068 | 2/2004 |
| WO | WO-2004040291 | 5/2004 |
| WO | WO-2004048962 | 6/2004 |
| WO | WO-2005015156 | 2/2005 |
| WO | WO-2005054431 | 6/2005 |
| WO | WO-2005062049 | 7/2005 |
| WO | WO-2005084367 | 9/2005 |
| WO | WO-2005090961 | 9/2005 |
| WO | WO-2006005967 | 1/2006 |
| WO | WO-2006022370 | 3/2006 |
| WO | WO-2006056226 | 6/2006 |
| WO | WO-2007002204 | 1/2007 |
| WO | WO-2008058282 | 5/2008 |
| WO | WO-2008107014 | 9/2008 |
| WO | WO-2008133719 | 11/2008 |

(56) References Cited

FOREIGN PATENT DOCUMENTS

| | | |
|---|---|---|
| WO | WO-2009012112 | 1/2009 |
| WO | WO-2009041917 | 4/2009 |
| WO | WO-2010047804 | 4/2010 |
| WO | WO-2010138186 | 12/2010 |
| WO | WO-2010138188 | 12/2010 |
| WO | WO-2012046137 | 4/2012 |
| WO | WO-2012152308 | 11/2012 |
| WO | WO-2014077783 | 5/2014 |

OTHER PUBLICATIONS

Beer et al., "Anion Recognition and Sensing: The State of the Art and Future Perspectives", Angewandte Chemie International Edition, vol. 40, No. 3, 2001, pp. 486-516.

Brenner et al., "Gene expression analysis by massively parallel signature sequencing (MPSS) on microbead arrays", Nature Biotechnology, vol. 18, No. 6, Jun. 2000, pp. 630-634.

Brzozka et al., "Enhanced performance of potassium CHEMFETs by optimization of a polysiloxane membrane", Sensors and Actuators B: Chemical, vol. 18, Nos. 1-3, Mar. 1994, pp. 38-41.

Cobben et al., "Transduction of Selective Recognition of Heavy Metal Ions by Chemically Modified Field Effect Transistors (CHEMFETs)", Journal of the American Chemical Society, vol. 114, No. 26, 1992, pp. 10573-10582.

EP10780935.2, Search Report, dated Jun. 9, 2015.

EP10780935.2, Supplementary Search Report, dated Sep. 30, 2015.

Han et al., "Detection of DNA hybridization by a field-effect transistor with covalently attached catcher molecules", Surface and Interface Analysis, vol. 38, No. 4, Apr. 2006, pp. 176-181.

Ligler et al., "Array biosensor for detection of toxins", Analytical and Bioanalytical Chemistry, vol. 377, No. 3, 2003, pp. 469-477.

Martel et al., "Single-and multi-wall carbon nanotube field-effect transistors", Applied Physics Letters, vol. 73, No. 17, Oct. 1998, pp. 2447-2449.

PCT/US2010/001547, Search Report and Written Opinion, dated Aug. 5, 2010.

PCT/US2012/058996, Search Report and Written Opinion, dated Jan. 22, 2013.

Rowe et al., "An Array Immunosensor for Simultaneous Detection of Clinical Analytes" Analytical Chemistry, vol. 71, No. 2, Jan. 1999, pp. 433-439.

Schoning et al., "Recent advances in biologically sensitive field-effect transistors (BioFETs)", Analyst, vol. 127, No. 9, 2002, pp. 1137-1151.

Schroder, "Oxide and Interface Trapped Charges, Oxide Thickness", Semiconductor Material and Device Characterization, John Wiley & Sons, ISBN: 978-0-471-73906-7, Chapter 6, Feb. 17, 2006, pp. 319-387.

Sia et al., "Microfluidic devices fabricated in poly(dimethylsiloxane) for biological studies", Electrophoresis, vol. 24, No. 21, Nov. 2003, pp. 3563-3576.

Sibbald et al., "A miniature flowthrough cell with a four-function ChemFET integrated circuit for simultaneous measurements of potassium, hydrogen, calcium and sodium ions", Analytica chimica acta., vol. 159, 1984, pp. 47-62.

Unger et al., "Monolithic Microfabricated Valves and Pumps by Multilayer Soft Lithography", Science, vol. 288, No. 5463, Apr. 2000, pp. 113-116.

Ahmadian et al., "Single-nucleotide polymorphism analysis by pyrosequencing", Analytical and Biochemistry, vol. 280, 2000, pp. 103-110.

Akiyama et al., "Ion-Sensitive Field-Effect Transistors with Inorganic Gate Oxide for pH Sensing", IEEE Transactions on Electron Devices, vol. 29, No. 12, 1982, pp. 1936-1941.

AU2011226767, Search Information Statement, dated Oct. 26, 2011, pp. 1-3.

Bandiera et al., "A fully electronic sensor for the measurement of cDNA hybridization kinetics", Biosensors & Bioelectronics, vol. 22, Nos. 9-10, Apr. 15, 2007, 2108-2114.

Barbaro et al., "A Charge-Modulated FET for Detection of Biomolecular Processes: Conception, Modeling, and Simulation", IEEE Transactions on Electron Devices, vol. 53, No. 1, 2006, pp. 158-166.

Barbaro et al., "A CMOS, Fully Integrated Sensor for Electronic Detection of DNA Hybridization", IEEE Electronic Device Letters, vol. 27, No. 7, 2006, pp. 595-597.

Barbaro et al., "Fully electronic DNA hybridization detection by a standard CMOS biochip", Sensors and Actuators B: Chemical, vol. 118, 2006, pp. 41-46.

Bashford et al., "Automated bead-trapping apparatus and control system for single-molecule DNA sequencing", Optics Express, vol. 16, No. 5, Mar. 3, 2008, pp. 3445-3455.

Baumann et al., "Microelectronic sensor system for microphysiological application on living cells", Sensors and Actuators B: Chemical, vol. 55, No. 1, Apr. 1999, pp. 77-89.

Bausells et al., "Ion-sensitive field-effect transistors fabricated in a commercial CMOS technology", Sensors and Actuators B: Chemical, vol. 57, Nos. 1-3, 1999, pp. 56-62.

Bergveld, "ISFET, Theory and Practice", IEEE Sensor Conference, Toronto, Oct. 2003, pp. 1-26.

Bergveld, "Thirty years of ISFETOLOGY What happened in the past 30 years and what may happen in the next 30 years", Sensors and Actuators B: Chemical, vol. 88, No. 1, Jan. 2003, pp. 1-20.

Besselink et al., "ISFET Affinity Sensor", Chapter 12 in Methods in Biotechnology, Affinity Biosensors: Techniques and Protocols, vol. 7, 1998, pp. 173-185.

Bobrov et al., "Chemical sensitivity of an ISFET with Ta2O5 membrane in strong acid and alkaline solutions", Sensors and Actuators B: Chemical, vol. 3, No. 1, Jan. 1991, pp. 75-81.

Bockelmann et al., "Detecting DNA by field effect transistor arrays", Proceedings of the 2006 IFIP International Conference on Very Large Scale Integration, 2006, 164-168.

Bousse et al., "A process for the combined fabrication of ion sensors and CMOS circuits", IEEE Electron Device Letters, vol. 9, No. 1, Jan. 1988, pp. 44-46.

Bousse et al., "Zeta potential measurements of Ta2O5 and SiO2 thin films" Journal of Colloid and Interface Science, vol. 147, No. 1, Nov. 1991, pp. 22-32.

Chan et al., "An Integrated ISFETs Instrumentation System in Standard CMOS Technology", IEEE Journal of Solid-State Circuits, vol. 45, No. 9, Sep. 2010, pp. 1923-1934.

Chen et al., "Silicon-based nanoelectronic field-effect pH sensor with local gate control", Applied Physics Letter, vol. 89, Nov. 2006, pp. 223512-1-223512-3.

Chen et al., "Nanoscale field effect transistor for biomolecular signal amplification", Applied Physics Letter, vol. 91, No. 24, Nov. 2007, pp. 243511-1-243511-3.

Chin et al., "Titanium Nitride Membrane Application to Extended Gate Field Effect Transistor pH Sensor Using VLSI Technology", Japanese Journal of Applied Physics, vol. 40, Part 1, No. 11, Nov. 2001, pp. 6311-6315.

Chou et al., "Simulation of Ta2O5-gate ISFET temperature characteristics", Sensor and Actuators B: Chemical, vol. 71, Nos. 1-2, Nov. 2000, pp. 73-76.

Chou et al., "Letter to the Editor on Simulation of Ta2O5-gate ISFET temperature characteristics", Sensors and Actuators B: Chemical, vol. 80, 2001, pp. 290-291.

Chung et al., "ISFET interface circuit embedded with noise rejection capability", Electronics Letters, vol. 40, No. 18, e-pub, 2 Pages, Sep. 2, 2004, 1115-1116.

Chung et al., "ISFET performance enhancement by using the improved circuit techniques", Sensors and Actuators B: Chemical, vol. 113, No. 1, Jan. 2006, pp. 555-562.

Chung et al., "New ISFET interface circuit design with temperature Compensation", CiteSeerx—URL: http://citeseerx.ist.psu.edu/viewdoc/download?doi=10.1.1.95.2321&rep=rep1&type=pdf, 2006,1.

Chung et al., "New ISFET Interface Circuit Design with Temperature Compensation", Microelectronics Journal, vol. 37, No. 10, Oct. 1, 2006, pp. 1105-1114.

Chung et al., "Temperature compensation electronics for ISFET readout applications", Biomedical Circuits and Systems, IEEE International Workshop Singapore, Dec. 1, 2004, pp. 305-308.

(56) References Cited

OTHER PUBLICATIONS

Dazhong et al., "Research of CMOS Biosensor IC for Extracellular Electrophysiological Signal Recording and pH value Measuring", Solid-State and Integrated-Circuit Technology, 9th International Conference, NJ USA, Oct. 20, 2008, pp. 2557-2560.
Dorf, "The Electrical Engineering Handbook", University of California, Davis, CRC Press, 2 edition, Chapter 3—Linear Circuit Analysis, Jun. 25, 2004, pp. 3-1 to 3-66.
Eastman Kodak Company, "Image Sensor Solutions-Full-Frame CCD Image Sensor Performance Specification", www.physics.csbsju.edu/370/photometry/manuals/kaf-1001e.pdf, Feb. 19, 2001.
Eijkel et al., "Measuring Donnan-related phenomena using a solid-state ion sensor and a concentration-step method", Journal of Membrane Science, vol. 127, May 1997, pp. 203-221.
Eijkel, "Potentiometric detection and characterization of adsorbed protein using stimulus-response measurement techniques", Thesis, Sep. 3, 1955, pp. 1-147; 160-192.
Eltoukhy et al., "A 0.18um CMOS 10-6 lux bioluminescence detection system-on-chip", 2004 IEEE Inti Solid States Conference. Digest of Technical Papers. Session 12, Microsystems/12.3, Feb. 17, 2004. pp. 1-3.
Eltoukhy et al., "A. 0.18-um CMOS Bioluminescence Detection Lab-on-Chip", IEEE Journal of Solid-State Circuits, vol. 41, No. 3, Apr. 2006, pp. 651-662.
EP09798251.6, Extended Search Report, dated Aug. 27, 2013, 6 pages.
EP09822323.3, Extended Search Report, dated May 27, 2015, 8 pages.
EP10780930.3, Search Report, dated Jun. 15, 2015, 3 pages.
EP10857377.5, Search Report, dated Jun. 26, 2015, 3 pages.
EP11801437.2, Extended Search Report, dated Jul. 25, 2013, 10 pages.
EP11801439.8, Extended Search Report, dated Mar. 7, 2014, 9 pages.
EP11804218.3, Extended Search Report, dated Jul. 11, 2013, 3 pages.
EP11827128.7, Search Report, dated Aug. 1, 2013, 5 pages.
EP13161312.7, Extended Search Report, dated Oct. 15, 2013, 8 pages.
EP13163995.7, Extended Search Report, dated Aug. 20, 2013, 6 pages.
EP13164768.7, Extended Search Report, dated Aug. 20, 2013, pages.
EP13174555.6, Extended Search Report, dated Dec. 4, 2013, 8 pages.
EP13174555.6, Search Report, dated Nov. 21, 2013, 5 pages.
EP13177039.8, Search Report, dated Nov. 21, 2013, 9 pages.
EP13177590.0, Search Report, dated Nov. 20, 2013, 5 pages.
EP14152861.2, Search Report, dated Jul. 7, 2014, 5 pages.
EP15170247.9, Search Report, dated Nov. 10, 2015, 4 pages.
EP17167536.6, Search Report, dated Nov. 7, 2017. 1-13.
Eriksson et al., "Pyrosequencing™ Technology at Elevated Temperature" Electrophoresis, vol. 25, No. 1, Jan. 2004, pp. 20-27.
Esfandyarpour et al., "Gate-controlled microfluidic chamber with magnetic bead for DNA sequencing-by-synthesis technology", Proc 5th Intl Conf Nanochannels, Microchannels and Minichannels, Puebla, Mexico, Jun. 18-20, 2007, pp. 1-5.
Eversmann et al., "A 128.times.128 CMOS Biosensor Array for Extracellular Recording of Neural Activity", IEEE J. Solid-State Circ., vol. 38, No. 12, Dec. 12, 2003, pp. 2306-2317.
Faramarzpour et al., "CMOS-Based Active Pixel for Low-Light Level Detection: Analysis and Measurements", IEEE Trans Electron Devices, vol. 54, No. 12, Dec. 2007, pp. 3229-3237.
Finn et al., "Towards an Optimization of FET-Based Bio-Sensors", European Cells and Materials, vol. 4, Sup 2, 2002, pp. 21-23.
Fraden, "Handbook of Modern Sensors-Physics, Designs, and Applications", 17.3.2 CHEMFET Sensors, 1996, pp. 499-501.
Fritz et al., "Electronic detection of DNA by its intrinsic molecular charge", Proceedings of the National Academy of Sciences, vol. 99, No. 22, Oct. 29, 2002, 14142-14146.

Gardner et al., "Enhancing electronic nose performance by sensor selection using a new integer-based genetic algorithm approach", Sensors and Actuators B: Chemical, vol. 106, No. 1, Apr. 2005, pp. 114-121.
GB0811656.8, Search Report, dated Mar. 12, 2010.
GB0811656.8, Search Report, dated Sep. 21, 2009.
GB0811657.6, Search Report, dated Oct. 26, 2009.
Gracia et al., "Test Structures for ISFET Chemical Sensors", IEEE Proceedings of the 1992 International Conference on Microelectronic Test Structures, vol. 5, 1992, pp. 156-159.
Hammond et al., "A System-on-Chip Digital pH Meter for Use in a Wireless Diagnostic Capsule", IEEE Transactions on Biomedical Engineering, vol. 52, No. 4, May 2005, pp. 687-694.
Hammond et al., "Design of a Single-Chip pH Sensor Using a Conventional 0.6-.mu.m CMOS Process", IEEE Sensors Journal, vol. 4, No. 6, 2004, pp. 706-712.
Hammond et al., "Encapsulation of a liquid-sensing microchip using SU-8 photoresist", MicroElectronic Engineering, vols. 73-74, Jun. 2004, pp. 893-897.
Hammond et al., "Genomic sequencing and analysis of a Chinese Hamster ovary cell line using Illumina sequencing technology", BMC Genomics, vol. 12, No. 67, Jan. 2011, pp. 1-8.
Hammond et al., "Performance and system-on-chip integration of an unmodified CMOS ISFET", Sensors and Actuators B: Chemical, vols. 111-112, Nov. 2005, pp. 254-258.
Han "Label-free detection of biomolecules by a field-effect transistor microarray biosensor with bio-functionalized gate surfaces," Masters Dissertation, RWTH Aachen University, 2006, pp. 1-63.
Hanshaw et al., "An indicator displacement system for fluorescent detection of phosphate oxyanions under physiological conditions", Tetrahedron Letters, vol. 45, No. 47, Nov. 15, 2004, pp. 8721-8724.
Hara et al., "Dynamic response of a Ta2O5-gate pH-sensitive field-effect transistor", Sensors Actuators B: Chemical, vol. 32, No. 2, May 1996, pp. 115-119.
Hermon et al., "Miniaturized bio-electronic hybrid for chemical sensing applications", Tech Connect News, Apr. 22, 2008, pp. 1.
Hideshima et al., "Detection of tumor marker in blood serum using antibody-modified field effect transistor with optimized BSA blocking", Sensors and Actuations B: Chemical, vol. 161, No. 1, Jan. 2012, pp. 146-150.
Hijikata et al., "Identification of a Single Nucleotide Polymorphism in the MXA Gene Promoter (T/T at nt-88) Correlated with the Response of Hepatitis C Patients to Interferon", Intervirology, vol. 43, No. 2, 2000, pp. 124-127.
Hizawa et al., "32.times.32 pH Image Sensors for Real Time Observation of Biochemical Phenomena", Transducers & Eurosensors '07, 14th Intl. Conf. on Solid-State, Actuators and Microsystems, Lyon, France, Jun. 10-14, 2007, pp. 1311-1312.
Hizawa, et al., "Sensing Characteristics of Charge Transfer Type pH Sensor by Accumulative Operation", IEEE Sensors, EXCO, Daegu, Korea, Oct. 22-25, 2006, pp. 144-147.
Hizawa et al., "Fabrication of a two-dimensional pH image sensor using a charge transfer technique", Sensors and Actuators B: Chemical, vol. 117, No. 2, Oct. 2006, pp. 509-515.
Ingebrandt et al., "Label-free Detection of DNA using Field-Effect Transistors", Physica status solidi A, vol. 203, No. 14, Nov. 2006, pp. 3399-3411.
Izuru, "Kojien", published by Owanami, Fourth Edition, 1991, 2683.
Jakobson et al., "Low frequency noise and drift in Ion Sensitive Field Effect Transistors", Sensors Actuators B: Chemical, vol. 68, Nos. 1-3, Aug. 2000, pp. 134-139.
Ji et al., "A CMOS contact imager for locating individual cells", IEEE International Symposium on Circuits and Systems, 2006, pp. 3357-3360.
Ji et al., "Contact Imaging: Simulation and Experiment", IEEE Trans Circuits Systems—I: Regular Papers, vol. 54, No. 8, 2007, pp. 1698-1710.
Kim et al., "An FET-type charger sensor for highly sensitive detection of DNA sequence", Biosensors & Bioelectronics, vol. 20, No. 1, Jul. 30, 2004, pp. 69-74.
Klein, "Time effects of ion-sensitive field-effect transistors", Sensors and Actuators, vol. 17, Nos. 1-2, May 1989, pp. 203-208.

(56) References Cited

OTHER PUBLICATIONS

Koch et al., "Protein detection with a novel ISFET-based zeta potential analyzer", Biosensors & Bioelectronics, vol. 14, No. 4, Apr. 1999, pp. 413-421.
Krause et al., "Extended Gate Electrode Arrays for Extracellular Signal Recordings", Sensors and Actuators B: Chemical, vol. 70, Nos. 1-3, Nov. 2000, pp. 101-107.
Kruise et al., "Detection of protein concentrations using a pH-step titration method", Sensors Actuators B: Chemical, vol. 44, Nos. 1-3, Oct. 1997, pp. 297-303.
Leamon et al., "A Massively Parallel PicoTiterPlate Based Platform for Discrete Picoliter-Scale Polymerase Chain Reactions", Electrophoresis, vol. 24, No. 21, Nov. 24, 2003, pp. 3769-3777.
Leamon et al., "Cramming More Sequencing Reactions onto Microreactor Chips", Chemical Reviews, vol. 107, No. 8, Aug. 2007, pp. 3367-3376.
Lee et al. "An Enhanced Glucose Biosensor Using Charge Transfer Techniques" Biosensors & Bioelectronics, vol. 24, No. 4, Dec. 2008, pp. 650-656.
Lee et al., "Ion-sensitive Field-Effect Transistor for Biological Sensing", Sensors, vol. 9, No. 9, 2009, pp. 7111-7131.
Li et al., "Sequence-Specific Label-Free DNA Sensors based on Silico Nanowires", Nano Letters, vol. 4, No. 2, Jan. 2004, pp. 245-247.
Lin et al., "Practicing the Novolac deep-UV portable conformable masking technique", Journal of Vacuum Science and Technology, vol. 19, No. 4, 1981, 1313-1319.
Liu et al., "An ISFET based sensing array with sensor offset compensation and pH sensitivity enhancement", IEEE International Symposium on Circuits and Systems, ISBN:978-1-4244-5308-5, Jun. 2, 2010, pp. 2283-2286.
Lohrengel et al., "A new microcell or microreactor for material surface investigations at large current densities", Electrochimica Acta, vol. 49, Nos. 17-18, Jul. 2004, pp. 2863-2870.
Lui et al., "A Test Chip for ISFET/CMNOS Technology Development", IEEE International Conference on Microelectronic Test Structures, vol. 9, 1996, pp. 123-128.
Maki et al., "Nanowire-transistor based ultra-sensitive DNA methylation detection", Biosensors & Bioelectronics, vol. 23, No. 6, Jan. 2008, pp. 780-787.
Margulies et al., "Genome sequencing in microfabricated high-density picolitre reactors", Nature, vol. 437, No. 7057, Sep. 15, 2005, pp. 376-380. (Epub Jul. 31, 2005.).
Marshall et al., "DNA chips: an array of possibilities", Nature Biotechnology, vol. 16, No. 1, Jan. 1998, pp. 27-31.
Martinoia et al., "A behavioral macromodel of the ISFET in SPICE", Sensors and Actuators B: Chemical, vol. 62, No. 3, Mar. 2000, pp. 182-189.
Martinoia et al., "Development of ISFET Array-Based Microsystems for Bioelectrochemical measurements of cell populations", Biosensors & Bioelectronics, vol. 16, Nos. 9-12, Dec. 2001, pp. 1043-1050.
Matsuo et al. "Charge Transfer Type pH Sensor with Super High Sensitivity" 14th International Conference on Solid-State Sensors Actuators and Microsystems, France, Jun. 10-14, 2007, pp. 1881-1884.
Matula, "Electrical Resistivity of Copper, Gold, Palladium, and Silver", Journal of Physical and Chemical Reference Data, vol. 8, No. 4, 1979, pp. 1147-1298.
Medoro et al., "A Lab-on-Chip for Cell Detection and Manipulation", IEEE Sensors Journal, vol. 3, No. 3, 2003, pp. 317-325.
Meyburg et al., "N-Channel field-effect transistors with floating gates for extracellular recordings", Biosensors and Bioelectronics, vol. 21, No. 7, Jan. 15, 2006, pp. 1037-1044.
Milgrew et al., "A 16×16 CMOS proton camera array for direct extracellular imaging of hydrogen-ion activity", IEEE Inti Solid-State Circuits Conference, Session 32:24, 2008, pp. 590-591,638.
Milgrew et al., "A large transistor-based sensor array chip for direct extracellular imaging", Sensors and Actuators B: Chemical, vols. 111-112, Nov. 2005, pp. 347-353.
Milgrew et al., "A Proton Camera Array Technology for Direct Extracellular Ion Imaging", IEEE International Symposium on Industrial Electronics, 2008, 2051-2055.
Milgrew et al., "Matching the transconductance characteristics of CMOS ISFET arrays by removing trapped charge", IEEE Transactions on Electronic Devices, vol. 55, No. 4, 2008, pp. 1074-1079.
Milgrew et al., "Microsensor Array Technology for Direct Extracellular Imaging", Dept Electronic and EE, University of Glasgow, Apr. 5, 2006, pp. 1-23.
Milgrew et al., "The Development of Scalable Sensor Arrays Using Standard CMOS Technology", Sensors and Actuators B: Chemical, vol. 103, Nos. 1-2, Sep. 2004, pp. 37-42.
Milgrew et al., "The fabrication of scalable multi-sensor arrays using standard CMOS technology", IEEE Custom Integrated Circuits Conference, 2003, pp. 513-516.
Miyahara et al., "Biochip Using Micromachining Technology", Journal of Institute of Electrostatics, Japan, vol. 27, No. 6, 2003, pp. 268-272.
Miyahara et al., "Direct Transduction of Primer Extension into Electrical Signal Using Genetic Field Effect Transistor", Micro Total Analysis Systems, vol. 1, Proceedings of UTAS 2004, 8th International Conference on Miniaturized Systems for Chemistry and Life Sciences, Malmo, Sweden, Sep. 26-30, 2004, pp. 303-305.
Miyahara et al., "Potentiometric Detection of DNA Molecules Using Field Effect Transistor", The Japan Society of Applied Physics, No. 3, 2003, pp. 1180, 30A-S2.
Morgenshtein et al., "Wheatstone-Bridge readout interface for ISFET/REFET applications", Sensors and Actuators B: Chemical, vol. 98, No. 1, Mar. 2004, pp. 18-27.
Moriizumi, "Biosensors", Oyo Buturi (monthly publication of the Japan Society of Applied Physics), vol. 54, No. 2, Feb. 10, 1985, pp. 98-114.
Naidu et al., "Introduction to Electrical Engineering", Chapter 1—Fundamental Concepts of Electricity, McGraw Hill Education (India) Private Limited, 1995, pp. 1-10.
Nakazato, "An Integrated ISFET Sensor Array", Sensors, Nov. 2009, vol. 9, No. 11, ISSN:1424-8220, [online], Internet, URL, http://www.mdpi.com/1424-8220/9/11/8831/pdf, Nov. 2009, pp. 8831-8851.
Nakazato et al., "28p-Y-7 ISFET sensor array integrated circuits based on the standard CMOS process", The 55th annual meeting of the Japan Society of Applied Physics, Book of Abstracts, ISBN:978-4-903968-44-5, Mar. 27, 2008, p. 70.
Neaman, "Electronic Circuit Analysis and Design", McGraw Hill Higher Education, 2nd Edition, Chapter 6—Basic FET Amplifiers, (reference will be uploaded in 2 parts due to size) part 1 of 2, Dec. 1, 2000, pp. 313-345.
Neaman, "Electronic Circuit Analysis and Design", McGraw Hill Higher Education, 2nd Edition, Chapter 6—Basic FET Amplifiers, (reference will be uploaded in 2 parts due to size) part 2 of 2, Dec. 1, 2000, pp. 346-381.
Nishiguchi et al., "Si nanowire ion-sensitive field-effect transistors with a shared floating gate", Applied Physics Letters, vol. 94, Apr. 2009, pp. 163106-1 to 163106-3.
[No Author Listed], "ISFET Wikipedia article", Wikipedia, Last modified Nov. 7, 2006.
Nyren et al., "Enzymatic Method for Continuous Monitoring of Inorganic Pyrophosphate Synthesis", Analytical Biochemistry, vol. 151, No. 2, Dec. 1985, pp. 504-509.
Oelßner et al., "Encapsulation of ISFET sensor chips", Sensors Actuators B: Chemical, vol. 105, No. 1, Feb. 2005, pp. 104-117.
Oelßner et al., "Investigation of the dynamic response behavior of ISFET pH sensors by means of laser Doppler velocimetry (LDV)", Sensors and Actuators B: Chemical, vol. 27, Nos. 1-3, Jun. 1995, pp. 345-348.
Offenhausser et al., "Field-Effect transistor array for monitoring electrical activity from mammalian neurons in culture", Biosensors & Bioelectronics, vol. 12, No. 8, Jan. 1997, pp. 819-826.
Ohno et al., "Electrolyte-Gated Graphene Field-Effect Transistors for Detecting pH and Protein Adsorption", Nano Letters, vol. 9, No. 9, Jul. 28, 2009, pp. 3318-3322.

(56) References Cited

OTHER PUBLICATIONS

Palan et al., "New ISFET sensor interface circuit for biomedical applications", Sensors and Actuators B: Chemical, vol. 57, Nos. 1-3, Sep. 1999, pp. 63-68.
Park et al., "ISFET glucose sensor system with fast recovery characteristics by employing electrolysis", Sensors and Actuators B: Chemical, vol. 83, Nos. 1-3, Mar. 15, 2002, pp. 90-97.
Patolsky et al., "Nanowire-Based Biosensors", Analytical Chemistry, vol. 78, No. 13, Jul. 1, 2006, pp. 4261-4269.
PCT/JP2005/001987, Search Report, dated Apr. 5, 2005.
PCT/JP2005/015522, Preliminary Report on Patentability, dated Mar. 19, 2007.
PCT/JP2005/015522, Search Report, dated Sep. 27, 2005.
PCT/US2007/025721, Declaration of Non-Establishment of International Search Report, dated Jul. 15.
PCT/US2007/025721, Preliminary Report and Written Opinion on Patentability, dated Jun. 16, 2009.
PCT/US2007/025721 Written Opinion dated Jun. 16, 2009.
PCT/US2009/003766, International Search Report and Written Opinion, dated Apr. 8, 2010.
PCT/US2009/003766, Preliminary Report on Patentability, dated Jan. 5, 2011.
PCT/US2009/003797, Search Report and Written Opinion, dated Mar. 12, 2010.
PCT/US2009/005745, Preliminary Report on Patentability, dated Apr. 26, 2011.
PCT/US2009/005745, Search Report and Written Opinion, dated Dec. 11, 2009.
PCT/US2010/001543, Preliminary Report on Patentability, dated Nov. 29, 2011.
PCT/US2010/001543, Search Report and Written Opinion, dated Oct. 13, 2010.
PCT/US2010/001553, Preliminary Report on Patentability, dated Dec. 8, 2011.
PCT/US2010/001553, Search Report and Written Opinion, dated Jul. 28, 2010.
PCT/US2010/048835, Preliminary Report on Patentability, dated Mar. 19, 2013.
PCT/US2010/048835, Search Report and Written Opinion, dated Dec. 16, 2010.
PCT/US2011/042655, Search Report and Written Opinion, dated Oct. 21, 2011.
PCT/US2011/042660, Search Report, dated Nov. 2, 2011.
PCT/US2011/042665, Search Report, dated Nov. 2, 2011.
PCT/US2011/042668, Search Report, dated Oct. 28, 2011.
PCT/US2011/042668, Preliminary Report on Patentability, dated Mar. 26, 2013.
PCT/US2011/042669, Search Report and Written Opinion, dated Jan. 9, 2012.
PCT/US2011/042683, Preliminary Report on Patentability, dated Jun. 4, 2013.
PCT/US2011/042683, Search Report and Written Opinion, dated Feb. 16, 2012.
PCT/US2012/071471, Preliminary Report on Patentability, dated Jun. 24, 2014.
PCT/US2012/071471, Search Report and Written Opinion, dated Apr. 24, 2013.
PCT/US2012/071482, Preliminary Report on Patentability, dated Jun. 24, 2014.
PCT/US2012/071482, Search Report and Written Opinion, dated May 23, 2013.
PCT/US2013/022129, Preliminary Report on Patentability, dated Jul. 22, 2014.
PCT/US2013/022129, Search Report and Written Opinion, dated Aug. 9, 2013.
PCT/US2013/022140, Preliminary Report on Patentability, dated Jul. 22, 2014.
PCT/US2013/022140, Search Report and Written Opinion, dated May 2, 2013.
PCT/US2014/020887, Preliminary Report, dated Sep. 15, 2015, 8 pages.
PCT/US2014/020887, Search Report and Written Opinion, dated May 30, 2014.
PCT/US2014/020892, Search Report and Written Opinion, dated Jun. 3, 2014.
PCT/US2014/040923, Search Report and Written Opinion, dated Sep. 1, 2014.
PCT/US2015/006623, international Preliminary Report on Patentability, dated Jun. 29, 2017, 1-13.
PCT/US2015/066023, Search Report and Written Opinion of, dated Mar. 14, 2016.
PCT/US2015/066023, International Preliminary Report on Patentability, dated Jun. 20, 2017.
PCT/US2015/066052, Preliminary Report on Patentability, dated Jun. 29, 2017.
PCT/US2015/066052, Search Report and Written Opinion, dated Apr. 7, 2016.
PCT/US2015/066110, International Preliminary Report on Patentability, dated Jun. 20, 2017, 1-8.
PCT/US2015/066110, Search Report and Written Opinion, dated Mar. 17, 2016.
Poghossian et al., "Functional testing and characterization of ISFETs on wafer level by means of a micro-droplet cell", Sensors, vol. 6, No. 4, Apr. 2006, pp. 397-404.
Pollack et al., "Genome-wide analysis of DNA copy-number changes using cDNA microarrays", Nature Genetics, vol. 23, No. 1, Sep. 1999, pp. 41-46.
Pourmand et al., "Direct electrical detection of DNA synthesis", Proceedings of the National Academy of Sciences, vol. 103, No. 17, Apr. 2006, 6466-6470.
Pouthas et al., "Spatially resolved electronic detection of biopolymers", Physical Review, vol. 70, No. 3, Sep. 2004, pp. 031906-1-031906-8.
Premanode et al., "A composite ISFET readout circuit employing current feedback", Sensors Actuators B: Chemical, vol. 127, No. 2, Nov. 2007, pp. 486-490.
Premanode et al., "A novel, low power biosensor for real time monitoring of creatinine and urea in peritoneal dialysis", Sensors and Actuators B: Chemical, vol. 120, No. 2, Jan. 2007, pp. 732-735.
Premanode et al., "Drift Reduction in Ion-Sensitive FETs using correlated double sampling", Electronics Letters, vol. 43, No. 16, Aug. 2, 2007, pp. 857-859.
Premanode et al., "Ultra-low power precision ISFET readout using global current feedback", Electronic Letters, vol. 42, No. 22, Oct. 26, 2006, 1264-1265.
Purushothaman et al., "Protons and single nucleotide polymorphism detection: A simple use for the Ion Sensitive Field Effect Transistor", Sensors and Actuators B: Chemical, vol. 114, No. 2, Apr. 2006, pp. 964-968.
Purushothaman et al., "Towards Fast Solid State DNA Sequencing", IEEE ISCAS Proceedings, Circuits and Systems, vol. 4, 2002, pp. IV-169-IV-172.
Rodriguez-Villegas, "Solution to trapped charge in FGMOS transistors", Electronics Letters, vol. 39, No. 19, Oct. 2003, pp. 1416-1417.
Ronaghi et al., "A Sequencing Method Based on Real-Time Pyrophosphate", Science, vol. 281, No. 5375, Jul. 1998, pp. 363-365.
Rothberg et al., "An integrated semiconductor device enabling non-optical genome sequencing", Nature, vol. 475, No. 7356, Jul. 21, 2011, pp. 348-352.
Sakata et al., "Cell-based field effect devices for cell adhesion analysis", Intl. Conf. on Microtechnologies in Medicine and Biology, May 9-12, 2006, Okinawa, Japan, 2006, pp. 177-179.
Sakata et al., "Detection of DNA recognition events using multi-well field effect transistor", Biosensors & Bioelectronics, vol. 21, 2005, pp. 827-832.
Sakata et al., "Detection sensitivity of genetic field effect transistor combined with charged nanoparticle-DNA conjugate", Intl. Conf. on Microtechnologies in Medicine and Biology, May 9-12, 2005, Okinawa, Japan, 2006, pp. 97-100.
Sakata et al., "Direct detection of single nucleotide polymorphism using genetic field effect transistor", International Microprocesses

(56) References Cited

OTHER PUBLICATIONS and Nanotechnology Conference. Oct. 26-29, 2004. Osaka, Japan. Digest of Papers Microprocesses and Nanotechnology 2004. pp. 226-227.
Sakata et al., "Direct Detection of Single-Base Extension Reaction Using Genetic Field Effect Transistor", Proc. of 3rd Ann. Intl. IEEE EMBS Special Topic Conf. on Microtechnologies in Medicine and Biology, Kahuku, Oahu, HI, May 12-15, 2005, pp. 219-222.
Sakata et al., "Direct transduction of allele-specific primer extension into electrical signal using genetic field effect transistor", Biosensors & Bioelectronics, vol. 22, 2007, pp. 1311-1316.
Sakata et al., "DNA Analysis Chip Based on Field-Effect Transistors", Japanese Journal of Applied Physics, vol. 44, No. 4B, 2005, pp. 2854-2859.
Sakata et al., "DNA Sequencing Based on Intrinsic Molecular Charges", Angewandte Chemie International, vol. 118, 2006, pp. 2283-2286.
Sakata et al., "DNA Sequencing Based on Intrinsic Molecular Charges", Angewandte Chemie International, vol. 45, No. 14, Mar. 27, 2006, pp. 2225-2228.
Sakata et al, "DNA Sequencing Using Genetic Field Effect Transistor", 13th International Conference on Solid-State sensors, Actuators and Microsystems, vol. 2, Jun. 5-9, 2005, Seoul, Korea, pp. 1676-1679.
Sakata et al., "Immobilization of oligonucleotide probes on Si3N4 surface and its application to genetic field effect transistor", Materials Science and Engineering: C, vol. 24, Nos. 6-8, Dec. 2004, pp. 827-832.
Sakata et al., "Potential Behavior of Biochemically Modified Gold Electrode for Extended-Gate Field-Effect Transistor", Japanese Journal of Applied Physics, vol. 44, Part 1, No. 4S, Apr. 2005, pp. 2860-2863.
Sakata et al., "Potential response of genetic field effect transistor to charged nanoparticle-DNA conjugate", International Microprocesses and Nanotechnology Conference. Oct. 25-28, 2005. Tokyo, Japan. Digest of Papers Microprocesses and Nanotechnology 2005. pp. 42-43.
Sakata et al., "Potentiometric Detection of Allele Specific Oligonucleotide Hybridization Using Genetic Field Effect Transistor", Micro Total Analysis Systems, vol. 1,8th Intl. Conf. On Miniaturized Systems for Chemistry and Life Sciences, Sep. 26-30, 2004, Malmo, Sweden, pp. 300-302.
Sakata et al., "Potentiometric Detection of DNA Molecules Hybridization Using Gene Field Effect Transistor and Intercalator", Materials Research Society Symposium Proceedings, vol. 782, Micro- and Nanosystems, Boston, Massachusetts, Jan. 2003, pp. 393-398.
Sakata et al., "Potentiometric Detection of DNA Using Genetic Transistor", Denki Gakkai Kenkyukai Shiryo Chemical Sensor Kenkyukai, CHS-03-51-55, 2003, pp. 1-5.
Sakata et al., "Potentiometric Detection of Single Nucleotide Polymorphism by Using a Genetic Field-effect transistor", ChemBioChem, vol. 6, No. 4, Apr. 2005, pp. 703-710.
Sakurai et al., "Real-Time Monitoring of DNA Polymerase Reactions by a Micro ISFET pH Sensor", Analytical Chemistry, vol. 64, No. 17, Sep. 1992, pp. 1996-1997.
Salama, "CMOS luminescence detection lab-on-chip: modeling, design, and characterization", Thesis, Presented at Stanford University, 2005, pp. ii-78.
Salama, "Modeling and simulation of luminescence detection platforms", Biosensors & Bioelectronics, vol. 19, No. 11, Jun. 15, 2004, pp. 1377-1386.
Sawada et al., "A novel fused sensor for photo- and ion-sensing", Sensors and Actuators B: Chemical, vol. 106, No. 2, May 2005, pp. 614-618.
Sawada et al., "Highly sensitive ion sensors using charge transfer technique", Sensors and Actuators B: Chemical, vol. 98, No. 1, Mar. 2004, pp. 69-72.
Schasfoort et al., "A new approach to immunoFET operation", Biosensors & Bioelectronics, vol. 5, No. 2, 1990, pp. 103-124.
Schasfoort et al., "Field-effect flow control for microfabricated fluidic networks", Science, vol. 286. No. 5441, Oct. 29, 1999, pp. 942-945.
Schoning et al., "Bio FEDs (Field-Effect Devices): State-of-the-Art and New Directions", Electroanalysis, vol. 18, Nos. 19-20, Sep. 2006, pp. 1893-1900.
Seong-Jin et al. "Label-Free CMOS DNA Quantification With On-Chip Noise Reduction Schemes" Solid-State Sensors, Actuators and Microsystems Conference, IEEE, Jun. 10, 2013, pp. 947-950.
SG200903992-6, Search and Examination Report, dated Jan. 20, 2011, 12.
Shah, "Microfabrication of a parellelrray DNA pyrosequencing chip", NNIN REU Research Accomplishments, 2005, pp. 130-131.
Shepherd et al., "A biochemical translinear principle with weak inversion ISFETs", IEEE Trans Circuits Syst—I, vol. 52, No. 12, Dec. 2005, pp. 2614-2619.
Shepherd et al., "A novel voltage-clamped CMOS ISFET sensor interface", IEEE, 2007, pp. 3331-3334.
Shepherd et al., "Towards direct biochemical analysis with weak inversion ISFETS", Intl Workshop on Biomedical, 2004, S1.5-5-S1.5-8.
Shepherd et al., "Weak inversion ISFETs for ultra-low power biochemical sensing and real-time analysis", Sensors Actuators B, vol. 107, 2005, pp. 468-473.
Shi et al., "Radical Capillary Array Electrophoresis Microplace and Scanner for High-Performance Nucleic Acid Analysis", Analytical Chemistry, vol. 71, No. 23, 1999, pp. 5354-5361.
Simonian et al., "FET based biosensors for the direct detection of organophosphate neurotoxins", Electroanalysis, vol. 16, No. 22, 2004, pp. 1896-1906.
Souteyrand et al., "Direct detection of the hybridization of synthetic homo-oligomer DNA sequences by field effect", Journal of Physical Chemistry B, vol. 101, No. 15, 1997, pp. 2980-2985.
Starodub et al., "Immunosensor for the determination of the herbicide simazine based on an ion-selective field-effect transistor", Analytica Chimica Acta, vol. 424, No. 1, Nov. 2000, pp. 37-43.
Takenaka et al., "DNA Sensing on a DNA Probe-Modified Electrode Using Ferrocenylnaphthalene Dimide as the Electrochemically Active Ligand", Analytical Chemistry, vol. 72. No. 6, 2000, pp. 1334-1341.
Temes et al., "A Tutorial Discussion of the Oversampling Method for A/D and D/A Conversion", IEEE International Symposium on Circuits and Systems, vols. 2 of 4, 1990, 5 pages.
Terada et al., "Further Study of Vth-Mismatch Evaluation Circuit", f IEEE Int. Conference on Microelectronic Test Structures, vol. 17, Mar. 22, 2004, 155-159.
Thewes et al., "CMOS-based Biosensor Arrays", Proceedings of the Design, Automation and Test in Europe Conference and Exhibition, 2005, 2 pages.
Tokuda et al., "A CMOS image sensor with optical and potential dual imaging function for on-chip bioscientific applications", Sensors and Actuators A: Physical, vol. 125, No. 2, Jan. 2006, 273-280.
Tomaszewski et al., "Electrical characterization of ISFETs", Journal of Telecommunications and Information Technology, Mar. 2007, pp. 55-60.
Toumazou et al., "Using transistors to linearise biochemistry," Electronics Letters, vol. 43, No. 2, Jan. 18, 2007, 3 pages.
Truman et al. "Monitoring liquid transport and chemical composition in lab on a chip systems using ion sensitive FET devices", Lab on a Chip, vol. 6, No. 9, Jul. 2006, pp. 1220-1228.
Unknown, "OV5640 Datasheet Product Specification", 1/4" color CMOS QSXGA (5 megapixel) image sensor with OmniBSI technology. May 1, 2011, p. 1, line 9 and pp. 2-7, paragraph 1.
Uslu et al., "Labelfree fully electronic nucleic acid detection system based on a field-effect transistor device", Biosensors and Bioelectronics, vol. 19. No. 12, Jul. 2004, pp. 1723-1731.
Van Der Schoot et al., "The Use of a Multi-ISFET Sensor Fabricated in a Single Substrate", Sensors and Actuators, vol. 12, No. 4, Nov.-Dec. 1987, pp. 463-468.
Van Der Wouden et al., "Directional flow induced by synchronized longitudinal and zeta-potential controlling AC-electrical fields", Lab Chip, vol. 6, No. 10, Oct. 2006, pp. 1300-1305.

(56) References Cited

OTHER PUBLICATIONS

Van Hal et al., "A general model to describe the electrostatic potential at electrolyte oxide interfaces", Advances in Colloid and Interface Science, vol. 69, Nos. 1-3, Dec. 1996, pp. 31-62.
Van Kerkhof, "Development of an ISFET based heparin sensor using the ion-step measuring method", Biosensors & Bioelectronics, vol. 8, Nos. 9-10, 1993, pp. 463-472.
Van Kerkhof et al., "ISFET Responses on a stepwise change in electrolyte concentration at constant pH", Sensors Actuators B: Chemical, vol. 18-19, Mar. 1994, pp. 56-59.
Van Kerkhof et al., "The development of an ISFET-based heparin sensor," Thesis 1994. Published Aug. 10, 1965.
Van Kerkhof et al., "The ISFET based heparin sensor with a monolayer of protamine as affinity ligand", Biosensors & Bioelectronics, vol. 10, Nos. 3-4, 1995, pp. 269-282.
Vardalas, "Twists and Turns in the Development of the Transistor", IEEE-USA Today's Engineer Online, May 2003, 6 pages.
Voigt et al., "Diamond-like carbon-gate pH-ISFET", Sensors and Actuators B: Chemical, vol. 44, Nos. 1-3, Oct. 1997, pp. 441-445.
Wagner et al., All-in-one solid-state device based on a light-addressable potentiometric sensor platform, Sensors and Actuators B: Chemical, vol. 117, No. 2, Oct. 2006, pp. 472-479.
Wang et al., "Label-free detection of small-molecule-protein interactions by using nanowire nanosensors", Proceedings of the National Academy of Sciences, vol. 102, No. 9, Mar. 2005, 3208-3212.
Wilhelm et al., "pH Sensor Based on Differential Measurements on One pH-FET Chip", Sensors and Actuators B: Chemical, vol. 4, Nos. 1-2, May 1991, pp. 145-149.
Woias et al., "Slow pH response effects of silicon nitride ISFET sensors", Sensors and Actuators B: Chemical, vol. 48, Nos. 1-3, May 1998, pp. 501-504.
Woias, "Modelling the short time response of ISFET sensors", Sensors and Actuators B: Chemical, vol. 24, Nos. 1-3, Mar. 1995, pp. 211-217.
Wood et al., "Base composition-independent hybridization in tetramethylammonium chloride: a method for oligonucleotide screening of highly complex gene libraries", Proceedings of the National Academy of Sciences, vol. 82, No. 6, Mar. 1985, 1585-1588.
Wu et al., "DNA and protein microarray printing on silicon nitride waveguide surfaces", Biosensors & Bioelectronics, vol. 21, No. 7, Jan. 2006, pp. 1252-1263.
Xu et al., "Analytical Aspects of FET-Based Biosensors", Frontiers in Bioscience, vol. 10, Jan. 2005, pp. 420-430.
Yeow et al., "A very large integrated pH-ISFET sensor array chip compatible with standard CMOS processes", Sensor and Actuators B: Chemical, vol. 44, Nos. 1-3, Oct. 1997, pp. 434-440.
Yoshida et al., "Development of a Wide Range pH Sensor based on Electrolyte-Insulator-Semiconductor Structure with Corrosion-Resistant $Al_2O_3$—$Ta_2O_5$ and $Al_2O_3$—$ZrO_2$", Journal of the Electrochemical Society, vol. 151, No. 3, 2004, pp. H53-H58.
Yuqing et al., "Ion sensitive field effect transducer-based biosensors", Biotechnology Advances, vol. 21, No. 6, Sep. 2003, pp. 527-534.
Zhang et al., "32-Channel Full Customized CMOS Biosensor Chip for Extracellular neural Signal Recording", Proc. of the 2nd Intl. IEEE EMBs Conf. on Neural Engineering, Arlington, Virginia, Mar. 16-19, 2005, pp. v-viii.
Zhao et al., "Floating-Gate Ion Sensitive Field-Effect Transistor for Chemical and Biological Sensing", MRS Proceedings, vol. 828, 2005, pp. 349-354.
Zhou et al., "Quantitative detection of single nucleotide polymorphisms for a pooled sample by a bioluminometric assay coupled with modified primer extension reactions (BAMPER)", Nucleic Acids Research, vol. 29, No. 19, Oct. 2001, (e93), 1-11.

* cited by examiner

HIGH DATA RATE INTEGRATED CIRCUIT WITH POWER MANAGEMENT

CROSS-REFERENCE TO RELATED APPLICATIONS

This application is a divisional of U.S. application Ser. No. 14/965,568 filed Dec. 20, 2015, which claims the benefit of U.S. Provisional Application No. 62/093,611 filed Dec. 18, 2014. The entire contents of all applications referenced in this section are incorporated by reference herein, each in their entirety.

BACKGROUND

Field of the Invention

This disclosure, in general, relates to thermal and power management of integrated circuit sensors operating at high data rates, such as used in DNA sequencing technologies, and to systems utilizing such sensors.

Description of Related Art

A variety of types of sensors have been used in the detection of chemical and/or biological processes. One type is a chemically-sensitive field effect transistor (chemFET). A chemFET includes a gate, a source, a drain separated by a channel region, and a sensitive area, such as a surface on the gate adapted for contact with a fluid, coupled to the channel region. The operation of the chemFET is based on the modulation of channel conductance caused by changes, such as changes in voltage, at the sensitive area which can be due to a chemical and/or biological reaction occurring in the fluid, for example. The modulation of the channel conductance can be sensed to detect and/or determine characteristics of the chemical and/or biological reaction that cause changes at the sensitive area. One way to measure the channel conductance is to apply appropriate bias voltages to the source and drain, and measure a resulting current flowing through the chemFET. A method of measuring channel conductance can include driving a known current through the chemFET and measuring a resulting voltage at the source or drain.

An ion-sensitive field effect transistor (ISFET) is a type of chemFET that includes an ion-sensitive layer at the sensitive area. The presence of ions in a fluid containing an analyte alters the surface potential at the interface between the ion-sensitive layer and the analyte fluid which can be due to the protonation or deprotonation of surface charge groups caused by the ions present in the fluid (i.e. an analyte solution). The change in surface potential at the sensitive area of the ISFET affects the gate voltage of the device, and thereby channel conductance, which change can be measured to indicate the presence and/or concentration of ions within the solution. Arrays of ISFETs can be used for monitoring chemical and/or biological reactions, such as DNA sequencing reactions based on the detection of ions present, generated, or used during the reactions. (See, for example, U.S. Pat. No. 7,948,015 to Rothberg et al., filed Dec. 14, 2007, which is incorporated by reference herein in its entirety.) More generally, large arrays of chemFETs or other types of sensors and detectors can be employed to detect and measure static and/or dynamic amounts or concentrations of a variety of analytes in a variety of processes. For example, the processes can be chemical and/or biological reactions, cell or tissue cultures or monitoring neural activity, nucleic acid sequencing, etc.

It may be desirable to provide a power and temperature management technology supporting very high data rate DNA sequencing systems, and other systems involving complex electrodynamic and thermodynamic interfaces to integrated circuits.

SUMMARY

Technology is described for managing power and temperature suitable for use with complex DNA sequencing technologies, and other technologies employing complex sensor arrays.

One aspect of the technology comprises a sensor system. The sensor system includes a sensor array that can include rows and columns of sensors. A reactant flow cell may be in contact with the sensor array, and may be configured to apply a sequence of alternating flows of reactant solutions during active intervals and flows of wash solutions during wash intervals to the sensor array. Bias circuitry can apply bias arrangements to the sensor array to produce sensor data. Peripheral circuitry may be coupled to the bias circuitry to produce streams of data from the sensor array. The peripheral circuitry may be configured to have an active mode and an idle mode. Logic may be provided to switch the peripheral circuitry between the active mode and idle mode to control power consumption. During the idle mode, operational readiness of the sensor array may be maintained, while reducing power consumption. Thus, electrical circuitry supporting electro-fluidic conditions of the sensor array remain active during the idle mode. Likewise, transmission of the streams of data may be maintained, to maintain communication links during the idle mode to maintain operational readiness.

According to another aspect, the temperature sensors provided which senses a temperature that correlates with temperature of the sensor array. In this example, the logic can include the feedback circuit responsive to the temperature sensor to switch between the active mode and the idle mode to maintain the temperature within an operating range.

In one architecture described herein, the peripheral circuitry includes conversion circuitry responsive to configuration parameters to convert the sensor data into a plurality of streams of data, and a plurality of transmitters configured to receive the corresponding streams of data from the plurality of streams from the conversion circuitry and transmit the data to corresponding receivers. Also, a sequencer may be included which operates the bias circuitry to produce frames of sensor data at a frame rate, operates the conversion circuitry to convert the sensor data at a frame rate, and operates the transmitters to transmit the streams of data at the frame rate. In this configuration, the logic may be configured to apply a first set of one or more configuration parameters to the conversion circuitry in the active mode, and a second set of one or more configuration parameters to the conversion circuitry in idle mode. Also, the logic may be configured to apply a third set of one or more configuration parameters to the bias circuitry in the active mode, and a fourth set of one or more configuration parameters to the bias circuitry in idle mode.

In one control operation described herein, the peripheral circuitry operates in the active mode for a first number of frames in a time interval overlapping with the active interval, and for a second number of frames in the idle mode in a time interval overlapping with an immediately following wash interval. Logic can adjust the first and second numbers of frames to control power consumption and temperature of the device.

An integrated circuit sensor for use in a sensor system is described as well.

A method for operating a sensor system in order to conserve power and control temperature is described as well.

Other aspects and advantages of the technology described herein may be seen on review of the drawings, the detailed description and the claims, which follow.

DETAILED DESCRIPTION

A detailed description of embodiments of the sensor technology and components thereof, is provided with reference to the FIGS. 1-17.

Figure 1:
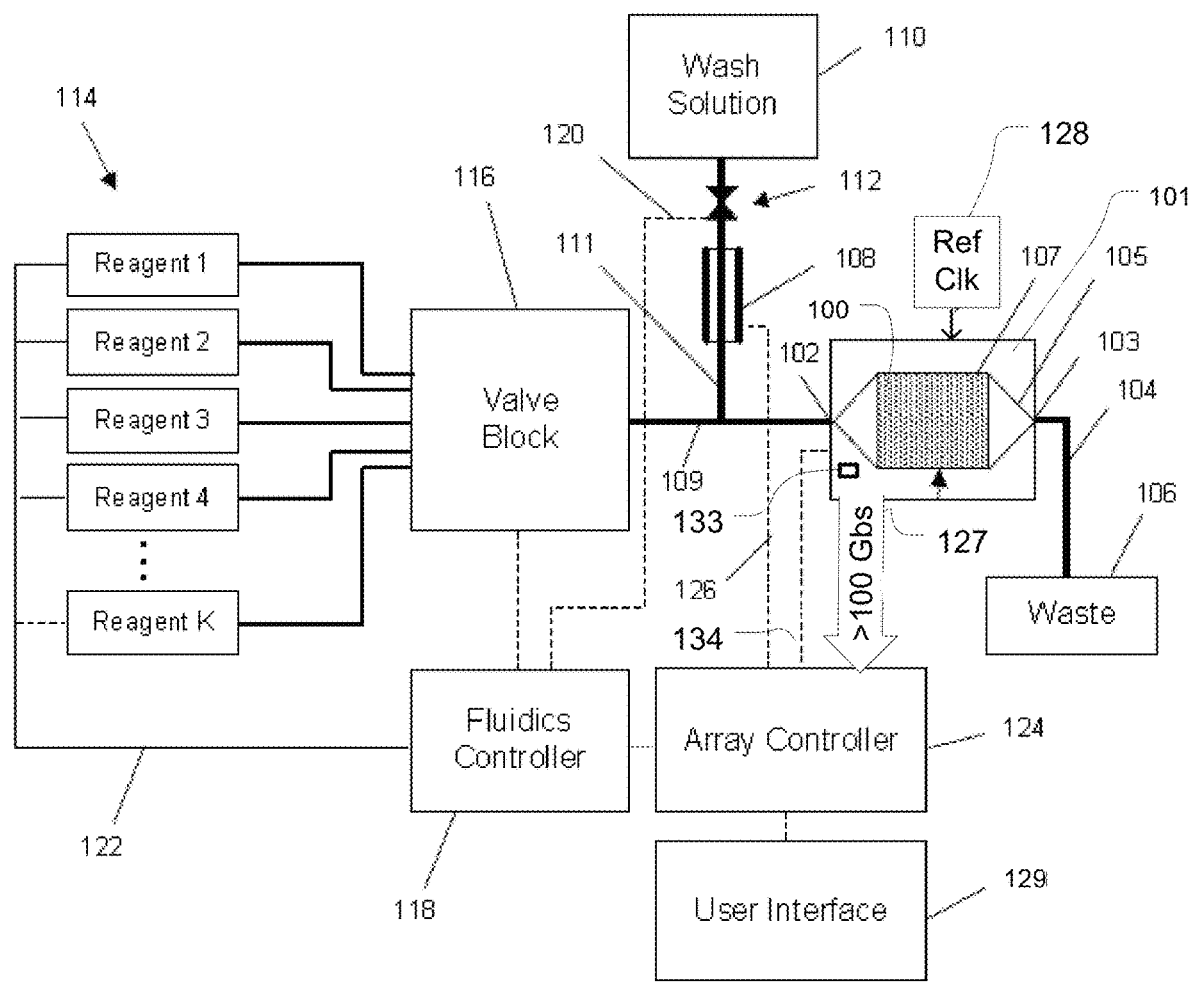
FIG. 1 is a block diagram of components of a sensor system for nucleic acid sequencing according to an exemplary embodiment.

FIG. 1 is a block diagram of components of a system for nucleic acid sequencing according to some embodiments. Such systems include device 100, which acts as a source of data that produces over 50 Gb per second of digital data, and in examples described herein, produces over 100 Gb per second, and more. As illustrated schematically, a communication bus 127 supporting over 100 Gb per second may be desired in embodiments of the technology described herein. In an example system, a sensor chip includes over 600 million sensors, producing multiple bits per sensor, and senses at high frame rates. A massively parallel system for transmitting data from a sensor array, or other high data rate source of data, on an integrated circuit, to a destination processor is described herein.

The nucleic acid sequencing system not only includes a source of huge amounts of data, but also presents design issues that arise because of the nature of the sensing and sequencing technology. Thus, the technology presented herein may be adapted for deployment in such systems, and an example of such a system is described herein. The components include flow cell 101 on integrated circuit device 100, reference electrode 108, a plurality of reagents 114 for sequencing, valve block 116, wash solution 110, valve 112, fluidics controller 118, lines 120/122/126, passages 104/109/111, waste container 106, array controller 124, a reference clock 128 and user interface 129. Integrated circuit device 100 includes microwell array 107 overlying a sensor array that includes devices as described herein. Flow cell 101 includes inlet 102, outlet 103, and flow chamber 105 defining a flow path of reagents over microwell array 107. Reference electrode 108 may be of any suitable type or shape, including a concentric cylinder with a fluid passage or a wire inserted into a lumen of passage 111. Reagents 114 may be driven through the fluid pathways, valves, and flow cell 101 by pumps, gas pressure, or other suitable methods, and may be discarded into waste container 106 after exiting outlet 103 of flow cell 101. Fluidics controller 118 can control driving forces for reagents 114 and operation of valve 112 (for wash fluid) and valve block 116 (for reagents) with a suitable processor executing software-implemented logic, other controller circuitry or combinations of controller circuitry and software-implemented logic. In some embodiments, fluidics controller 118 can control delivery of individual reagents 114 to flow cell 101 and integrated circuit device 100 in a predetermined sequence, for predetermined durations, and/or at predetermined flow rates.

Microwell array 107 includes an array of reaction regions which are operationally associated with corresponding sensors in the sensor array. For example, each reaction region may be coupled to one sensor or more than one sensor suitable for detecting an analyte or reaction property of interest within that reaction region. Microwell array 107 may be integrated in integrated circuit device 100, so that microwell array 107 and the sensor array are part of a single device or chip. Flow cell 101 can have a variety of configurations for controlling the path and flow rate of reagents 114 over microwell array 107.

Array controller 124 provides bias voltages and timing and control signals to integrated circuit device 100 for reading the sensors of the sensor array. Array controller 124 also provides a reference bias voltage to the reference electrode 108 to bias reagents 114 flowing over microwell array 107.

Array controller 124 includes a reader to collect output signals from the sensors of the sensor array through output ports on integrated circuit device 100 via bus 127, which comprises a plurality of high-speed serial channels for example, carrying sample data at speeds on the order of 100 gigabits per second or greater. In one example, twenty four serial channels, each of which nominally operates at 5 Gb per second, are implemented in the bus 127. A reference clock 128 may be coupled with the device 100 to provide a stable reference clock for use in controlling high-speed serial channels. In embodiments described herein, the reference clock 128 can operate at relatively low frequencies, on the order of 100 MHz or 200 MHz, as compared to the Gb data rates desired to support the high-speed serial channels. Array controller 124 can include a data processing system, with a reader board including a set of field programmable gate arrays (FPGAs), having a plurality of receivers in support of the transmitters on the device 100. Array controller 124 can include memory for storage of data and software applications, a processor for accessing data and executing applications, and components that facilitate communication with the various components of the system in FIG. 1.

The values of the output signals of the sensors can indicate physical and/or chemical parameters of one or more reactions taking place in the corresponding reaction regions in microwell array 107. For example, in some exemplary embodiments, the values of the output signals may be processed using the techniques disclosed in Rearick et al., U.S. Pat. Pub. No. 2012/0172241 (application Ser. No. 13/339,846, filed Dec. 29, 2011), and in Hubbell, U.S. Pat. Pub. No. 2012/0173158 (application Ser. No. 13/339,753, filed Dec. 29, 2011), which are all incorporated by reference herein in their entirety. User interface 129 can display information about flow cell 101 and the output signals received from sensors in the sensor array on integrated circuit device 100. User interface 129 can also display instrument settings and controls, and allow a user to enter or set instrument settings and controls.

Array controller 124 can collect and analyze the output signals of the sensors related to chemical and/or biological reactions occurring in response to the delivery of reagents 114. A management bus 134 may be connected between the array controller 124 and the integrated circuit 100, and used for controlling operation of the sensor array and other control functions. The array controller 124 can also be coupled to the fluidics controller, to provide for coordinated operation of the array and the fluid flow dynamics. The system can also monitor and control the temperature of integrated circuit device 100 using a temperature sensor 133 on the integrated circuit, so that reactions take place and measurements are made at a regulated temperature. The temperature sensor 133 may be integrated on the integrated circuit device 100, or otherwise coupled to the integrated circuit substrate or package (i.e. chip) or the flow cell 101 to sense a temperature that correlates with the temperature of the sensor array such that it may be used in a process to control temperature of the array. The system may be configured to let a single fluid or reagent contact reference electrode 108 throughout an entire multi-step reaction during operation. Valve 112 may be shut to prevent any wash solution 110 from flowing into passage 109 as reagents 114 are flowing. Although the flow of wash solution may be stopped, there can still be uninterrupted fluid and electrical communication between reference electrode 108, passage 109, and microwell array 107. The distance between reference electrode 108 and the junction between passages 109 and 111 may be selected so that little or no amount of the reagents flowing in passage 109, and possibly diffusing into passage 111, reach reference electrode 108. In some embodiments, wash solution 110 may be selected as being in continuous contact with reference electrode 108, which may be especially useful for multi-step reactions using frequent wash steps.

Figure 2:
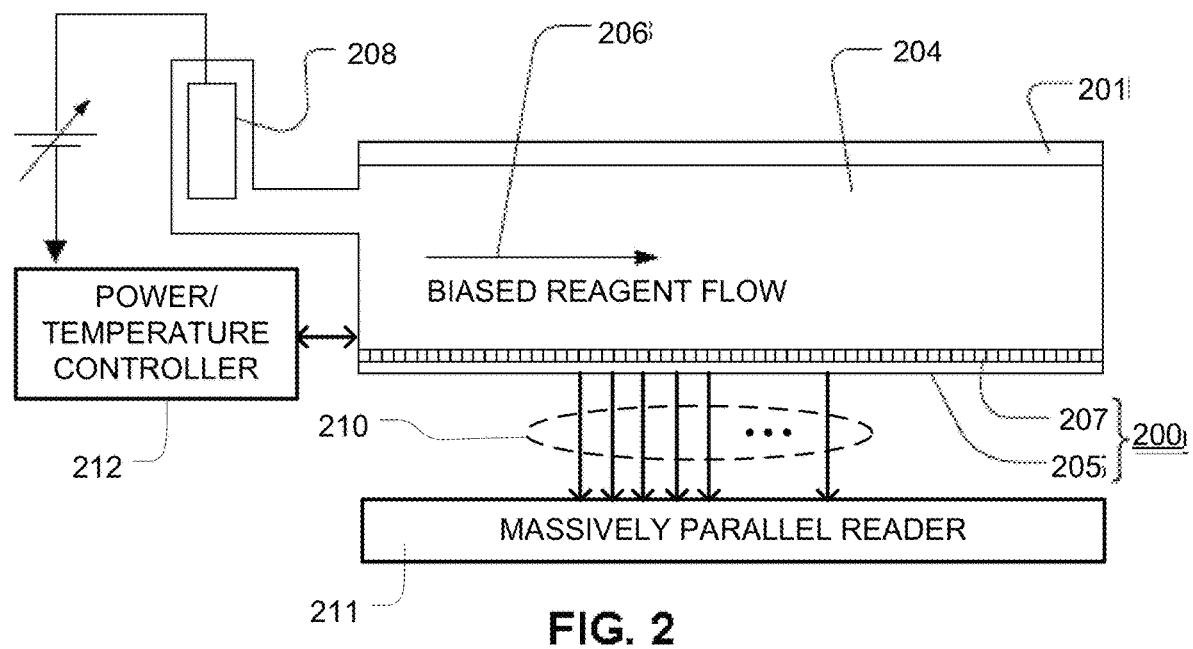
FIG. 2 illustrates a cross-sectional view of a portion of the integrated circuit device and flow cell according to an exemplary embodiment.

FIG. 2 illustrates a cross-sectional view of a portion of an exemplary integrated circuit device 200, flow cell 201 and reference electrode 208. The device includes a sensor array (schematically 205) coupled to a microwell array (schematically 207). During operation, flow chamber 204 of flow cell 201 confines reagent flow 206 of delivered reagents across open ends of the reaction regions in microwell array 207. The volume, shape, aspect ratio (such as base width-to-well depth ratio), and other dimensional characteristics of the reaction regions may be selected based on the nature of the reaction taking place, as well as the reagents, products/ byproducts, or labeling techniques (if any) that are employed. The sensors of sensor array 205 may be responsive to (and generate output signals related to) chemical and/or biological reactions within associated reaction regions in microwell array 207 to detect an analyte or reaction property of interest. The sensors of sensor array 205 may be chemically sensitive field-effect transistors (chemFETs), such as ion-sensitive field effect transistors (ISFETs). Examples of sensors and array configurations that may be used in embodiments are described in U.S. Patent Application Publication No. 2010/0300559, filed May 24, 2010, No. 2010/0197507, filed Oct. 5, 2012, No. 2010/0301398, filed Oct. 5, 2012, No. 2010/0300895, May 4, 2010, No. 2010/0137143, filed May 29, 2009, and No. 2009/0026082, filed Dec. 17, 2007, and U.S. Pat. No. 7,575,865, filed Aug. 1, 2005, each of which are incorporated by reference herein in their entirety. The interfacial fluid dynamics proximal to the microwell involve flow rate, electrolytic potential relative to the sensor array, temperature and other complex factors which can influence the sensor array in ways that may not relate to the analyte (such as a base on a DNA string) being measured. It may be desirable to maintain stability of the interfacial fluid dynamics during a sequencing operation. The system includes a power and temperature controller 212, which may be a part of the array controller described with reference to FIG. 1. The power and temperature controller 212 can communicate with the circuitry on the integrated circuit 200 to control electrical and thermal configuration of the integrated circuit, and assist in maintaining stability of the interfacial fluid dynamics, in coordination with the fluidic controller which can manage flow rates and temperatures of the fluids.

The integrated circuit device 200 includes a large number of serial ports supporting connection to a massively parallel reader 211 via a set of serial channels 210. The reagent flow 206, coupled with a large array of ISFETs, presents a complex electrical and mechanical environment in which such a system can operate with high integrity.

In some embodiments, other types of sensor arrays may be used in systems like that of FIG. 1, including but not limited to arrays of thermistors and arrays of optical sensors.

Figure 3:
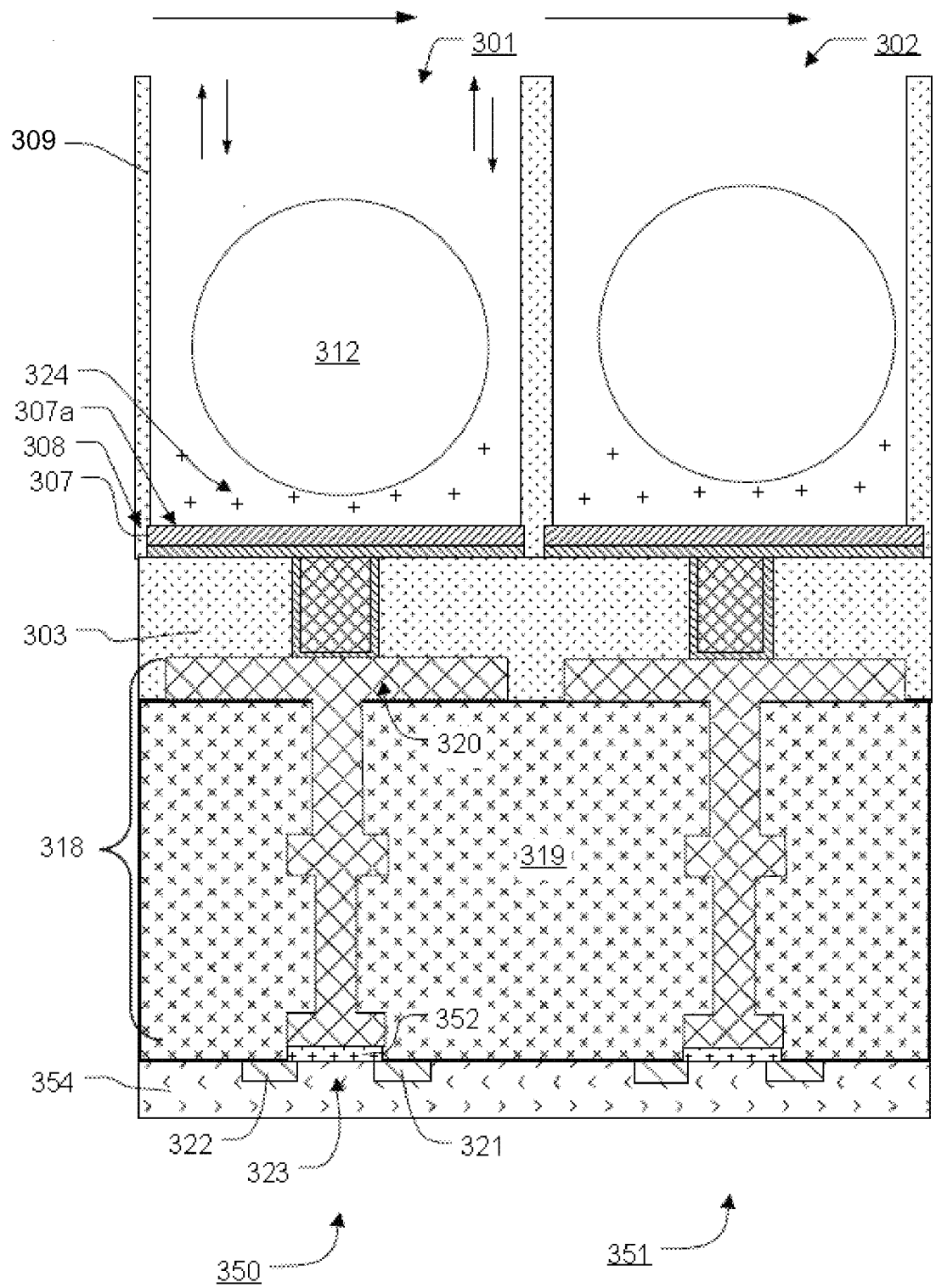
FIG. 3 illustrates a cross-sectional view of representative sensors/detectors and corresponding reaction regions according to an exemplary embodiment.

FIG. 3 illustrates a cross-sectional view of representative sensors/detectors and corresponding reaction regions according to an exemplary embodiment. In some embodiments the sensors may be chemical sensors. Fig. shows 3 two exemplary sensors 350, 351, representing a small portion of a sensor array that can include millions of sensors; even billions of sensors are contemplated. For example, the sensor array can comprise between 100 and 1,000 sensors, between 100 and 10,000 sensors, between 10,000 and 100,000 sensors, between 100,000 and 1,000,000 sensors, between 1,000,000 and 40,000,000 sensors, between 10,000,000 and 165,000,000 sensors, between 100,000,000 and 660,000,000 sensors, between 1,000,000,000 and 5,000,000,000 sensors, between 5,000,000,000 and 9,000,000,000 sensors, and up to 10,000,000,000 sensors. Windowing of the array is contemplated such that data can be obtained from all or fewer than all of the sensors. Sensor 350 is coupled to corresponding reaction region 301, and sensor 351 is coupled to corresponding reaction region 302. The two illustrated reaction regions are chemically and electrically isolated from one another and from neighboring reaction regions. The dielectric material 303 defines the reaction regions 301/302 which may be within an opening defined by an absence of dielectric material. Dielectric material 303 can comprise one or more layers of material, such as silicon dioxide or silicon nitride or any other suitable material or mixture of materials. The dimensions of the openings, and their pitch, can vary from embodiment to embodiment. In some embodiments, the openings can have a characteristic diameter, defined as the square root of 4 times the plan view cross-sectional area (A) divided by Pi (e.g., sqrt(4*A/π), of not greater than 5 micrometers, such as not greater than 3.5 micrometers, not greater than 2.0 micrometers, not greater than 1.6 micrometers, not greater than 1.0 micrometers, not greater than 0.8 micrometers, not greater than 0.6 micrometers, not greater than 0.4 micrometers, not greater than 0.2 micrometers or not greater than 0.1 micrometers. The plan view area of the sensor is determined in part by the width (or diameter) of reaction regions and may be made small to provide a high density array. The footprint of a sensor may be determined and/or reduced by modifying the width (e.g. diameter) of the reaction region. In some embodiments, the density of the array may be increased or decreased based on the diameter selected for the reaction region. Low noise sensors may be provided in a high density array by reducing device and interconnect overhead, including gate area and contact area. Additional examples of sensors and their corresponding reaction regions according to additional exemplary embodiments are described in Fife et al., U.S. patent application Ser. No. 14/198,382, filed Mar. 5, 2014, based on U.S. Prov. Pat. Appl. Nos. 61/868,739, filed Aug. 22, 2013, and 61/790,866, filed Mar. 15, 2013; Fife et al., U.S. patent application Ser. No. 14/197,710, filed Mar. 5, 2014, based on U.S. Prov. Pat. Appl. Nos. 61/868,736, filed Aug. 22, 2013, and 61/790,866, filed Mar. 15, 2013; Fife et al., U.S. patent application Ser. No. 14/198,402, filed Mar. 5, 2014, based on U.S. Prov. Pat. Appl. Nos. 61/868,942, filed Aug. 22, 2013, and 61/790,866, filed Mar. 15, 2013; Fife et al., U.S. patent application Ser. No. 14/197,741, filed Mar. 5, 2014, based on U.S. Prov. Pat. Appl. Nos. 61/868,947, filed Aug. 22, 2013, and 61/790,866, filed Mar. 15, 2013; and Fife et al., U.S. patent application Ser. No. 14/198,417, filed Mar. 5, 2014, based on U.S. Prov. Pat. Appl. Nos. 61/900,907, filed Aug. 22, 2013, and 61/790,866, filed Mar. 15, 2013, which are all incorporated by reference herein in their entirety.

Sensor 350 is representative of the sensors in the sensor array. In the illustrated example, sensor 350 is a chemically-sensitive field effect transistor (chemFET), more specifically an ion-sensitive field effect transistor (ISFET) in this example. Sensor 350 includes floating gate structure 318 having sensor plate 320 coupled to reaction region 301 by electrode 307 which can have a surface adapted for contact with an electrolyte (an ionic conducting liquid). Sensor plate 320 is the uppermost floating gate conductor in floating gate structure 318. In the illustrated example, floating gate structure 318 includes multiple patterned layers of conductive material within layers of dielectric material 319. Sensor 350 also includes conduction terminals including source/drain region 321 and source/drain region 322 within semiconductor substrate 354. Source/drain region 321 and source/drain region 322 comprise doped semiconductor material having a conductivity type different from the conductivity type of substrate 354. For example, source/drain region 321 and source/drain region 322 can comprise doped P-type semiconductor material, and the substrate can comprise doped N-type semiconductor material. Channel region 323 separates source/drain region 321 and source/drain region 322. Floating gate structure 318 overlies channel region 323, and is separated from substrate 354 by gate dielectric 352. Gate dielectric may be silicon dioxide, for example. Alternatively, other suitable dielectrics may be used for gate dielectric 352 such as, for example materials with higher dielectric constants, silicon carbide (SiC), silicon nitride ($Si_3N_4$), Oxynitride, aluminum nitride (AlN), hafnium dioxide ($HfO_2$), tin oxide ($SnO_2$), cesium oxide (CeO2), titanium oxide (TiO2), tungsten oxide (WO3), aluminum oxide (Al2O3), lanthanum oxide (La2O3), gadolinium oxide and others, and any combination thereof.

In some embodiments, sensor 350 includes electrode 307 overlying and in communication with an uppermost floating gate conductor in the plurality of floating gate conductors. Upper surface 308 of electrode 307 defines a bottom surface of a reaction region for the sensor. Upper surface 308 of electrode 307 can act as the sensor surface of the sensitive area for sensor 350. Electrode 307 can comprise one or more of a variety of different materials to facilitate sensitivity to particular ions. For example, silicon nitride or silicon oxynitride, as well as metal oxides such as silicon oxide, aluminum or tantalum oxides, generally provide sensitivity to hydrogen ions, whereas sensing materials comprising polyvinyl chloride containing valinomycin provide sensitivity to potassium ions. Materials sensitive to other ions such as sodium, silver, iron, bromine, iodine, calcium, hydroxide, phosphate, and nitrate can also be used. In the illustrated example, electrode 307 is shown as a single layer of material. More generally, the electrically electrode can comprise one or more layers of a variety of electrically conductive materials, such as metals or ceramics, or any other suitable conductive material or mixture of materials, depending upon the implementation. The conductive material may be any suitable metallic material or alloy thereof, or may be any suitable ceramic material, or a combination thereof. Examples of metallic materials include aluminum, copper, nickel, titanium, silver, gold, platinum, hafnium, lanthanum, tantalum, tungsten, iridium, zirconium, palladium, or any suitable material or combination thereof. Examples of ceramic materials include one of titanium nitride, titanium aluminum nitride, titanium oxynitride, tantalum nitride, or any suitable combination thereof. In some embodiments, an additional sensing material (not shown) is deposited on upper surface 308 of electrode 307. In some embodiments, the electrode may be titanium nitride, and titanium oxide or titanium oxynitride may be grown on the upper surface 308 during manufacturing and/or during exposure to fluids during use. Whether an oxide is formed on the upper surface depends on the conductive material used, the manufacturing processes performed, and/or the conditions under which the sensor is operated. The electrode may be formed in various shapes (width, height, etc.) depending on the materials and/or etch techniques and/or fabrication processes etc. used during the manufacture process.

In some embodiments, reactants, wash solutions, and other reagents can move in and out of reaction region 301 by diffusion mechanism. Sensor 350 is responsive to (and can generate an output signal related to) charge 324 proximate to electrode 307. For example, when the sensor is coupled to an electrolyte, the sensor may be responsive to an electrolytic potential at the sensor surface. The responsiveness of the sensor can relate to the amount of charge that is present proximate to the electrode 307. The presence of charge 324 in an analyte solution can alter the surface potential at the interface between the analyte solution and upper surface 308 of electrode 307. For example, the surface potential may be altered by protonation or deprotonation of surface groups caused by the ions present in the analyte solution. In another example, the charge of surface functionality or absorbed chemical species may be altered by analytes in solution. Changes in the amount of charge present can cause changes in the voltage on floating gate structure 318, which in turn can cause an effective change in the threshold voltage of the transistor of sensor 350. The potential at the interface may be measured by measuring the current in channel region 323 between source region 321 and drain region 322. As a result, sensor 350 may be used directly to provide a current-based output signal on an array line connected to source region 321 or drain region 322, or indirectly with additional circuitry to provide a voltage-based output signal. Charge may be more highly concentrated near the bottom of reaction region 301. Accordingly, in some embodiments variations in the dimensions of the electrode can have an effect on the amplitude of the signal detected in response to charge 324.

In some embodiments, reactions carried out in reaction region 301 may be analytical reactions to identify or determine characteristics or properties of an analyte of interest. Such reactions can generate directly or indirectly products/byproducts that affect the amount of charge adjacent to electrode 307. If such products/byproducts are produced in small amounts or rapidly decay or react with other constituents, multiple copies of the same analyte may be analyzed in reaction region 301 at the same time in order to increase the output signal generated. In some embodiments, multiple copies of an analyte may be attached to solid phase support 312, either before or after being deposited into reaction region 301. Solid phase support 312 may be a particle, a microparticle, a nanoparticle. In some embodiments, the analyte may be attached to a bead which may be solid or porous and can further comprise a gel, or the like, or any other suitable solid support that may be introduced to a reaction region. In some embodiments, copies of an analyte may be located in a solution proximal to a sensor of a reaction region. Alternatively, copies of an analyte can bind directly to the surface of the sensor to capture agents includes the material on the surface or if there are pores on the surface (for example, copies of an analyte can bind directly to electrode 307). The solid phase support may be of varied size, for example, in a range of 100 nm to 10 micrometers. Further, the solid support may be positioned in the opening at various places. For a nucleic acid analyte, multiple, connected copies may be made by rolling circle amplification (RCA), exponential RCA, polymerase chain reaction (PCR) or like techniques, to produce an amplicon without the need of a solid support.

In various exemplary embodiments, the methods, and systems described herein can advantageously be used to process and/or analyze data and signals obtained from a biological reaction, including amplification or electronic or charged-based nucleic acid sequencing. In electronic or charged-based sequencing (such as pH-based sequencing), a nucleotide incorporation event may be determined by detecting ions (e.g., hydrogen ions) that are generated as natural products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of deoxynucleoside triphosphate ("dNTP") addition (which may be referred to herein as "nucleotide flows" from which nucleotide incorporations can result) and washing. The primer may be annealed to the sample or template so that the primer's 3' end may be extended by a polymerase whenever dNTPs complementary to the next base in the template are added. Based on the known sequence of nucleotide flows and on measured output signals of the sensors indicative of ion concentration during each nucleotide flow, the identity of the type, sequence and number of nucleotide(s) associated with a sample nucleic acid present in a reaction region coupled to a sensor may be determined.

Figure 4:
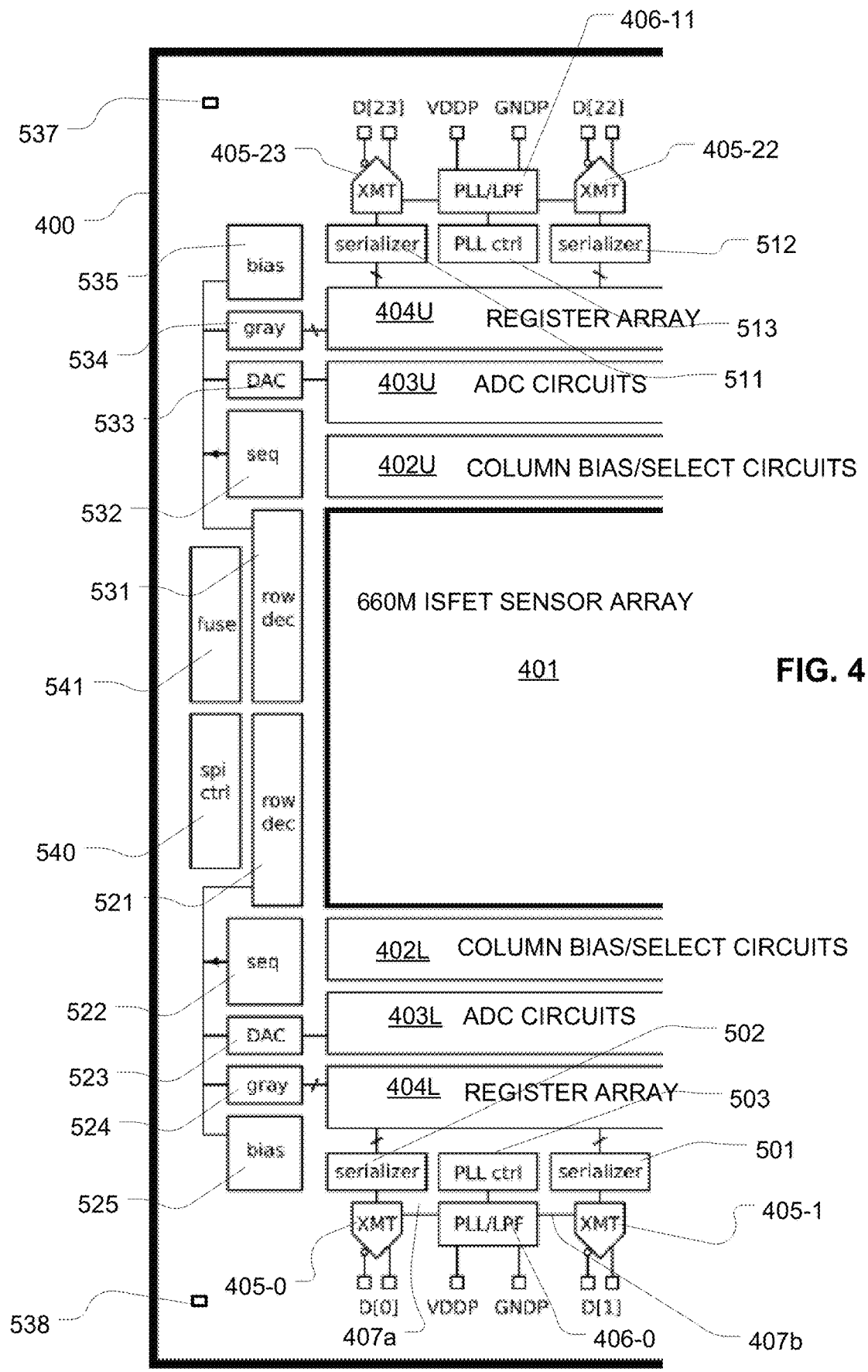
FIG. 4 is a simplified diagram of a portion of an integrated circuit including a sensor array and phase locked loop coupled transmitter pair configuration.

FIG. 4 is a simplified block diagram of part of the circuitry on an integrated circuit sensor array used for DNA sequencing. The integrated circuit includes a 660 megapixel ISFET sensor array 401 on a substrate 400. An upper set of column bias/select circuits 402U and an upper row decoder 531 are configured for access to an upper half of the array 401. A lower set of column bias/select circuits 402L and a lower row decoder 521 are configured for access to a lower half of the array 401.

An upper set of analog-to-digital converter (ADC) circuits 403U is coupled to the upper set of column bias and select circuits 402U. An upper register array 404U is coupled to the upper set of analog-to-digital converter (ADC) circuits 403U. The upper register array 404U is configured to provide a plurality of streams of digital data through serializers (e.g. 511, 512) to corresponding transmitters (e.g. 405-23, 405-22). Each of the transmitters is coupled to a corresponding pair (a pair for D[23], a pair for D[22]) of output pads, which in turn are connected to transmission lines (not shown).

Likewise, a lower set of analog-to-digital converter circuits 403L is coupled to the lower set of column bias and select circuits 402L. A lower register array 404L is coupled to the lower set of analog-to-digital converter circuits 403L. The lower register array 404L is configured to provide a plurality of streams of digital data through serializers (e.g. 501, 502) to corresponding transmitters (e.g. 405-0, 405-1). Each of the transmitters is coupled to a corresponding pair (D[0], D[1]) of output pads, which in turn are connected to transmission lines (not shown).

The array may include a number of reference cells, which are not coupled to the fluidics. The gates of the reference cells are coupled to a reference voltage circuit, and provide reference readings used in analysis of the data from the ISFETs that are coupled to the fluidics.

The configurations described herein support a device having a large number of gigabit per second transmitters, such as at least 20 transmitters capable of transmission at a data rate greater than 1 Gb per second, and configured in at least 10 pairs. For one example, the device includes 24 transmitters capable of transmitting data at 5 Gb per second each, or faster, supporting throughput from a high speed data source of 120 Gb per second or more. Large numbers of gigabit per second transmitters present a context in which a class of implementation problems arises which is not apparent in configurations with small numbers of transmitters.

Supporting peripheral circuitry including a sequencer (seq) 532, a digital-to-analog converter (DAC) 533, a gray code counter (grey) 534, and bias circuitry (bias) 535 is coupled to the upper circuitry. Also, supporting circuitry including a sequencer 522, a digital-to-analog converter 523, a gray code counter 524, and bias circuitry 525 is coupled to the lower circuitry. The chip includes a serial peripheral interface control block (spi ctrl) 540 including configuration registers and providing an interface of a management bus used in configuration and control of the device, and a fuse array (fuse) 541 used in configuration of the device. The sequencer 522, 532 operates the sensor array (or other data source), the peripheral circuitry and the plurality of transmitters to sample frames of data at a frame rate according an active mode and an idle mode, wherein the sequencer operates in the active mode for a first number of frames in a first time interval and in the idle mode for a second number of frames in a second time interval. The operation of the sequencer 522, 532 is coordinated in the sensing system with the fluidics controller, so that the first time interval overlaps with a flow of reactant solution, and the second time interval overlaps with an immediately following flow of wash solution.

In one example operating technique, sequencer 522, 532 causes the circuitry to perform a frame sensing sequence. In a frame sensing sequence, a row of ISFETs in each of the upper and lower halves of the array may be selected and biased using the column bias/select circuits 402U/402L so that a current that is a function of the charge in that corresponding sensor well may be produced on each column line. The analog-to-digital converter circuits 403U/403L receive a ramp signal from the digital-to-analog converter 533, 523, and produce an output signal when the current on the corresponding column line matches the level of the ramp signal. The gray code counter 524, 534 may be sampled in response to the output signal, and the results are stored in the register array 404U/404L. Data in the register array 404U/404L are assembled into packets, and applied in a plurality of digital data streams to the transmitters on the chip.

The illustrated part of the circuitry in FIG. 4 includes four transmitters out of a set of 24 transmitters on the substrate 400. The four transmitters illustrated include a first pair of transmitters 405-0, 405-1, and a second pair of transmitters 405-22, 405-23. As shown, one phase locked loop 406-0, including a low pass filter, is coupled to the first pair of transmitters 405-0, 405-1. Also, one phase locked loop 406-11, including a low pass filter, is coupled to the second pair of transmitters 405-22, 405-23. The phased locked loops operate as clock multipliers, each of which produces a local transmit clock and provides the local transmit clock to the transmitter on its left and to the transmitter on its right via clock lines (e.g. 407a, 407b at phase locked loop 406-0).

Each phase locked loop/low pass filter, 406-0, 406-11, is coupled with corresponding phase locked loop control block 503, 513 which stores parameters used to control and calibrate phase locked loop.

This pattern may be repeated across the 24 transmitters on the chip, so that there are 12 phase locked loop blocks, and 24 transmitters. The transmitters are grouped into pairs which are coupled to individual phase locked loops. The phase locked loops are disposed on the substrate between the transmitters, so that the transmission distance from the phase locked loop to the transmitter using the clock produced in the phase locked loop may be small.

As illustrated, each of the phase locked loops 406-0, 406-11 is coupled to an individual power pad VDDP and an individual ground pad GNDP. Also, the individual power pad VDDP and the individual ground pad GNDP for each phase locked loop are disposed on the chip adjacent the phase locked loop, and between the output pads for the transmitter on the left, and the output pads for the transmitter on the right in the corresponding transmitter pair.

The individual power pad VDDP and the individual ground pad GNDP are connected to an off-chip voltage supply, which may be configured with bypass capacitors and other circuitry, to create a low noise power configuration for the phase locked loop circuits, and to reduce coupling of noise between the high-frequency phase locked loop circuits and other circuits on the substrate 400.

A low-speed reference clock (not shown, see FIG. 5) may be distributed on the chip and connected to each of the phase locked loops.

The clock multipliers in the illustrated embodiment are implemented using phase locked loops. Clock multipliers may be implemented using other circuitry as well, such as delay locked loops, phase interpolators, and combinations of phase locked loops, phase interpolators and/or delay locked loops.

In this example, the integrated circuit substrate 400 includes on-chip temperature sensors 537, 538, configured on each of the four corners of the chip. The temperature readings are sampled by the SPI control block 540, and stored for access by off-chip controllers via the management bus. Also, the temperature readings are utilized by the sequencers to control power consumption and temperature on the device. In other embodiments, the temperature sensor or sensors may be configured differently. In yet other embodiments, a temperature sensor may be coupled to the microwell array structure, in addition to or in the alternative to the temperature sensor or sensors on chip.

Figure 5:
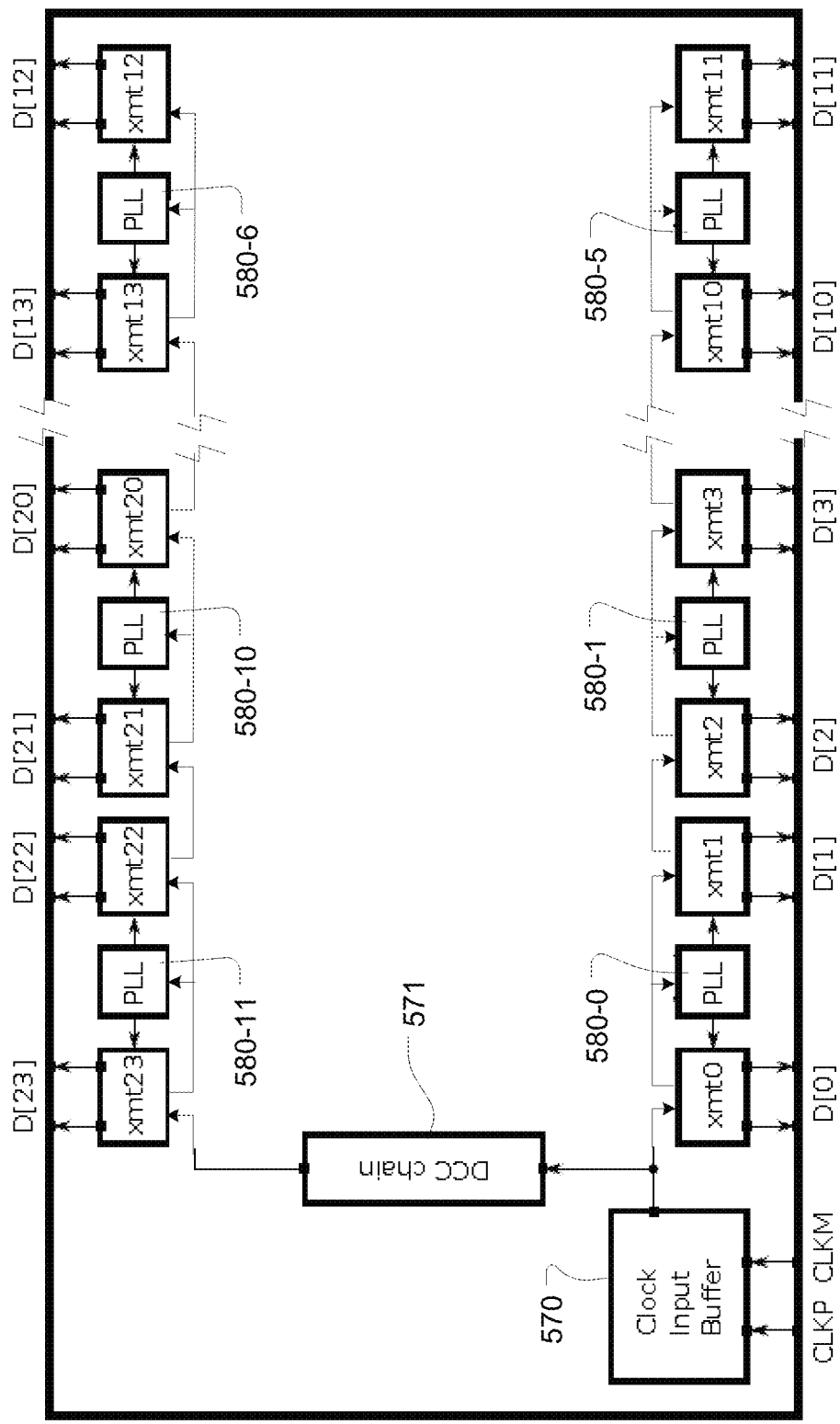
FIG. 5 is a simplified diagram of a clock distribution network for an integrated circuit like that shown in FIG. 4.

FIG. 5 illustrates clock distribution circuitry which may be utilized with a device like that shown in FIG. 4. The clock distribution circuitry includes a clock input buffer 570 which includes CLKP and CLKN inputs configurable to receive a differential clock signal or a single ended clock signal from an off-chip clock reference. The output of the clock buffer 570 may be distributed in a daisy chain fashion to the phase locked loops 580-0 through 580-5 disposed along a lower side of the chip, and through a duty cycle correction DCC chain 571, which includes a group of cascaded DCC buffers to support transmission of the reference clock across the large chip, to the phase locked loops 580-6 through 580-11 along an upper side of the chip. In this example, the reference clock may be distributed to the transmitter units xmt0 to xmt1 1 on the lower side and via the DCC chain 571 to transmitter units xmt12 to xmt23 on the upper side. Each of the transmitter units includes a duty cycle correction DCC buffer, and passes the reference clock from the DCC buffer in the transmitter unit to its adjacent phase locked loop, or adjacent transmitter unit. An example of the transmitter unit circuitry including this DCC buffer is illustrated with reference to FIG. 7. In alternatives, the reference clock may be coupled directly to the phase locked loop circuit, and DCC buffers may be disposed on the chip in other configurations as desired.

The clock distribution circuit provides a reference clock at a relatively low frequency, such as 125 MHz, with a 50% duty cycle to each of the phase locked loops. In this example, the reference clock may be distributed asynchronously to the phase locked loops.

Figure 6:
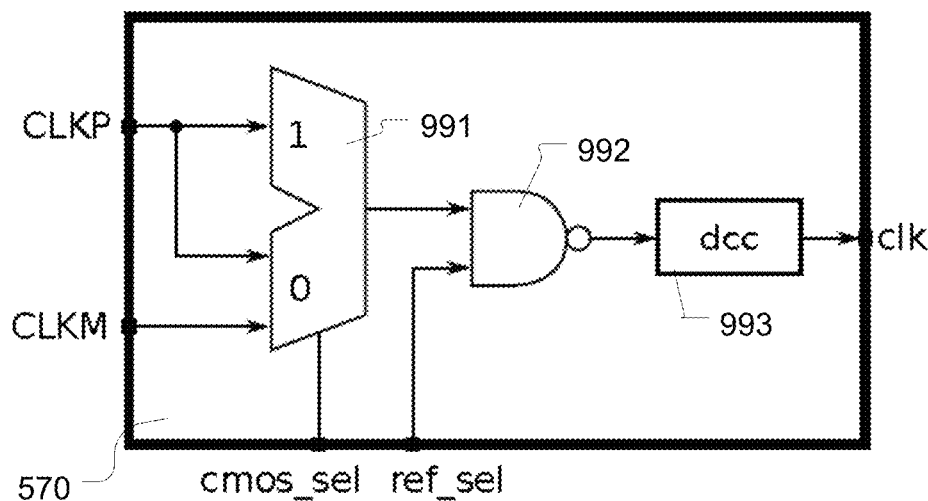
FIG. 6 is a simplified diagram of a clock input buffer for a clock distribution network like that of FIG. 5.

FIG. 6 is a block diagram of the clock input buffer 570 shown in FIG. 5. The clock input buffer 570 in this example includes a multiplexer 991. The CLKP pad is connected to both the "0" and "1" inputs of the multiplexer 991. The CLKN pad is connected to the "0" input of the multiplexer 991. A parameter set on the device, labeled cmos_sel in the figure, controls the multiplexer 991 so that it converts the differential input in one mode to a single ended output, or provides the single ended input as the single ended output. The single ended output of the multiplexer 991 may be supplied through a NAND gate 992 to a DCC buffer 993. The NAND gate 992 may be controlled by a control signal labeled ref sel in this example. The output of the DCC buffer 993 is the reference clock to be distributed on the chip.

A duty cycle correction circuit, such as that used for the DCC buffer 993, or used in the DCC chain 571 described with reference to FIG. 5, may be implemented using a variety of circuit structures. Examples are described in the literature, including Ogawa, et al., "A 50% DUTY-CYCLE CORRECTION CIRCUIT FOR PLL OUTPUT," IEEE International Symposium on Circuits and Systems (Volume: 4) ISCAS 2002; M. Ragavan, et al. "DUTY CYCLE CORRECTOR WITH SAR FOR DDR DRAM APPLICATION," International Journal of Advanced Research in Electrical, Electronics and Instrumentation Engineering, Vol. 2, Issue 5, May 2013, which are incorporate by reference in their entirety.

Figure 7:
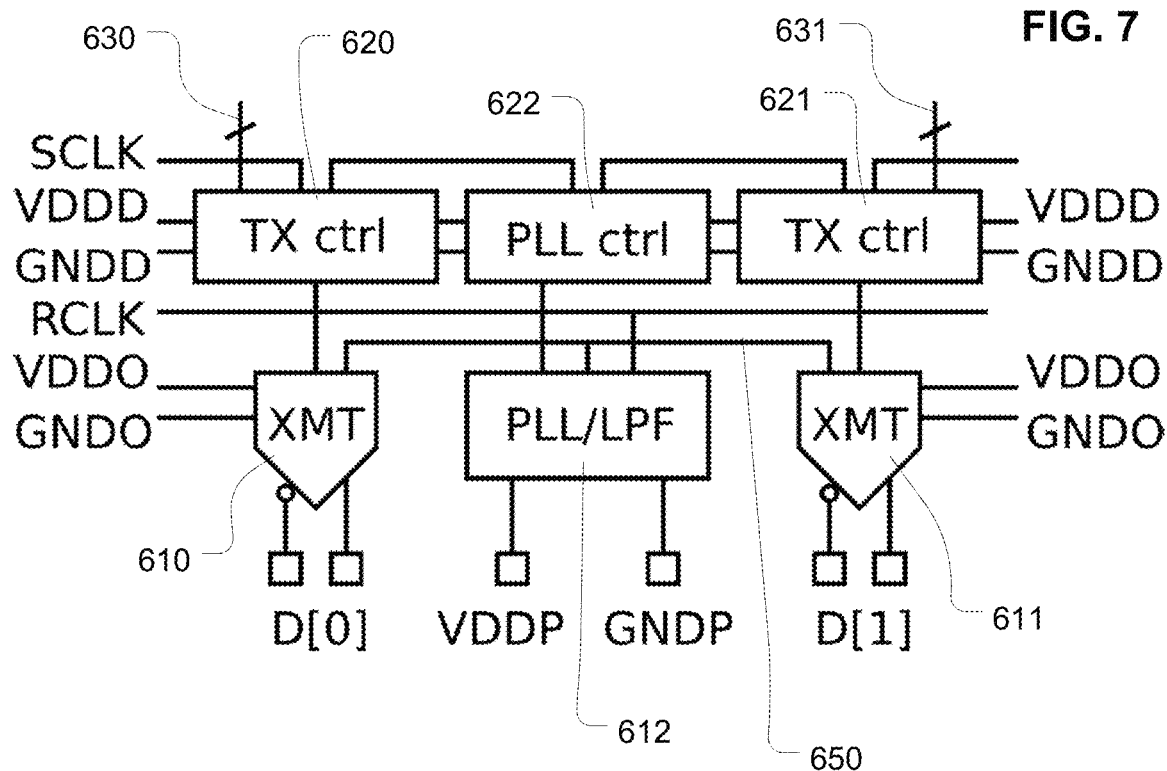
FIG. 7 illustrates a phase locked loop coupled transmitter pair according to an embodiment of the technology described herein.

FIG. 7 illustrates a configuration of a transmitter pair according to embodiments of the technology described herein. Each transmitter pair includes first transmitter XMT 610 and second transmitter XMT 611, which in this example correspond to the transmitter for output D[0] and the transmitter for output D[1] on the chip. A phase locked loop/low pass filter circuit (PLL/LPF) 612 may be disposed between the transmitters 610, 611 in the pair. Transmitter control blocks 620, 621 are coupled to the corresponding transmitters 610, 611. Corresponding data streams 630, 631 are input to the transmit control block 620, 621 from the register array on the chip. A phase locked loop control block 622 is coupled to the phase locked loop/low pass filter 612.

Three power domains are implemented in the transmitter pair configuration shown in FIG. 7. Control blocks 620, 621, 622 receive power in a digital power domain based on the supply terminals VDDD and GNDD. The transmitters 610, 611 receive power in a transmitter power domain (output "0" power) based on supply terminals VDDO, GNDO. The phase locked loop/low pass filter circuits are disposed in individual power domains based on supply terminals VDDP, GNDP that are directly connected to the phase locked loop/low pass filter circuitry.

The reference clock RCLK is coupled to the phase locked loop from clock distribution circuitry, like that described above. A system clock SCLK is coupled to the control blocks 620, 621, 622. The system clock can operate nominally at the same frequency as the reference clock in some embodiments, but may be a different frequency.

The phase locked loop 612 operates as a clock multiplier, producing a high speed, local transmit clock on line 650.

In one example, the system clock and reference clock operate at 125 MHz. The high-speed, local transmit clock may be produced at 2.5 GHz (20x multiplication). The transmitters in this example transmit on both the rising and falling edges of the local transmit clock, resulting in a transmission rate of 5 Gb per second. In a chip having 24 transmitters operating at 5 Gb per second, a throughput of 120 Gb per second may be achieved.

High data integrity of the transmitted data may be supported using techniques including distribution of a low-speed reference clock, the configuration of the phase locked loops in individual power domains, the placement of the phase locked loops between corresponding pairs of transmitters, and local use of the locally produced high-speed transmit clocks.

Figure 8:
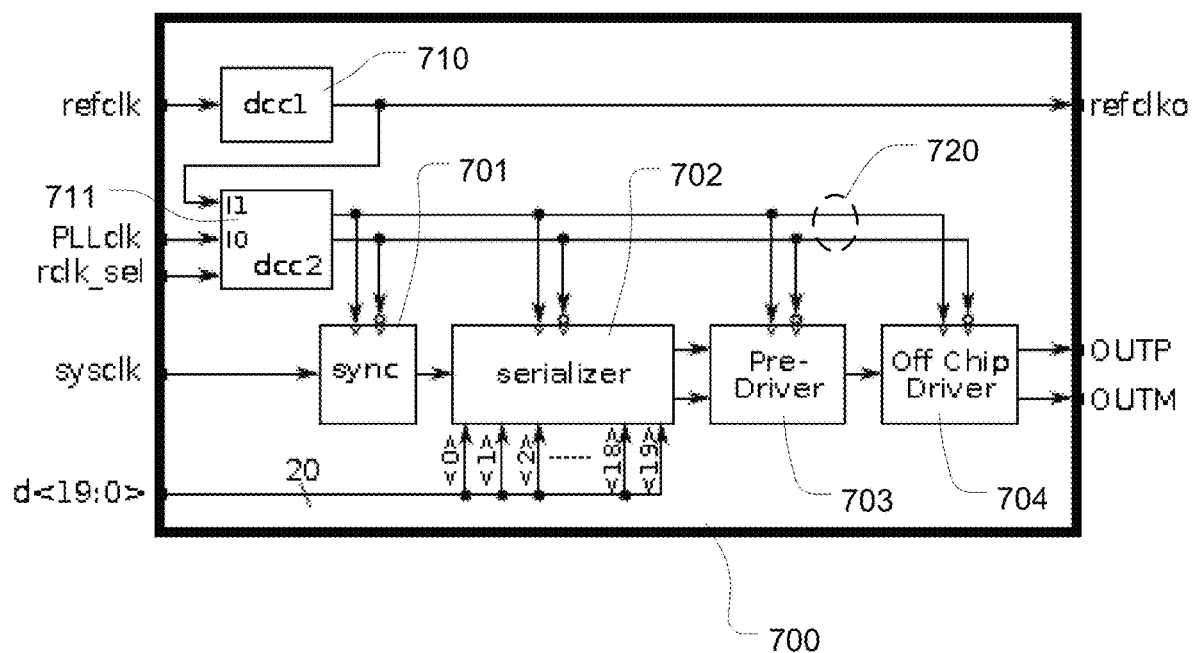
FIG. 8 is a simplified diagram of a transmit path for an integrated circuit like that shown in FIG. 4.

FIG. 8 is a block diagram of a transmitter and transmitter control block 700 which may be used in the configuration shown in FIGS. 5 and 7. A reference clock refclk may be supplied as input to a single output, DCC buffer 710. The output of the DCC buffer 710 may be applied as an output refclk0 for connection in daisy chain fashion as illustrated in FIG. 5. Also, the output of DCC buffer 710 may be supplied to a clock selector 711, which also includes a differential output DCC buffer. Clock selector 711 is capable of selecting between the local high-speed transmit clock, labeled PLLclk in this example, and the reference clock output from the DCC buffer 710. A control signal rclk_sel may be used to determine the selection. The ability to select the reference clock output from DCC buffer 710 supports testing the chip. In operating mode, the local high-speed transmit clock PLLclk may be selected. The output of the clock selector 711 may be a duty cycle-corrected, differential clock on lines 720, at the local transmit clock frequency.

The differential clock on lines 720 may be supplied to a synchronizer circuit (sync) 701, a serializer circuit 702, a pre-driver 703, and an off-chip driver 704. The output of the off-chip driver may be connected to the pads OUTP and OUTN, which are in turn connected to a transmission line. The synchronizer circuit 701 also receives the system clock, and produces a synchronized system clock for the serializer 702. The data stream from the register arrays are applied in this example in 20 bit packets to the serializer 702. The output of the serializer, which may be scrambled to maintain signal transition rates for the communication links, may be applied to the pre-driver 703, and then off chip via the off-chip driver 704.

Figure 9:
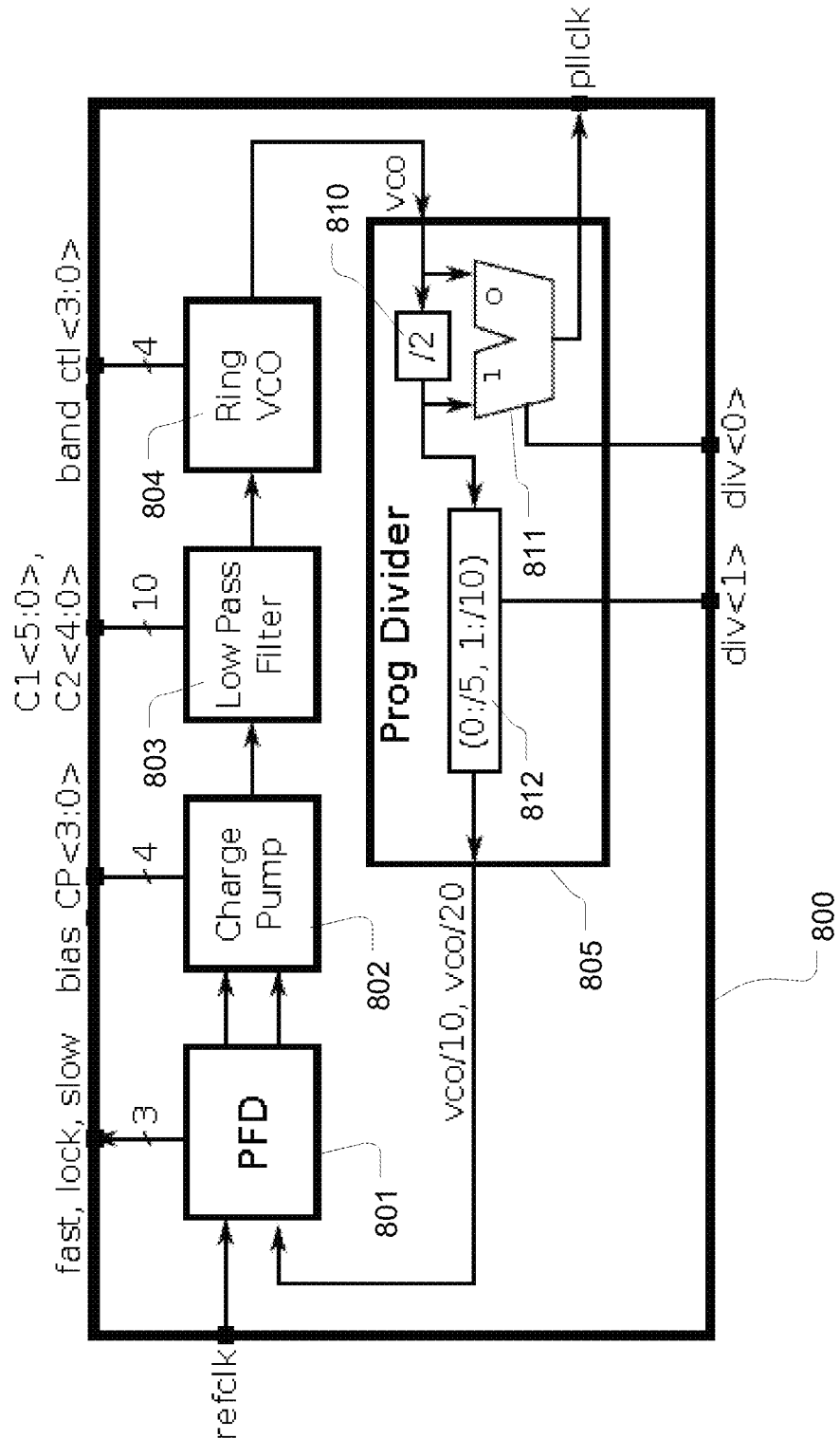
FIG. 9 is a simplified diagram of a phase locked loop that may be used in an integrated circuit like that shown in FIG. 4.

FIG. 9 is a block diagram of a phase locked loop 800 including a low pass filter, which may be utilized in the configuration of FIGS. 5 and 7. The phase locked loop 800 includes a phase frequency detector PFD (801) connected to the reference clock, a charge pump 802, a low pass filter 803, and a ring voltage controlled oscillator (VCO) 804. A programmable divider 805 may be connected between the output of the ring VCO 804, and the input of the phase and frequency detector 801. The programmable divider 805 in this example includes a clock selector 811, a first divider 810, and a second divider 812. The clock selector 811 receives the output of the ring VCO 804 at one input, and the output of the divider 810 on a second input. The divider 810 in this example may be a divide-by-two block. A control signal div<0> controls the clock selector 811. The output of the clock selector 811 may be applied as the local high-speed transmit clock pllclk. The output of the divider 810 may be applied to the input of the second divider 812. The second divider is configurable to divide by five (O:/5), or to divide by 10 1:/10, in response to a control signal div<1>. In combination, during operation, combination of the first divider 810 and the second divider 812 provides a divide-by-20 (VCO/20) operation in the 5 Gb per second example described above so that, in effect, the local high-speed transmit clock can operate at 20 times the frequency of the reference clock.

A variety of control parameters are coupled to the various blocks in the phase locked loop 800. Parameters "fast, lock, slow" are provided from the phase and frequency detector 801 to control circuitry. Charge pump bias parameters bias_CP<3:0> are applied to the charge pump 802. Low pass filter parameters C1<5:0> and C2<4:0> are applied to the low pass filter 803. VCO control parameters band_ctl<3:0> are applied to the ring VCO 804. The phase locked loop may be digitally controlled using basic phase locked loop management for calibration and configuration, driven by link control logic on the reader board in one example. In other embodiments, phase locked loop calibration and configuration may be locally driven, or a combination of local and remote operations may be utilized.

The low pass filter in the phase locked loop may be configured with a transfer function that rejects jitter in the reference clock. This may be implemented in the charge pump and filter circuitry in the loop as it operates on the output of the phase and frequency detector nominally at the frequency of the reference clock.

Figure 10A:
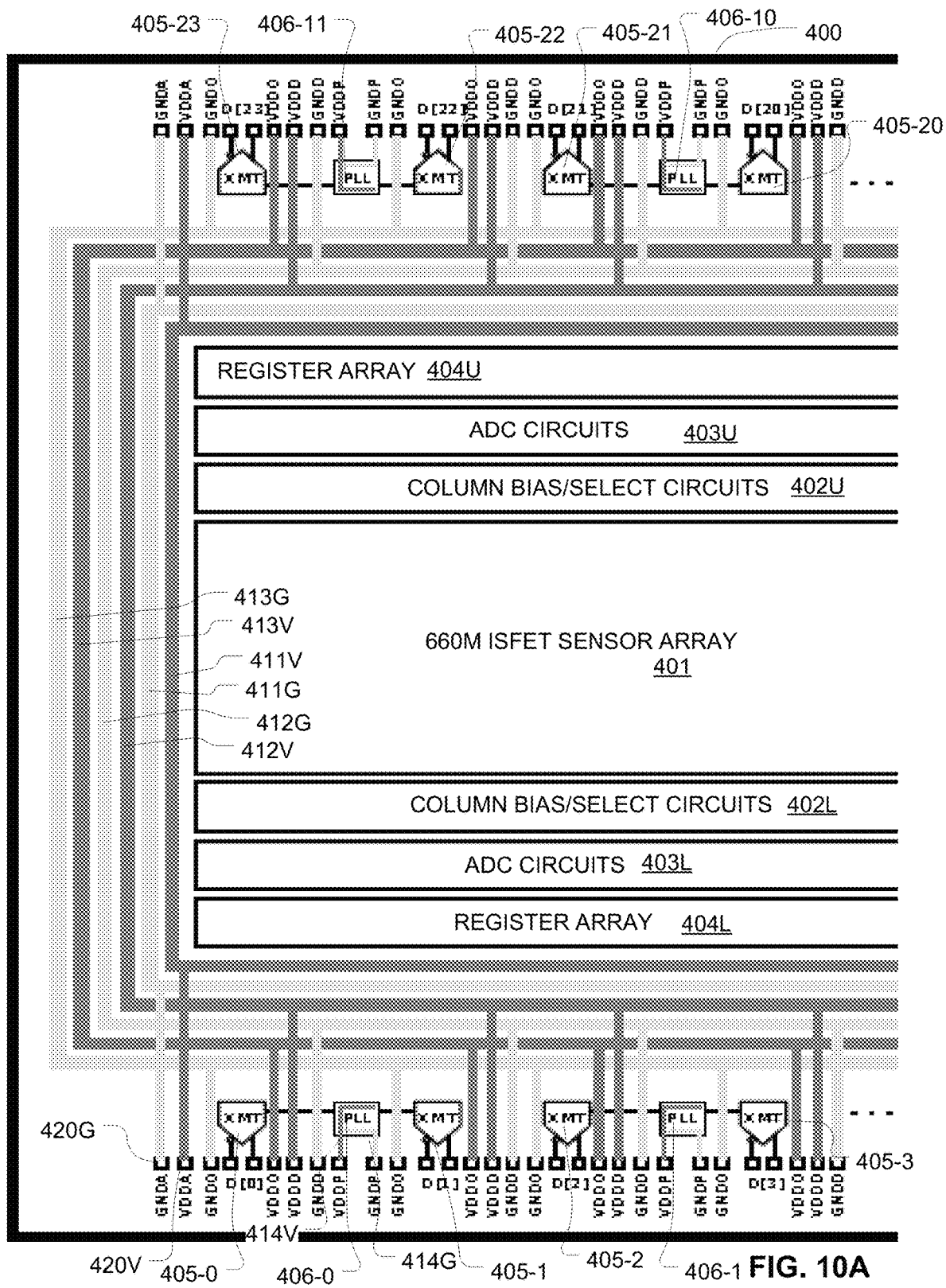
FIGS. 10A and 10B illustrate a layout of power supply traces and pads for a multiple power domain integrated circuit as described herein.
Figure 10B:
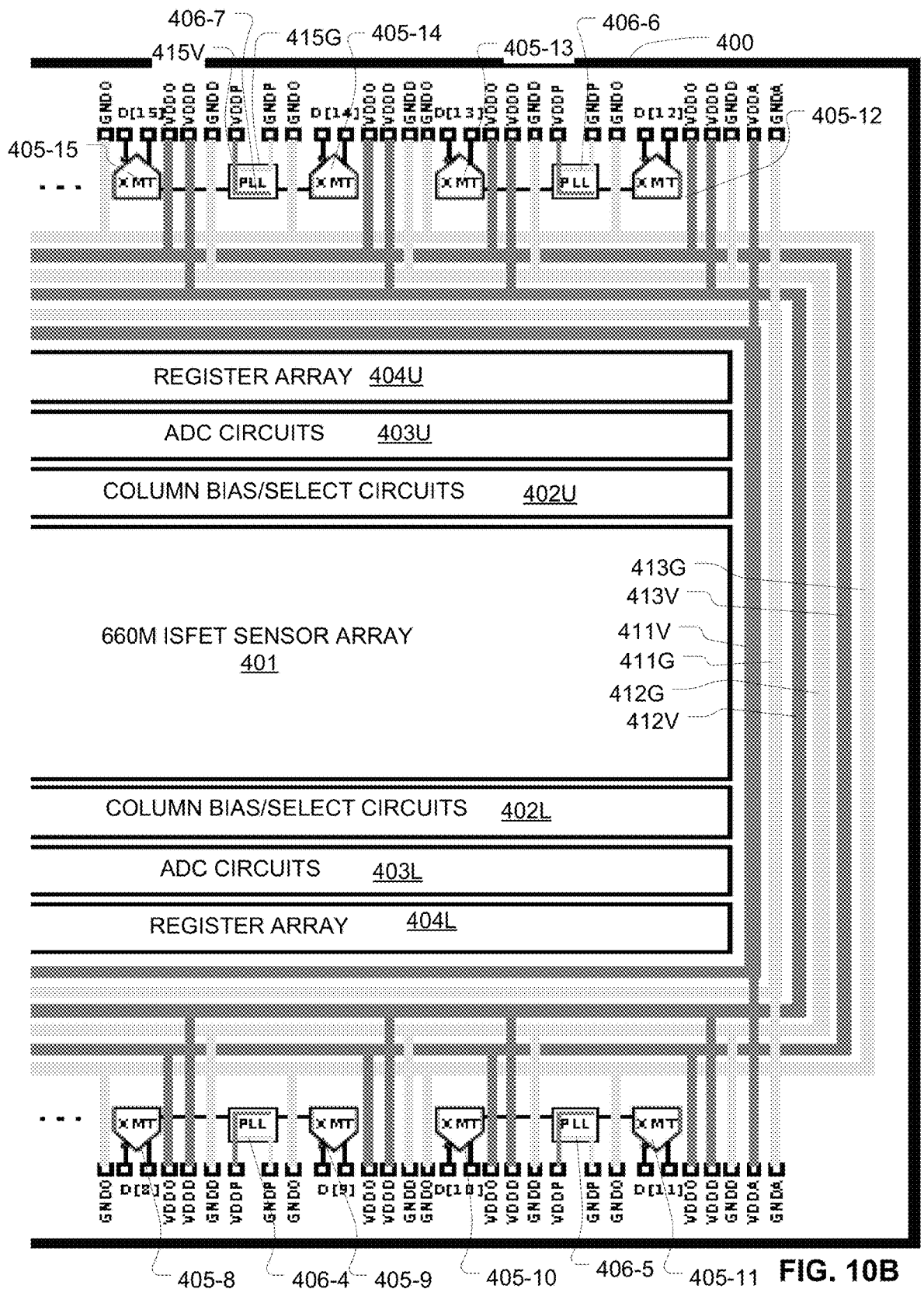

FIGS. 10A and 10B illustrate a layout of the transmitter circuits and power traces of an example sensor integrated circuit, in support of a multiple power domain system. The reference numerals used in FIG. 4 are used again for like components. Thus, the device includes a substrate 400. A 660 megapixel ISFET sensor array 401 may be implemented on the substrate. Upper and lower column bias and select circuits 402U, 402L, upper and lower analog-to-digital converter circuits 403U, 403L, and upper and lower register arrays 404U, 404L are implemented in the central region of the chip. Twelve transmitter pairs are disposed around the perimeter of the chip, with six pairs on the lower side of the chip, and six pairs on the upper side of the chip. The plurality of transmitter pairs includes first transmitter pair 405-0, 405-1, and second transmitter pair 405-2, 405-3, illustrated in FIG. 10A; and transmitter pair 405-8, 405-9, transmitter pair 405-10, 405-11 illustrated in FIG. 10B on the lower edge. Also, the plurality of transmitter pairs includes transmitter pair 405-12, 405-13 and transmitter pair 405-14, 405-15 illustrated in FIG. 10B and transmitter pair 405-20 405-21 transmitter pair 405-22 405-23 illustrated in FIG. 10A on the upper edge. Four additional transmitter pairs are implemented on the chip along the upper and lower edges, but are omitted from the drawing because of the cutout. Thus, 12 transmitter pairs are implemented on the substrate 400, for a total of 24 transmitters. As described above, each transmitter pair includes a local clock multiplier, implemented in this example by a phase locked loop with a low pass filter. Thus, FIGS. 10A and 10B show phase locked loops 406-0, 406-1, 406-4, 406-5, 406-6, 406-7, 406-10, and 406-11 each of which may be placed on the substrate between the transmitters in a corresponding pair of transmitters.

FIGS. 10A and 10B illustrate an example of a substrate that includes one or more power domains for a high data rate data source, such as the array of ISFETs illustrated, for the transmitters and for peripheral logic including reference clock distribution circuitry. In the layout of FIGS. 10A and 10B, the clock multipliers are disposed on the substrate in individual power domains separate from one another and from the other one or more power domains.

FIGS. 10A and 10B illustrate a configuration of power pads and power traces on the chip to support multiple power domains. The power domains include an analog power domain GNDA, VDDA, a digital power domain GNDD, VDDD, and a transmitter power domain GNDO, VDDO. In addition, the power domains include 12 individual power domains, one for each phase locked loop. The power pads are conductive pads on the substrate 400 adapted for connection to a pin or other connector structure for an electrical connection to off-chip structures. Such power pads often include a pad of patterned metal in the highest metal layer on the device. The power traces are conductive traces on the substrate adapted for distributing power across a region of the substrate. Such power traces are often implemented in the highest patterned metal layer on the device, and have relatively large width dimensions to support carrying a significant amount of current.

The analog power domain includes power pads labeled GNDA, VDDA on each of the four corners of the substrate 400. The analog power domain includes a power bus including a trace 411V connected to the VDDA power pads (e.g. 420V in the lower left), and a trace 411G connected to the GNDA power pads (e.g. 420G in the lower left). Traces 411V and 411G are configured on the device as the inside power traces, and surround the analog core of the device, which includes the sensor array 401, and portions of the other circuitry.

The digital power domain includes power pads labeled GNDD, VDDD distributed in pairs around the perimeter of the chip, including one pair between each transmitter. The digital power domain includes a power bus including a trace 412V connected to the VDDD power pads, and a trace 412G connected to the GNDD power pads. The traces 412V and 412G are placed on the device just outside the analog power domain traces 411V and 411G, and are placed adjacent digital circuitry surrounding the analog core of the chip.

The transmitter power domain includes power pads labeled GNDO, VDDO distributed in pairs around the perimeter of the chip, with one pair for every transmitter. Each pair of transmitter power domain power pads includes a GNDO pad on one side of the corresponding transmitter, and a VDDO pad on the opposite side of the corresponding transmitter. The transmitter power domain includes a power bus including trace 413V connected to the VDDO power pads and a trace 413G connected to the GNDO power pads. The traces 413V and 413G are configured on the device just outside the digital power domain traces 412V and 412G, and are placed for distribution of power supply voltages to the transmitters on the perimeter of the chip.

In this example, each phase locked loop may be disposed in an individual power domain. Thus, for the chip including 12 phase locked loops (or other clock multipliers) coupled with 24 transmitters, there are 12 clock multiplier power domains. Each local clock multiplier power domain includes a pair of power pads labeled GNDP, VDDP in the figure. The power pads GNDP and VDDP are disposed between the output pads for the transmitters. Thus, the power pads GNDP and VPPD for the phase locked loop 406-0 are disposed between the output pads for serial channel D[0] and the output pads for serial channel D[1]. Each local clock multiplier power domain includes a power trace and a ground trace confined to the phase locked loop circuitry. Thus, phase locked loop 406-0 includes a power trace 414V and a ground trace 414G. Likewise, phase locked loop 406-7 in FIG. 10B includes a power trace 415V and a ground trace 415G connected to the local power pad VDDP and ground pad GNDP respectively.

As may be seen from FIGS. 10A and 10B, the substrate 400 may include 12 pairs of transmitters having individual clock multipliers disposed in individual power domains between the transmitters in the pair.

The circuits in each power domain, in addition to having separate power traces, and separate power and ground pads, are isolated electrically in the substrate from one another. This isolation may be implemented using deep n-well technology, for example, in which the active regions of the circuitry are implemented within one or more doped wells separated from the bulk substrate by a deep n-well. The deep n-well may be biased using a selected power supply voltage so that it remains reverse biased relative to the substrate and relative to the active region during operation. In this manner, noise produced in the ground and power circuitry is not coupled directly into the circuitry of other power domains via the substrate.

Some or all of the power domains may be isolated using other technologies, such as by formation of the active regions in semiconductor layers deposited over layers of insulating material, so the insulating material electrically separates the active regions from the substrate.

Figure 11:
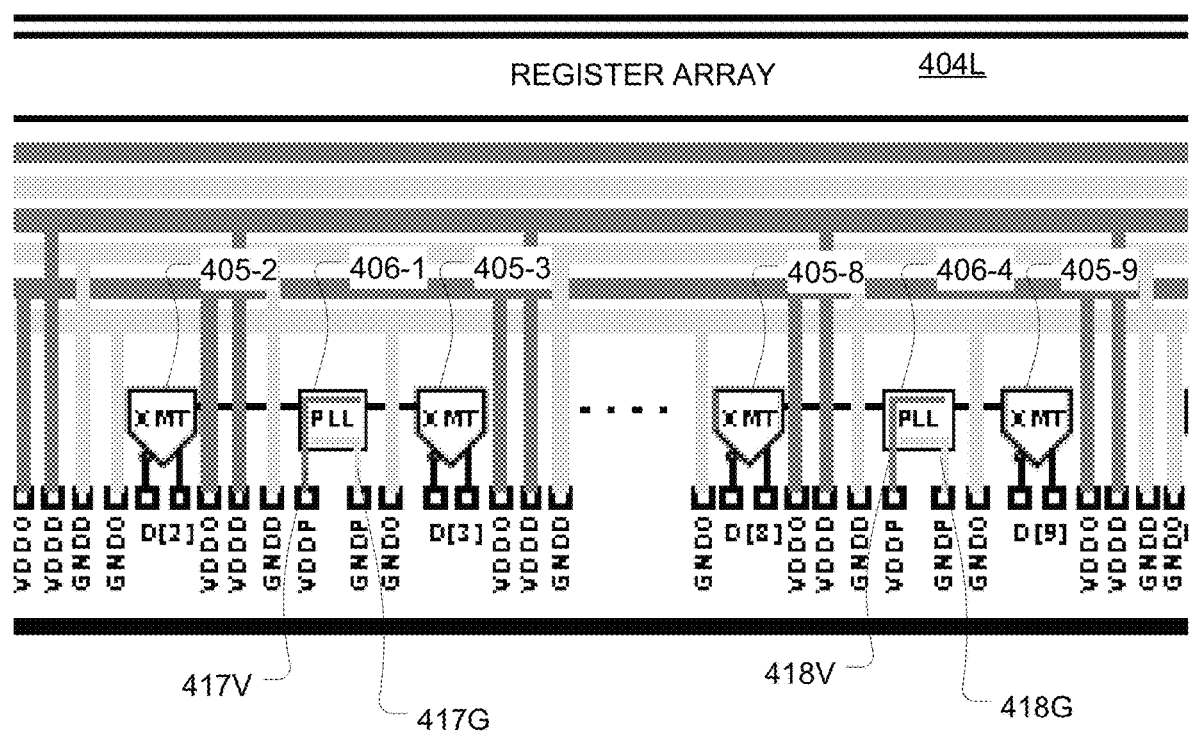
FIG. 11 is an expanded view of the power supply trace and pad layout for a portion of the integrated circuit shown in FIGS. 10A and 10B.

FIG. 11 illustrates two transmitter pairs taken from the layout of FIGS. 10A and 10B. FIG. 11 illustrates a transmitter pair 405-2, 405-3, with an individual phase locked loop 406-1 in between. Also, transmitter pair 405-8, 405-9 is shown, with an individual phase locked loop 406-4 in between. The phase locked loops have individual power pads and power traces. Thus, phase locked loop 406-1 includes the VDDP power pad connected to the power trace 417V, and the GNDP ground pad connected to the ground trace 417G. Phase locked loop 406-4 includes the VDDP power pad connected to the power trace 418V, and the GNDP ground pad connected to the ground trace 418G.

The pattern of power pads and output pads includes a set of 14 pads for each transmitter pair disposed around the substrate in a repeating sequence. The order from right to left for the set of 14 pads for the transmitter pair including transmitters 405-2 and 405-3, and phase locked loop 406-1 of the pads in this example is as follows: transmitter power domain ground pad GNDO, output pad pair D[2], transmitter power domain power pad VDDO, digital power domain power pad VDDD, digital power domain ground pad GNDD, local clock multiplier power pad VDDP, local clock multiplier ground pad GNDP, transmitter power domain ground pad GNDO, output pad pair D[3], transmitter power domain power pad VDDO, digital power domain power pad VDDD and digital power domain ground pad GNDD.

As mentioned above, in other embodiments one clock multiplier may be associated with only one transmitter, or with groups of more than two transmitters, as suits a particular need. One clock multiplier may be configured to provide a transmit clock to one or more transmitters, where the one or more transmitters are in a separate power domain than the power domain of the clock multiplier. A configuration in transmitter pairs can provide an advantage in that the length of a transmission line carrying the transmit clock from the clock multiplier to the adjacent transmitters in the transmitter pair may be configured locally and have short and uniform transmission paths, without traversing circuitry other than the clock multiplier and the connect transmitter.

Figure 12:
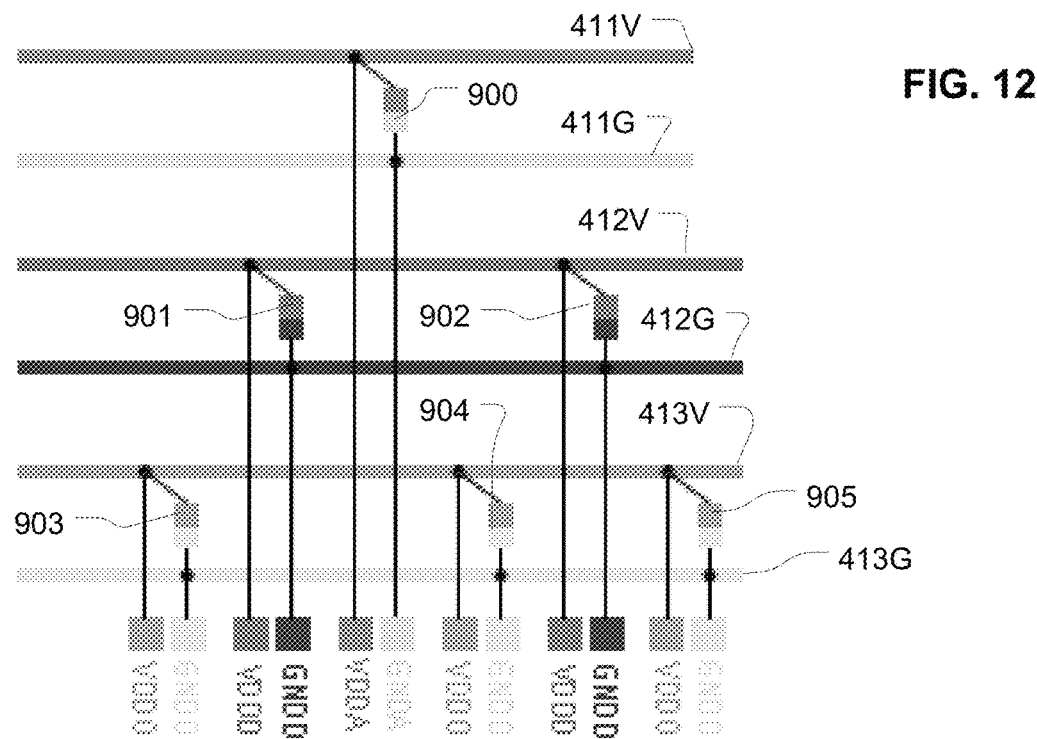
FIG. 12 illustrates a part of an electrostatic discharge protection network which may be used for the multiple power domain integrated circuit described herein.
Figure 13:
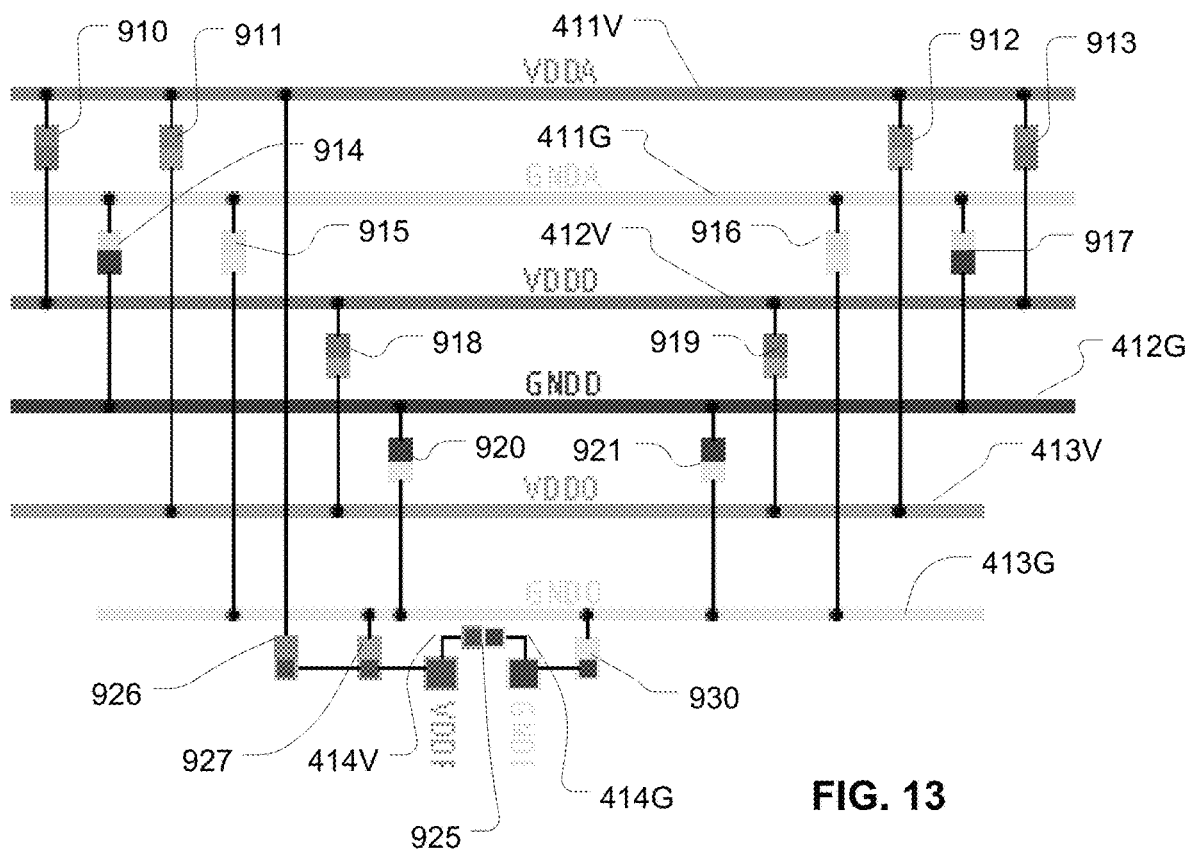
FIG. 13 illustrates another part of an electrostatic discharge protection network which may be used for the multiple power domain integrated circuit described herein.

FIG. 12 and FIG. 13 illustrate an electrostatic discharge ESD protection configuration for the plurality of power domains on a device such as that shown in FIGS. 10A and 10B. In each of FIGS. 12 and 13, the power and ground traces 411V, 411G for the analog power domain, the power and ground traces 412V, 412G for the digital power domain, and the power and ground traces 413V, 413G for the transmitter power domain are shown using the reference numbers of FIGS. 10A and 10B.

Referring to FIG. 12, an ESD protection array for protecting the ground and power pads and ground and power traces of each of the major power traces on the device is shown. The ESD circuits used include circuit 900 between the power and ground power pads (VDDA, GNDA) and traces (411V, 411G) for the analog power domain, circuits 901, 902 between the power and ground power pads (VDDD, GNDD) and traces (412V, 412G) for the digital power domain, and circuits 903, 904, 905 for the power and ground power pads (VDDO, GNDO) and traces (413V, 413G) in the transmitter power domain. The ESD circuits 900-905 may be implemented for example, utilizing reversed-biased diode configurations in a grounded gate NMOS (ggNMOS) technology connected between the power and the ground traces in the corresponding power domain. Other ESD circuit implementations may be used as well.

Referring to FIG. 13, an ESD protection array is illustrated for protecting the local clock multiplier power domains, and for cascading protection among the power traces of different power domains. In FIG. 13, the power trace 414V for an individual phase locked loop, and the ground trace 414G for the individual phase locked loop are shown. An ESD protection circuit 925 is connected between traces 414G and 414V and the corresponding pads VDDP, GNDP. Circuit 925 may be implemented using a reversed biased diode configuration in a grounded gate NMOS technology as well.

ESD protection circuits 910, 911, 912, and 913 are connected on one terminal to the power trace 411V connected to VDDA for the analog power domain. Circuit 910 is connected on its opposing terminal to the power trace 412V connected to VDDD in the digital power domain. Circuit 911 is connected on its opposing terminal to the power trace 413V connected to VDDO in the transmitter power domain.

A similar pattern may be distributed around the periphery of the chip, so that circuit 912 is connected on its opposing terminal to the power trace 413V connected to VDDO in the transmitter power domain. Circuit 913 may be connected on its opposing terminal to the power trace 412V connected to VDDD in the digital power domain.

A second tier of ESD circuits includes circuits 914, 915, 916 and 917, connected on one terminal to the analog ground trace 411G which may be connected to the analog ground pad GNDA for the analog power domain. Circuit 914 may be connected on its opposing terminal to the ground trace 412G connected to GNDD in the digital power domain. Circuit 915 may be connected on its opposing terminal to the ground trace 413G connected to GNDO in the transmitter power domain. A similar pattern may be distributed around the chip, so that circuit 916 is connected on its opposing terminal to the ground trace 413G connected to GNDO in the transmitter power domain. Circuit 917 is connected on its opposing terminal to the ground trace 412G connected to GNDD in the digital power domain.

The third tier of ESD circuits includes circuits 918 and 919. Circuits 918, 919 each include one terminal coupled to the power trace 412V that is connected to VDDD in the digital power domain. Both of the circuits 918, 919 have opposing terminals connected to the power trace 413V that is connected to VDDO in the transmitter power domain.

A fourth tier of ESD circuits includes circuits 920 and 921. Circuits 920 and 921 are both connected between the ground trace 412G that is connected to GNDD in the digital power domain, and the ground trace 413G that is connected to GNDO in the transmitter power domain.

Individual clock multiplier power domains are also protected by ESD circuits 926, 927 and 930. ESD circuits 926 and 927 have one terminal connected to the power trace 414V that is connected to the VDDP for the local clock multiplier power domain. Circuit 926 has an opposing terminal connected to the trace 411V that is connected to VDDA in the analog power domain. Circuit 927 has an opposing terminal connected to ground trace 413G in the transmitter power domain.

The ESD circuit 930 has one terminal connected to the ground trace 414G that is connected to GNDP of the local clock multiplier power domain, and an opposing terminal connected to the ground trace 413G that is connected to GNDO in the transmitter power domain.

Circuit 927 which is connected between a ground trace and a power trace, may be implemented using a reverse biased diode configuration in a grounded gate NMOS technology, consistent with the example given above for protection between power and ground traces.

The circuits which protect between power traces in different power domains, including the circuits 910 through 913, 918, 919 and 926, may be implemented using a reverse biased diode configuration in a grounded gate NMOS technology, consistent with the example given above for protection between power and ground traces.

Circuits which protect between ground traces in different power domains, including the circuits 914 through 917, 920, 921 and 930 may be implemented using back-to-back parallel diodes.

Figure 14:
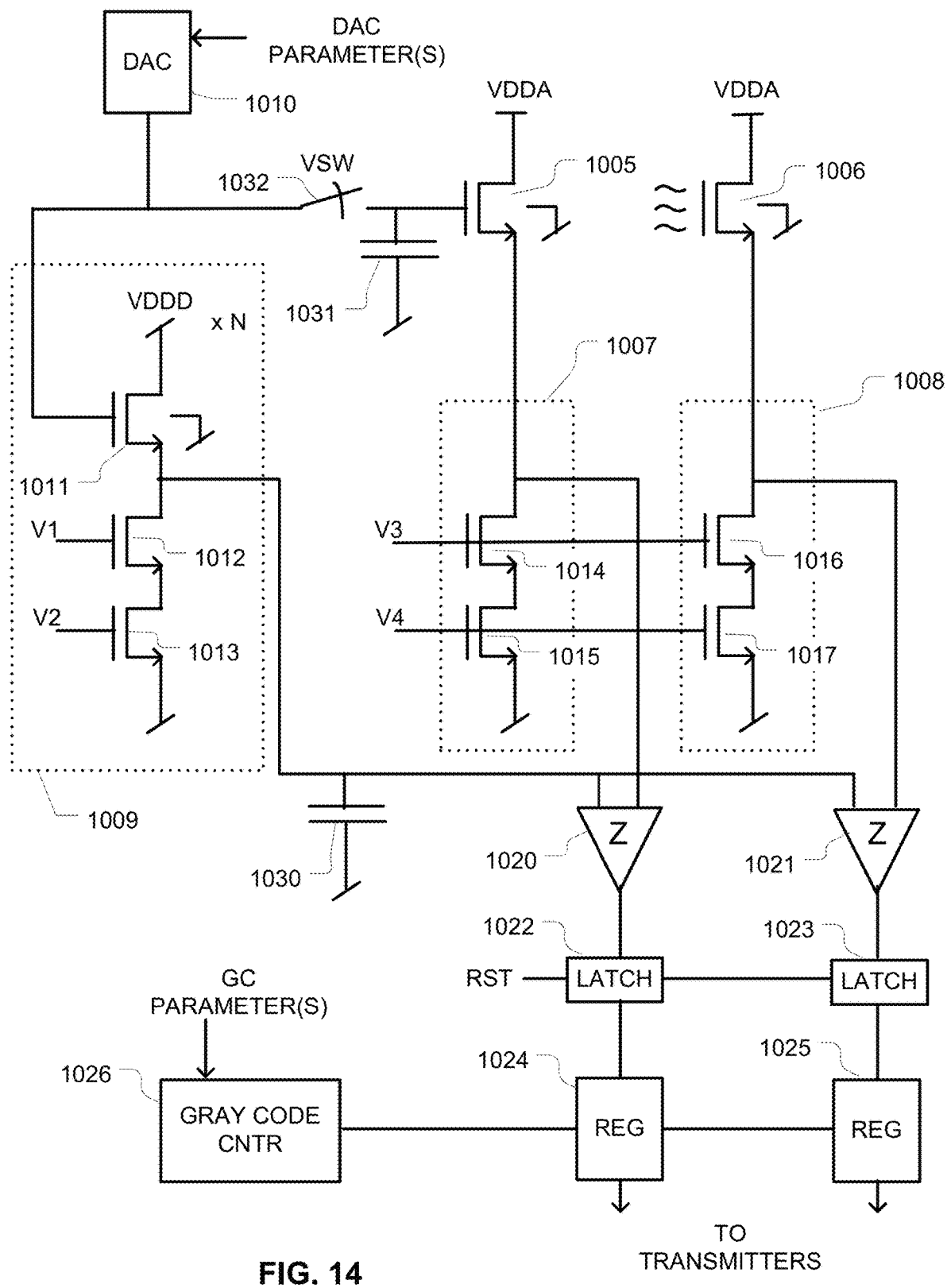
FIG. 14 is a simplified schematic diagram showing peripheral circuitry on a sensor device, subject of power control as described herein.

FIG. 14 is a schematic illustration showing components of the peripheral circuitry on an integrated circuit sensor like that shown in FIG. 4, which may be parts of the column bias/select circuits 402L/402U, analog-to-digital converter circuits 403L/403U, and register arrays 404L/404U. The circuit includes, schematically, a reference cell 1005 and an ISFET 1006 having drain terminals coupled to the analog power supply potential VDDA. The source terminals in the simplified illustration of the reference cell 1005 and the ISFET 1006 are coupled to matched current sources 1007, 1008 respectively. The current source 1007 coupled to the reference cell 1005 includes cascode transistor 1014 in series with a current source transistor 1015 which are biased using reference voltages V3 and V4, respectively. A node at the drain terminal of the cascode transistor 1014 is connected to the input of a comparator 1020. The current source 1008 coupled to the ISFET 1006 includes cascode transistor 1016 and current source transistor 1017 in series, which are biased using reference voltages V3 and V4, respectively. A node at the drain terminal of the cascode transistor 1016 is connected to the input of a comparator 1021.

A ramp voltage may be applied to second inputs of the comparators 1020, 1021. The ramp voltage may be generated by a digital-to-analog converter (DAC) 1010 and a ramp driver 1009. The ramp driver 1009 includes transistors 1011, 1012, and 1013 in series between the digital power supply voltage VDDD and ground. The gate of the transistor 1011 may be controlled by the output of the digital-to-analog converter 1010. Transistor 1012 may be configured as a cascode transistor controlled by the bias voltage V1. The transistor 1013 may be a current source transistor controlled by the bias voltage V2. A node at the drain of transistor 1012 is connected to the second inputs of the comparators 1020 and 1021. A capacitor 1030 may be coupled to the node to stabilize the ramping voltage. Digital-to-analog converter 1010 may be digitally controlled to produce a ramp voltage connected to the gate of the transistor 1011, having a desired ramp shape, timed with the frame sequences. Also, the output of the digital-to-analog converter 1010 may be coupled to a switch 1032. The switch 1032 may be operated to connect the output of the digital-to-analog converter 1010 to a capacitor 1031 during a selected part of the ramp cycle. The voltage on the capacitor 1031 may be used as the reference voltage on the gate of the reference cells 1005.

The outputs of the comparators 1020 and 1021 are coupled to respective latches 1022, 1023. Latches 1022, 1023 are reset at the beginning of each cycle, and are operated to capture a transition on the output of the respective comparators 1020, 1021. The outputs of the latches are coupled to corresponding registers 1024, 1025. A gray code counter 1026 is connected to the registers 1024, 1025, and may be cycled in time with the ramp voltage.

The comparators 1020, 1021 transition when the ramp voltage on the capacitor 1030 matches the voltage produced by the reference cell 1005 or ISFET 1006 to which they are coupled. When the latches 1022, 1023 capture the transition of the comparators 1020, 1021, the output of a gray code counter 1026 may be captured in a corresponding register 1024, 1025. The gray code values captured in the registers 1024, 1025 are provided as a stream of data to the transmitters.

Using the circuitry shown, streams of data are provided to the transmitters which represents pixels from the sensor array.

The circuitry illustrated in FIG. 14, with the exception of the reference cell 1005 and ISFET 1006 and their corresponding current sources 1007, 1008, may be implemented in the digital power domain, and thereby isolated from the analog power domain, the transmitter power domain, and the clock multiplier power domains.

The dynamics of the incorporation event for DNA sequencing using ISFETs may occur ar approximately 15 frames per second. The sensor may run at a higher frame rate for oversampling in order to improve the signal-to-noise ratio. The capture window of interest can typically be a few seconds. Due to reagent flow producing skewed reactions times across the chip, active and idle intervals may be adjusted to achieve good results. In one example, 7 seconds of data may be captured in a 20 second cycle time. Chips that produce larger amounts of data may have longer cycle times in order to process the data. Energy may be wasted in the sensor during the period where data is not captured.

Power management may be used to reduce the power consumption during the idle periods.

In addition, power management can enable paused or reduced flow cycles during the wash cycles, where reagents are conserved. Power states and flow rates may be tuned to optimize reagent use and the temperature of the chip under variable flow.

Power management in the fluidic systems as described herein may be constrained by a variety of factors. For example, typically reagents are continuously flowing in order to keep the chip temperature stable. The chip interfaces to the fluidics through capacitive coupling. Changes in signal level, pixel timing and readout sequence (control) affect the electro fluidics, which can change the parameters of the capacitive coupling and destabilize the readout process.

The chip interfaces to a reader board through high speed links. The high speed links are initially synchronized as a transmitter-receiver pair and may lock. Changing the transmission protocol or the readout parameters may invalidate the initial pairing. Link loss takes time to recover, and may make high data rate readout impossible.

In some embodiments, the power management may be provided with no disruption to the electro fluidics. However, the pixel array may create capacitive feedback into the fluidics and may be signal dependent.

In some embodiments, power management and thermal management may be enabled using a simple interface. The system may be busy with processing data and may require a simple interaction to initiate a capture sequence. Thus, synchronous power states may be used, in which the duty cycle between active and sleep states may be consistent or managed to avoid variation in average heat dissipation.

One example of a power management parameter is an effective number of bits for the output digital-to-analog converter. Converting an analog to a digital signal may require a certain amount of energy based on the noise floor and dynamic range of the signal, the conversion rate (Mega-Samples per second), conversion cycle time (e.g. frame rate) architecture (not a fundamental noise source), and the output drive power from the ADC. As shown in FIG. 4, and similar systems, the electro fluidics may not see the data conversion. Also, the data transmitted from the chip may use scrambling (i.e. in the transmitter serializer block) and the data link integrity may be unaware of the quality of the data conversion. Also, the ADC sequence may be synchronous to the row time/frame time.

During the capture sequence, the ADC can run with a 12-bit effective number of bits (ENOB). During the idle period, the ADC can run at an 8-bit (or N-bit) ENOB. A 4-bit ENOB can save up to 16 times in power consumption at the ADC and yet nothing in the system may be aware of the change in ENOB (no listeners). Thus, during the idle mode, ADC may be configured by control parameters to operate at lower ENOB values.

Circuitry illustrated in FIG. 14 may be operated in active and idle modes to adjust power consumption and to control temperature during active and idle periods using a set of parameters on a frame by frame basis. The circuitry can implement for example, a proportional-integral-derivative PID control algorithm to manage power consumption, and temperature of the chip.

The controllable parameters for circuitry in the digital power domain include parameters for the digital-to-analog converter "DAC PARAMETER(S)" such as a DAC head parking address, gray code counter parameters "GC PARAMETER(S)" such as a gray code parking address, ramp driver parameters V1, V2 which set of comparator power levels, the timing of the signal VSW controlling the switch 1032, in this example. In other circuitry implementations, other types of parameters may be controlled on a frame-by-frame basis. Likewise, in the illustrated circuitry other parameters may be controlled to manage power consumption by the peripheral circuitry. Other parameters include for example, bias levels for the comparators 1020, 1021 and bias levels for the latches 1022, 1023.

In addition, parameters controlling the current sources 1007, 1008 may be used to control power consumption on a frame-by-frame basis of circuitry in the analog power domain. These parameters include the bias voltages V3 and V4 in the illustrated example which set pixel column bias levels. The control of the current sources 1007, 1008 is optional. In preferred examples, the current sources 1007, 1008 are controlled so as to avoid destabilizing the interfacial fluid dynamics and electrical operation of the sensor array. For example, the parameters may be changed slowly or only in small amounts, and transitions from the idle mode to the active mode may be executed well in advance of the readout of active data in order to maintain consistent electrofluidics from frame to frame.

Other parameters can include latch control states, configured to prevent latch transitions in the low power mode. The latch control states may be specified to set latch output values during the idle modes, in a pattern that facilitates maintenance of the transmission links and low transition counts (and thus reduced power consumption) for the data paths to the transmitters.

Embodiments are envisioned in which any one of the frame power parameters, or more than one of the frame power parameters, described above are adjusted in idle mode to reduce power consumption.

Figure 15:
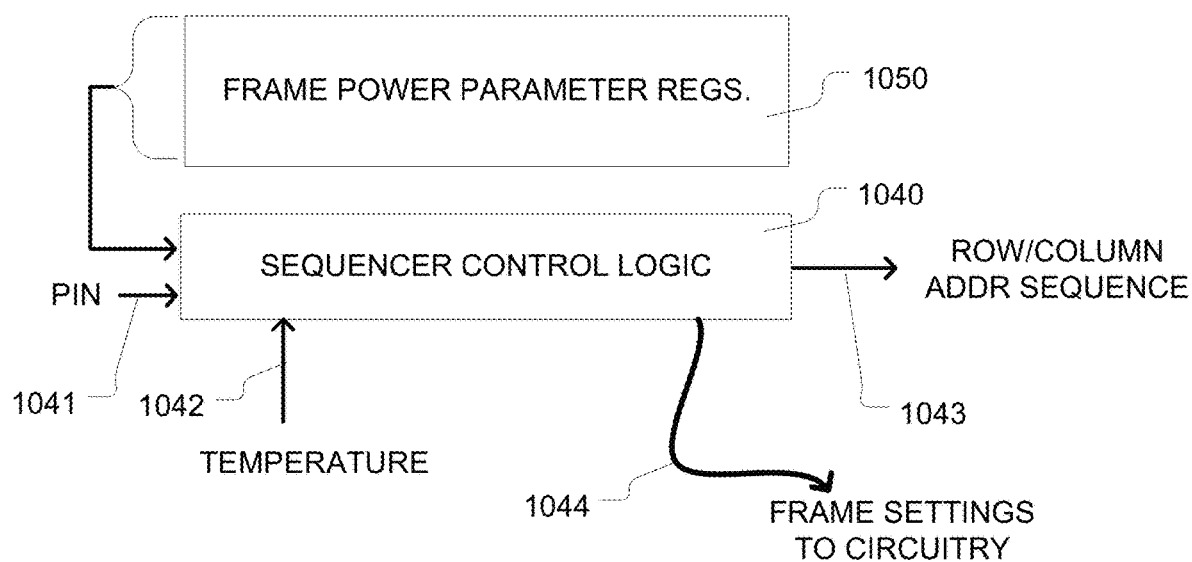
FIG. 15 is a simplified diagram of sequencer control logic which may be used for management of power consumption and temperature as described herein.

FIG. 15 is a simplified illustration of control logic in the sequencer on a chip like that shown in FIG. 4. The control logic includes a set of frame power parameter registers 1050 and a sequencer control logic block 1040. The sequencer control logic block 1040 is connected to an input signal provided by a pin 1041 on the integrated circuit, at which a control signal may be applied to activate sample sequences, in some embodiments. Alternatively, the sequencer control logic block 1040 may be activated by control signals generated on-chip or written to a register set using the SPI interface or other management interface on the device. Sequencer control logic block 1040 also receives input from the temperature sensors on the chip on line 1042, and produces timing signals for addressing to capture a frame of pixels on line 1043. Sequencer control logic 1040 produces frame settings (represented by line 1044) for the active and idle modes in response to the value stored in the frame power parameter registers 1050, such as discussed above in connection with FIG. 14.

A representative set of parameters can include the following:

```
reg.set('lp_trigger', 0)            #control setting to trigger the start of a capture.
reg.set('lp_mode.en', 0)            #control setting to enable low power time sequencing.
reg.set('lp_mode.force', 0)         #control setting force the low power phase to run
                                     continuously.
reg.set('lp_frame_count', 0)        #control setting to set duration of active period specified by
                                     frame count.
reg.set('lp_status', 0)             #status parameter indicating low power state.
reg.set('lp_bias.enI_vbn_cb', 0)    #vbn_cb : bias current sink for cb pixel column line (e.g.
                                     V4).
reg.set('lp_bias.enI_vbn_ct', 0)    #vbn_ct : bias current sink for ct pixel column line (e.g. V4).
reg.set('lp_bias.enI_vbn_rmp', 0)   #vbn_rmp : bias current sink for ramp bias (e.g. V2).
reg.set('lp_bias.enI_vbp_cmp', 0)   #vbp_cmp : bias current source for 1st stage comparator bias
                                     (two stage comparator).
reg.set('lp_bias.enI_vbp_smp', 0)   #vbp_smp : bias current source for 2nd stage comparator
                                     bias (two stage comparator).
reg.set('lp_bias.mask', 0)          #mask for {vbp_smp,vbp_cmp,vbn_rmp,vbn_ct,vbn_cb}
                                     (selecting circuit parameters to apply in low-power mode).
reg.set('lp_ctrl.latch_rst0', 0)    #low power state for latch_rst0.
reg.set('lp_ctrl.latch_set0', 1)    #low power state for latch_set0.
reg.set('lp_ctrl.latch_rst1', 1)    #low power state for latch_rst1.
reg.set('lp_ctrl.latch_set1', 0)    #low power state for latch_set1.
reg.set('lp_ctrl.mask', 0)          #mask for {gray code, dacbuf_en_sf, dac_head, latch}
                                     selecting control settings to apply in low-power mode).
```

| | |
|---|---|
| reg.set('mode.stall_pin', 1) | #set to 0 to configure the stall pin (e.g. pin 1041) as an lp_trigger. |
| reg.set('gray fixed', 0) | #fixed value for gray code input (e.g. constant input to register set). |

In example processes, the chip may be notified of the start of a capture sequence by activation of a pin input, by register write or otherwise. The chip runs active for a certain period, which may be fixed, programmable or dynamically adjusted, and then transitions to a low-power state. The low-power state is configurable by selecting parameters and levels of control values to control. The active and idle periods may be programmable, and may be set by the chip in a manner that may not be synchronous with the reactant flows and wash cycles.

The state of the chip may be embedded in the metadata in the register set, or may be in the data streams transmitted to the reader. The state of the chip may be available over the SPI interface or other management bus interface in some embodiments. The system may capture data during the active cycles of the chip, and may continue transmitting data not based on the sensors, during idle cycles to maintain the communication links. The start and stop times for the active and idle cycles may be determined based on a number of timing parameters, including a number of clock cycles, a number of row cycles or a number of frame cycles. Also and/or optionally using the number of frame cycles to determine start and stop times may be useful because second order effects may be captured at frame intervals rather than during some random time during capture. For fine timing control, a combination of timing parameters may be utilized.

Figure 16:
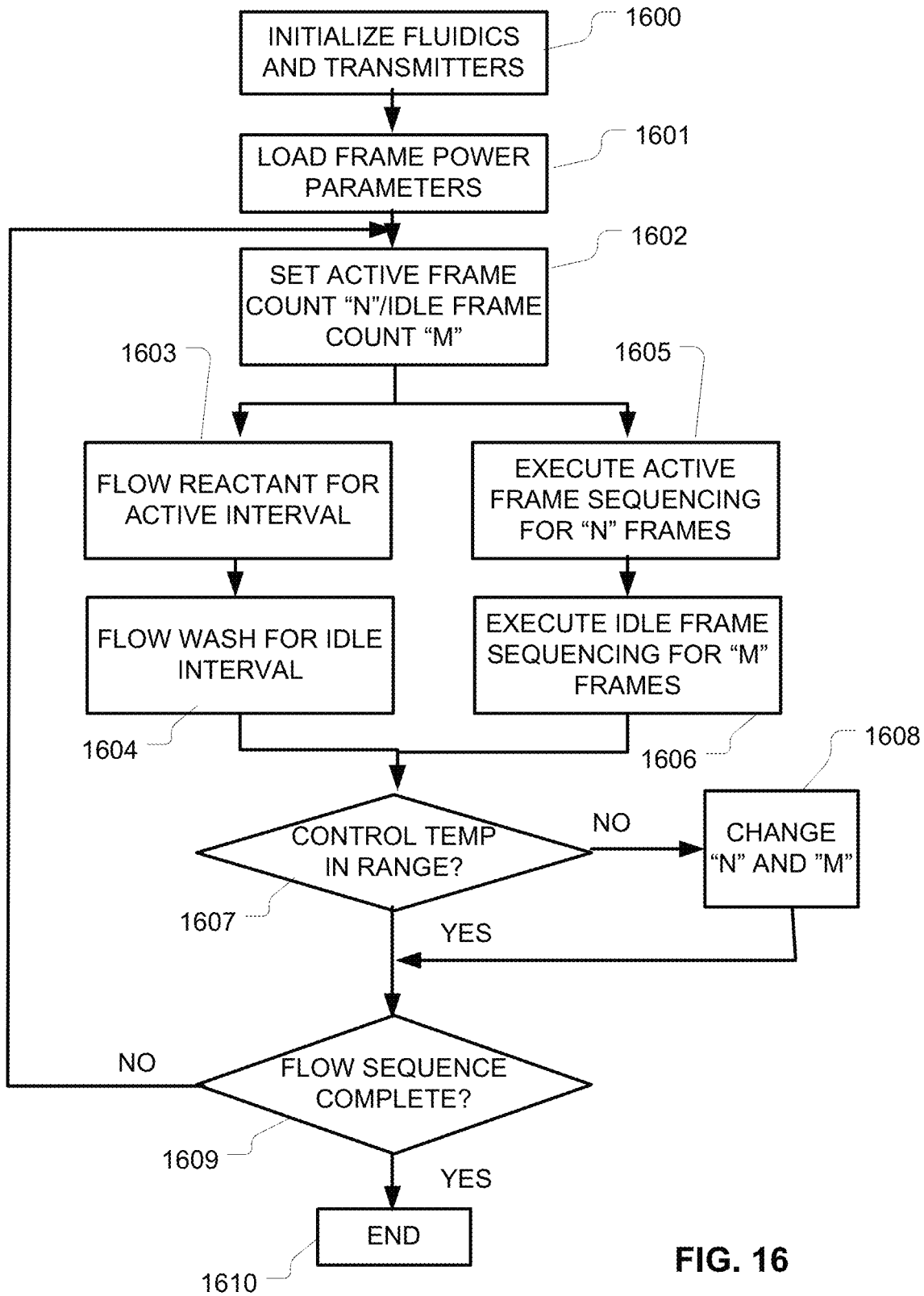
FIG. 16 is a flowchart showing a method of operating a sensor system as described herein.

FIG. 16 is a simplified flowchart for control of a flow cycle using a system like that shown in FIG. 1 utilizing power management techniques as described herein. The process includes initializing the fluidics for delivering reactant and wash fluids, and initializing the transmitters on the chip to establish communication links with a reader (1600). Also, the process includes loading frame power parameters on the chip, or in the system so that they may be provided to the chip as needed (1601). The frame power parameters in this example provide power settings for each frame sensing cycle, including active mode frame settings and idle mode frame settings. The process includes setting the active frame count "N" and the idle frame count "M" for a particular flow cycle including a reactant flow and a wash flow. The system then controls the fluidics in a cycle that includes flowing a reactant for an active interval (1603) and flowing a wash for an idle interval (1604). In parallel with the fluidics, the sensor chip may be controlled to execute active frame sequencing for "N" frames (1605), followed by executing idle frame sequencing for "M" frames (1606). The process includes determining whether a control temperature may be within an operating range (1607). If not, then the active frame count "N" and the idle frame count "M" are changed (1608). After, in the illustrated flow diagram, the active frame count "N" and the idle frame count "M" are changed, or if the control temperature is within the operating range at block (1607), then the process determines whether the flow sequence is complete (1609). If the sequence is not complete, then the process loops back to block 1602, and performs a following flow cycle. If the sequence is complete, then the process is ended (1610).

Figure 17:
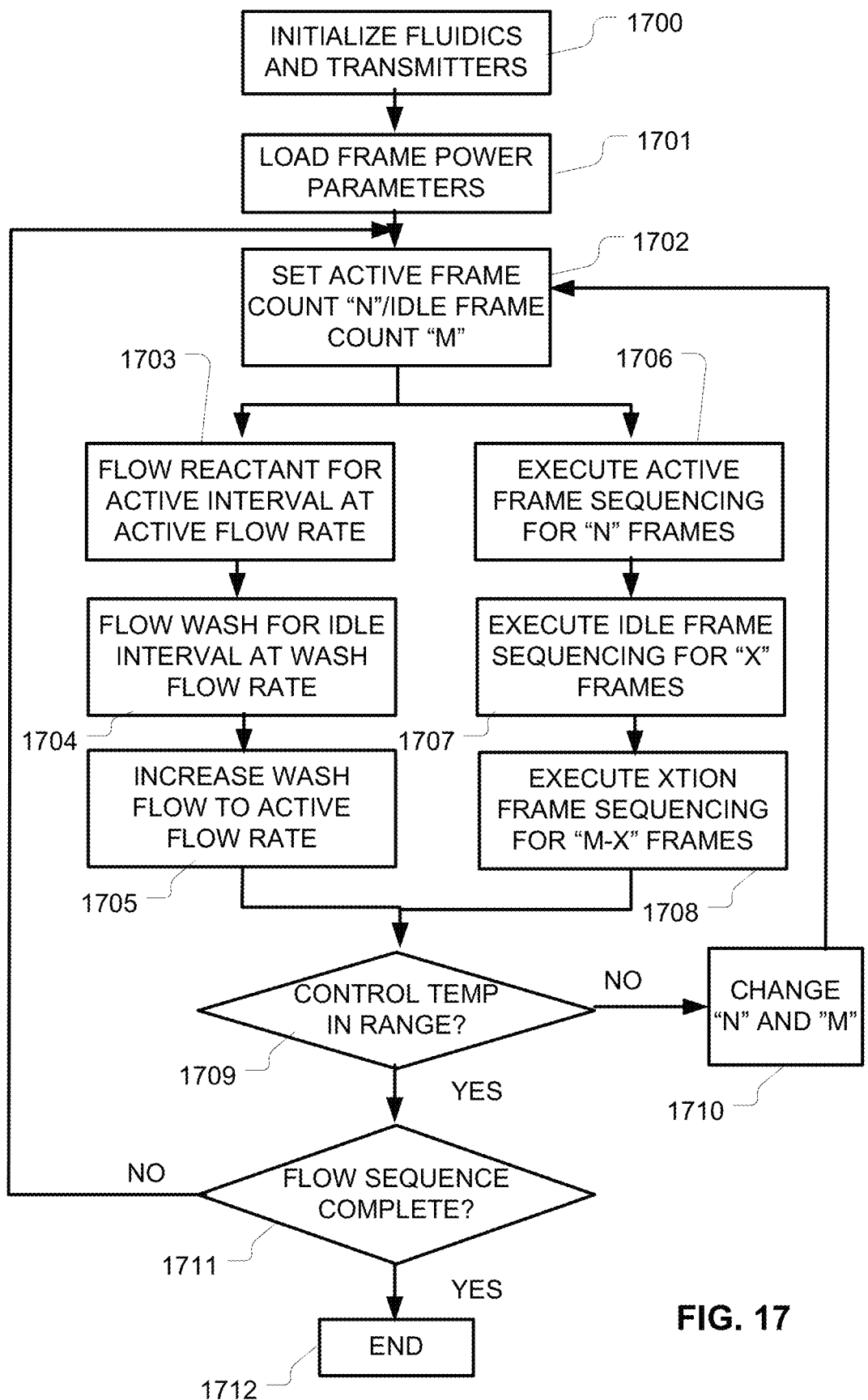
FIG. 17 is a flowchart showing an alternative method of operating a sensor system as described herein.

FIG. 17 is a simplified flowchart for an alternative control process for a flow cycle using a system like that shown in FIG. 1 utilizing power management techniques as described herein. The process includes initializing the fluidics for delivering reactant and wash fluids, and initializing the transmitters on the chip to establish communication links with a reader (1700). Also, the process includes loading frame power parameters on the chip, or in the system so that they may be provided to the chip as needed (1701). The frame power parameters in this example provide power settings for each frame sensing cycle, including active mode frame settings and idle mode frame settings. The process includes setting the active frame count "N" and the idle frame count "M" for a particular flow cycle including a reactant flow and a wash flow. The system then controls the fluidics in a cycle that includes flowing a reactant for an active interval at an active flow rate (1703) and flowing a wash for an idle interval at a wash flow rate which may be less than the active flow rate (1704). Next, for transition to a next flow cycle, the wash flow rate may be increased to the active flow rate in order to stabilize the electric fluidics in advance of the active sensing cycles (1705). In parallel with the fluidics, the sensor chip may be controlled to execute active frame sequencing for "N" frames (1706), followed by executing idle frame sequencing for "X" frames (1707). Next, for transition to a next mode, a transition frame sequencing may be executed for "M-X" frames (1708). The process includes determining whether a control temperature is within an operating range (1709). If not, then the active frame count "N" and the idle frame count "M" are changed (1710). In some embodiments, the transition parameter "M-X" may be changed as well. If the active frame count "N" and the idle frame count "M" are changed, or if the control temperature is within the operating range at block (1709), then the process determines whether the flow sequence is complete (1711). If the sequence is not complete, then the process loops back to block 1702, and performs a following flow cycle. If the sequence is complete, then the process is ended (1712). In this manner, transitional control is provided so that the electro fluidics and thermodynamics of the interface region may be stabilized in advance of switching to the active mode, even if the electro fluidics and thermodynamics may be changed during the idle mode, due to, for example, the reduced flow rate during the wash flow and changes in biasing levels in the sensor array that may occur during the idle frame sequencing. It may be desirable however that the electric fluidics and thermodynamics remain stable throughout a flow cycle, so that the transitional flow and transition frame sequencing may not be necessary.

FIGS. 16 and 17 are flowcharts illustrating logic executed by the sequencing system. The logic may be implemented using on-chip circuitry such as state machines, processors programmed using computer programs stored in memory accessible to the computer systems and executable by the processors, by dedicated logic hardware, including field programmable integrated circuits, and by combinations of dedicated logic hardware and computer programs. As with all flowcharts herein, it will be appreciated that many of the steps may be combined, performed in parallel or performed in a different sequence without affecting the functions achieved. In some cases, as the reader will appreciate, a rearrangement of steps will achieve the same results only if certain other changes are made as well. In other cases, as the reader will appreciate, a rearrangement of steps will achieve the same results only if certain conditions are satisfied. Furthermore, it will be appreciated that the flow charts herein show only steps that are pertinent to an understanding of the invention, and it will be understood that numerous additional steps for accomplishing other functions may be performed before, after and between those shown.

A method for operating a sensor array is described therefore, which includes applying a sequence of alternating flows of reactant solutions during active intervals and flows of wash solutions during wash intervals; applying bias arrangements to the sensor array to produce sensor data; producing streams of sensor data from the sensor array using peripheral circuitry having an active mode and an idle mode; and switching the peripheral circuitry between the active mode and the idle mode to control power consumption. The method can include using feedback responsive to temperature of the array to switch between the active mode and the idle mode to maintain the temperature within an operating range.

The peripheral circuitry can include conversion circuitry, responsive to configuration parameters, to convert the sensor data into a plurality of streams of digital data; a plurality of transmitters configured to receive corresponding streams of data from the plurality of streams from the conversion circuitry and transmit the data to corresponding receivers; and a sequencer which operates the bias circuitry to produce frames of sensor data at a frame rate, operates the conversion circuitry to convert the sensor data at the frame rate. In support of this configuration, the method can include applying a first set of one or more configuration parameters to the conversion circuitry in the active mode, and a second set of one or more configuration parameters to the conversion circuitry in the idle mode and maintaining transmission of data using the plurality of transmitters during the idle mode. The second set of configuration parameters may be adapted to preserve operational readiness and to reduce power consumption. Also, the method can include applying a third set of one or more configuration parameters to the bias circuitry in the active mode, and a fourth set of one or more configuration parameters to the bias circuitry in the idle mode.

Also, the method can include maintaining communication links with remote receivers during the active mode and the idle mode.

In one example, the method includes operating in the active mode for a first number of frames in a time interval overlapping with the active interval and for a second number of frames in the idle mode in a time interval overlapping with an immediately following idle interval; and adjusting the first and second numbers to control power consumption.

The system can provide an average flow rate during the active interval which may be greater than an average flow rate during the idle interval, the reduced flow rates being offset by idle mode power settings on the sensor array, and reducing consumption of reaction fluids.

In examples in which the peripheral circuitry includes an analog-to-digital ADC converter, the method can include setting a first effective number of bits parameter for the analog-to-digital converter in the active mode, and a second effective number of bits parameter, lower than the first, for the analog-to-digital converter in the idle mode.

In examples in which the peripheral circuitry includes a digital-to-analog DAC converter to produce a reference ramp signal, the method can include setting a DAC parking address parameter for the digital-to-analog converter in the idle mode.

In examples in which the peripheral circuitry includes a gray code counter to produce a digital count value, the method can include setting a gray code counter parking address parameter in the idle mode.

In examples in which the peripheral circuitry includes a comparator, the method can include setting a first comparator power level parameter in the active mode, and a second comparator power level parameter, lower than the first, in the idle mode.

In examples in which the peripheral circuitry includes a latch for each column of the array, the method can include setting a latch state in the idle mode.

The technology described herein provides for tunable ADC power consumption for bandwidth and thermal noise, mode selectable gray code capture for continuous or pulse mode sampling, and automatic power management configured for N-number of frame sequences.

Power management may be used to reduce the power consumption during the idle periods.

In addition, power management can enable paused flow cycles where reagents are conserved. Typically reagents are continuously flowing in order to keep the chip temperature stable. Power states and flow rates may be tuned to optimize reagent use and the temperature of the chip under variable flow.

A configuration for implementing an array of high-speed transmitters on an integrated circuit is described. Features of the implementation include local high-speed transmit clock generation, and provide a clock multiplier such as a phase locked loop, between each pair of transmitters which provides a local high speed transmit clock over short connectors to the adjacent transmitters. Another feature of the implementation includes low speed reference clock distribution, allowing for the distribution of the reference clock to the transmitter array at low power and low frequency, minimizing disturbance of the transmitters from reference clock noise. Also, features of the implementation include power supply separation, providing individual power domains for the clock multiplier circuitry, separate from the transmitters, from digital circuitry and from analog circuitry on the device minimizing disturbance of the transmitter from noise arising in other portions of the chip which operate on separate clocks and introduce additional noise sources. Power consumption and temperature may be managed by controlling power utilized in the digital domain only, while maintaining operational readiness of the circuitry in the analog domain, transmitter domain and clock multiplier domain.

In some embodiments, an integrated circuit is described which includes a substrate having a data source, with peripheral circuitry on the substrate coupled to the data source to produce a stream of digital data. To support high speed transmission of the data stream, a clock multiplier may be provided on the substrate which produces a transmit clock. The clock multiplier may be disposed in an individual power domain on the substrate to reduce noise and improve quality of the transmit clock. A transmitter may be on the substrate and configured to receive the stream of data from the data source. The transmitter is connected to transmit the stream of data on an output pad using the transmit clock. The transmitter may be disposed in a transmitter power domain on the substrate separate from the individual power domain of the clock multiplier. In other aspects of the technology, the data source and the peripheral circuitry are disposed in a power domain or power domains separate from the individual power domain. The integrated circuit can include a plurality of transmitters on the substrate connected to, and thereby sharing, the clock multiplier. In other aspects, a plurality of clock multipliers may be disposed on the substrate which produce respective local transmit clocks, in which each clock multiplier may be disposed in an individual power domain on the substrate. In this aspect, a plurality of transmitters on the subset are arranged in sets having one or more members, and wherein each set may be placed in proximity to, and connected to, one clock multiplier in the plurality of the clock multipliers. Power consumption and temperature may be managed dynamically without disturbing operational readiness using the techniques described herein.

While the claimed invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. A method for operating a sequencing system including a sensor array, comprising:
    applying a sequence of alternating flows of reactant solutions during active intervals and flows of wash solutions during wash intervals;
    applying bias arrangements to the sensor array to produce sensor data;
    producing streams of sensor data from the sensor array using peripheral circuitry having an active mode and an idle mode; and
    switching the peripheral circuitry between the active mode and the idle mode to control power consumption.

2. The method of claim 1, including using feedback responsive to temperature of the array to switch between the active mode and the idle mode to maintain the temperature within an operating range.

3. The method of claim 1, wherein the peripheral circuitry includes:
    converting, with conversion circuitry responsive to configuration parameters the sensor data into a plurality of streams of digital data;
    receiving, at a plurality of transmitters, corresponding streams of data from the plurality of streams from the conversion circuitry and transmitting the data to corresponding receivers; and
    producing, at a sequencer which operates bias circuitry, frames of sensor data at a frame rate, operates the conversion circuitry to convert the sensor data at the frame rate; and further comprising:
        applying a first set of one or more configuration parameters to the conversion circuitry in the active mode, and a second set of one or more configuration parameters to the conversion circuitry in the idle mode and maintaining transmission of data using the plurality of transmitters during the idle mode.

4. The method of claim 3, including applying a third set of one or more configuration parameters to the bias circuitry in the active mode, and a fourth set of one or more configuration parameters to the bias circuitry in the idle mode.

5. The method of claim 3, wherein the second set of configuration parameters is adapted to preserve operational readiness and to reduce power consumption.

6. The method of claim 1, including maintaining communication links with remote receivers during the active mode and the idle mode.

7. The method of claim 1, including:
    operating in the active mode for a first number of frames in a time interval overlapping with the active interval and for a second number of frames in the idle mode in a time interval overlapping with an immediately following idle interval; and
    adjusting the first and second numbers to control power consumption.

8. The method of claim 7, wherein an average flow rate during the active interval is greater than an average flow rate during the wash interval.

9. The method of claim 1, wherein the sensor array comprises chemically sensitive field effect transistors.

10. The method of claim 1, wherein the peripheral circuitry includes an analog-to-digital ADC converter, and including:
    setting a first effective number of bits parameter for the analog-to-digital converter in the active mode, and a second effective number of bits parameter, lower than the first, for the analog-to-digital converter in the idle mode.

11. The method of claim 1, wherein the peripheral circuitry includes a digital-to-analog DAC converter to produce a reference ramp signal, including:
    setting a DAC parking address parameter for the digital-to-analog converter in the idle mode.

12. The method of claim 1, wherein the peripheral circuitry includes a gray code counter to produce a digital count value, and including:
    setting a gray code counter parking address parameter in the idle mode.

13. The method of claim 1, wherein the peripheral circuitry includes a comparator, and including:
    setting a first comparator power level parameter in the active mode, and a second comparator power level parameter, lower than the first, in the idle mode.

14. The method of claim 1, wherein the peripheral circuitry includes a latch for each column of the array, and including:
    setting a latch state in the idle mode.

* * * * *